(12) United States Patent
Beasley et al.

(10) Patent No.: US 6,740,504 B2
(45) Date of Patent: May 25, 2004

(54) ISOLATED HUMAN SECRETED PROTEINS, NUCLEIC ACID MOLECULES ENCODING HUMAN SECRETED PROTEINS, AND USES THEREOF

(75) Inventors: Ellen M Beasley, Darnestown, MD (US); Ming-Hui Wei, Germantown, MD (US); Fangcheng Gong, Germantown, MD (US); Steven I Ladunga, Foster City, CA (US); Maureen E Higgins, Bethesda, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/841,158

(22) Filed: Apr. 25, 2001

(65) Prior Publication Data

US 2003/0166046 A1 Sep. 4, 2003

(51) Int. Cl.⁷ .......................... C12N 15/12; C12N 5/10; C12P 21/02; C07K 14/47
(52) U.S. Cl. .................. 435/69.1; 435/71.1; 435/320.1; 435/471; 435/252.3; 435/325; 536/23.5; 530/350
(58) Field of Search ............................... 435/69.1, 71.1, 435/320.1, 471, 252.3, 325; 536/23.5; 530/350

(56) References Cited

PUBLICATIONS

Structural genomics and its importance for gene function analysis, Nature Biotechnology, vol. 18, pp. 283–287. Mar. 2000.*

Quadros et al. "Purification and Molecular Characterization of Human Transcobalamin II." Journal of Biological Chemistry, Nov. 25, 1986, vol. 261, No. 33, pp. 15455–15460.

Platice et al. "The cDNA Sequence and the Deduced Amino Acid Sequence of Human Transcobalamin II Show Homology with Rat Intrinsic Factor and Human TRanscobalamin I," Journal of Biological Chemistry, Apr. 25, 1991, vol. 266, No. 12, pp. 7860–7863.

Regec et al. "The Cloning and Characterization of the Human Transcobalamin II Gene." Blood. May 15, 1995, vol. 85, No. 10, pp. 2711–2719.

Database GenBank (A–Geneseq); Accession No. AAB58138; Ruben SM; "Lung Cancer Associated Polypeptide SEQ ID NO:476." Sep. 21, 2000.

International Search report dated Nov. 25, 2003.

* cited by examiner

*Primary Examiner*—Gary Kunz
*Assistant Examiner*—Fozia Hamud
(74) *Attorney, Agent, or Firm*—Celera Genomics; Justin D. Karjala

(57) ABSTRACT

The present invention provides amino acid sequences of peptides that are encoded by genes within the human genome, the secreted peptides of the present invention. The present invention specifically provides isolated peptide and nucleic acid molecules, methods of identifying orthologs and paralogs of the secreted peptides, and methods of identifying modulators of the secreted peptides.

8 Claims, 30 Drawing Sheets

Isoform 1:

```
   1 TTGCTCACTG CTCACCCACC TGCTGCTGCC ATGAGGCACC TTGGGGCCTT
  51 CCTCTTCCTT CTGGGGGTCC TGGGGGCCCT CACTGAGATG TGTGAAATAC
 101 CAGAGATGGA CAGCCATCTG GTAGAGAAGT TGGGCCAGCA CCTCTTACCT
 151 TGGATGGACC GGCTTTCCCT GGAGCACTTG AACCCCAGCA TCTATGTGGG
 201 CCTACGCCTC TCCAGTCTGC AGGCTGGGAC CAAGGAAGAC CTCTACCTGC
 251 ACAGCCTCAA GCTTGGTTAC CAGCAGTGCC TCCTAGGGTC TGCCTTCAGC
 301 GAGGATGACG GTGACTGCCA GGGCAAGCCT TCCATGGGCC AGCTGGCCCT
 351 CTACCTGCTC GCTCTCAGAG CCAACTGTGA GTTTGTCAGG GGCCACAAGG
 401 GGGACAGGCT GGTCTCACAG CTCAAATGGT TCCTGGAGGA TGAGAAGAGA
 451 GCCATTGACA CAGCAGCCAT GGCAGGCTTG GCATTCACCT GTCTGAAGCG
 501 CTCAAACTTC AACCCTGGTC GGAGACAACG GATCACCATG GCCATCAGAA
 551 CAGTGCGAGA GGAGATCTTG AAGGCCCAGA CCCCCGAGGG CCACTTTGGG
 601 AATGTCTACA GCACCCCATT GGCATTACAG TTCCTCATGA CTTCCCCCAT
 651 GCGTGGGGCA GAACTGGGAA CAGCATGTCT CAAGGCGAGG GTTGCTTTGC
 701 TGGCCAGTCT GCAGGATGGA GCCTTCCAGA ATGCTCTCAT GATTTCCCAG
 751 CTGCTGCCCG TTCTGAACCA CAAGACCTAC ATTGATCTGA TCTTCCCAGA
 801 CTGTCTGGCA CCACGAGTCA TGTTGGAACC AGCTGCTGAG ACCATTCCTC
 851 AGACCCAAGA GATCATCAGT GTCACGCTGC AGGTGCTTAG TCTCTTGCCG
 901 CCGTACAGAC AGTCCATCTC TGTTCTGGCC GGGTCCACCG TGGAAGATGT
 951 CCTGAAGAAG GCCCATGAGT TAGGAGGATT CACATATGAA ACACAGGCCT
1001 CCTTGTCAGG CCCCTACTTA ACCTCCGTGA TGGGGAAAGC GGCCGGAGAA
1051 AGGGAGTTCT GGCAGCTTCT CCGAGACCCC AACACCCCAC TGTTGCAAGG
1101 TATTGCTGAC TACAGACCCA AGGATGGAGA ACCATTGAG CTGAGGCTGG
1151 TTAGCTGGTA GCCCCTGAGC TCCCTCATCC AGCAGCCTC GCACACTCCC
1201 TAGGCTTCTA CCCTCCCTCC TGATGTCCCT GGAACAGGAA CTCGCCTGAC
1251 CCTGCTGCCA CCTCCTGTGC ACTTTGAGCA ATGCCCCTG GGATCACCCC
1301 AGCCACAAGC CCTTCGAGGG CCCTATACCA TGGCCCACCT TGGAGCAGAG
1351 AGCCAAGCAT CTTCCCTGGG AAGTCTTTCT GGCCAAGTCT GGCCAGCCTG
1401 GCCCTGCAGG TCTCCCATGA AGGCCACCCC ATGGTCTGAT GGGCATGAAG
1451 CATCTCAGAC TCCTTGGCAA AAAACGGAGT CCGCAGGCCG CAGGTGTTGT
1501 GAAGACCACT CGTTCTGTGG TTGGGGTCCT GCAAGAAGGC CTCCTCAGCC
1551 CGGGGGCTAT GGCCCTGACC CCAGCTCTCC ACTCTGCTGT TAGAGTGGCA
1601 GCTCCGAGCT GGTTGTGGCA CAGTAGCTGG GGAGACCTCA GCAGGGCTGC
1651 TCAGTGCCTG CCTCTGACAA AATTAAAGCA TTGATGGCCT GTGAAAAAAA
1701 AAAAAAAAAA AAAAAAAAA AA
```
(SEQ ID NO:1)

FEATURES:
5'UTR:        1 - 30
Start Codon:  31
Stop Codon:   1159
3'UTR:        1162

Homologous proteins:
Top 10 BLAST Hits

```
                                                                     Score    E
CRA|108000024653390 /altid=gi|12742775 /def=ref|XP_009922.2| tr...    752    0.0
CRA|108000024636236 /altid=gi|298316   /def=gb|AAB25526.1| transc...  732    0.0
CRA|18000004926133  /altid=gi|339205   /def=gb|AAA61057.1| (L02648... 732    0.0
CRA|108000024042036 /altid=gi|12654675 /def=gb|AAH01176.1|AAH01...    731    0.0
CRA|18000004926130  /altid=gi|4507409  /def=ref|NP_000346.1| tran...  727    0.0
CRA|18000004926132  /altid=gi|339203   /def=gb|AAA61056.1| (L02647... 725    0.0
CRA|18000005170902  /altid=gi|7657639  /def=ref|NP_056564.1| tran... 515    e-145
CRA|18000005218941  /altid=gi|4572454  /def=gb|AAD23829.1|AF12128... 501    e-140
CRA|164000136745249 /altid=gi|11968124 /def=ref|NP_071979.1| tr...   481    e-134
CRA|18000004926134  /altid=gi|4507407  /def=ref|NP_001053.1| tran... 108    2e-22
```

FIGURE 1, page 1 of 4

EST:

| | | |
|---|---|---|
| gi\|10725490 /dataset=dbest /taxon=96... | 858 | 0.0 |
| gi\|10947399 /dataset=dbest /taxon=96... | 846 | 0.0 |
| gi\|9121897 /dataset=dbest /taxon=9606... | 846 | 0.0 |
| gi\|13280819 /dataset=dbest /taxon=96... | 846 | 0.0 |
| gi\|13287907 /dataset=dbest /taxon=96... | 833 | 0.0 |
| gi\|13286505 /dataset=dbest /taxon=96... | 831 | 0.0 |
| gi\|8150776 /dataset=dbest /taxon=960... | 815 | 0.0 |
| gi\|5936410 /dataset=dbest /taxon=9606 ... | 726 | 0.0 |
| gi\|6888875 /dataset=dbest /taxon=9606... | 726 | 0.0 |
| gi\|6888872 /dataset=dbest /taxon=9606... | 726 | 0.0 |

EXPRESSION INFORMATION FOR MODULATORY USE:

library source:
gi\|10725490\| adult adrenal gland
gi\|10947399\| mammary gland
gi\|9121897\| retinoblastoma
gi\|13280819\| adenocarcinoma cell line
gi\|13287907\| retinoblastoma
gi\|13286505\| embryonal carcinoma, cell line
gi\|8150776\| adult uterus
gi\|5936410\| adult uterus
gi\|6888875\| adult head_neck
gi\|6888872\| adult head_neck Tissue Expression:
Human leukocyte FIGURE 1, page 2 of 4

Isoform 2:

```
   1 GGAGGATTAA TCAGTGACAG GAAGCTGCGT CTCTCGGAGC GGTGACCAGC
  51 TGTGGTCAGG AGAGCCTCAG CAGGGCCAGC CCCAGGAGTC TTTCCCGATT
 101 CTTGCTCACT GCTCACCCAC CTGCTGCTGC CATGAGGCAC CTTGGGGCCT
 151 TCCTCTTCCT TCTGGGGGTC CTGGGGGCCC TCACTGAGAT GTGTGAAATA
 201 CCAGAGATGG ACAGCCATCT GGTAGAGAAG TTGGGCCAGC ACCTCTTACC
 251 TTGGATGGAC CGGCTTTCCC TGGAGCACTT GAACCCCAGC ATCTATGTGG
 301 GCCTACGCCT CTCCAGTCTG CAGGCTGGGA CCAAGGAAGA CCTCTACCTG
 351 CACAGCCTCA TGCTTGGTTA CCAGCAGTGC CTCCTAGGGT CTGCCTTCAG
 401 CGAGGATGAC GGTGACTGCC AGGGCAAGCC TTCCATGGGC AGCTGGCCC
 451 TCTACCTGCT CGCTCTCAGA GCCAACTGGC ATGATCACAA GGGCCACCCC
 501 CACACTAGCT ACTACCAGTA TGGCCTGGGC ATTCTGGCCC TGTGTCTCCA
 551 CCAGAAGCGG GTCCATGACA GCGTGGTGGA CAAACTTCTG TATGCTGTGG
 601 AACCTTTCCA CCAGGGCCAC CATTCTGTGG ACACAGCAGC CATGGCAGGC
 651 TTGGCATTCA CCTGTCTGAA GCGCTCAAAC TTCAACCCTG GTCGGAGACA
 701 ACGGATCACC ATGGCCATCA GAACAGTGCG AGAGGAGATC TTGAAGGCCC
 751 AGACCCCCGA GGGCCACTTT GGGAATGTCT ACAGCACCCC ATTGGCATTA
 801 CAGTTCCTCA TGACTTCCCC CATGCGTGGG GCAGAACTGG AACAGCATG
 851 TCTCAAGGCG AGGGTTGCTT TGCTGGCCAG TCTGCAGGAT GGAGCCTTCC
 901 AGAATGCTCT CATGATTTCC CAGCTGCTGC CCGTTCTGAA CCACAAGACC
 951 TACATTGATC TGATCTTCCC AGACTGTCTG GCACCACGAG TCATGTTGGA
1001 ACCAGCTGCT GAGACCATTC CTCAGACCCA AGAGATCATC AGTGTCACGC
1051 TGCAGGTGCT TAGTCTCTTG CCGCCGTACA GACAGTCCAT CTCTGTTCTG
1101 GCCGGGTCCA CCGTGGAAGA TGTCCTGAAG AAGGCCCATG AGTTAGGAGG
1151 ATTCACATAT GAAACACAGG CCTCCTTGTC AGGCCCCTAC TTAACCTCCG
1201 TGATGGGGAA AGCGGCCGGA GAAAGGGAGT CTGGCAGCT TCTCCGAGAC
1251 CCCAACACCC CACTGTTGCA AGGTATTGCT GACTACAGAC CCAAGGATGG
1301 AGAAACCATT GAGCTGAGGC TGGTTAGCTG GTAGCCCCTG AGCTCCCTCA
1351 TCCCAGCAGC CTCGCACACT CCCTAGGCTT CTACCCTCCC TCCTGATGTC
1401 CCTGGAACAG GAACTCGCCT GACCTGCTG CCACCTCCTG TGCACTTTGA
1451 GCAATGCCCC CTGGGATCAC CCCAGCCACA AGCCCTTCGA GGGCCCTATA
1501 CCATGGCCCA CCTTGGAGCA GAGAGCCAAG CATCTTCCCT GGGAAGTCTT
1551 TCTGGCCAAG TCTGGCCAGC CTGGCCCTGC AGGTCTCCCA TGAAGGCCAC
1601 CCCATGGTCT GATGGGCATG AAGCATCTCA GACTCCTTGG CAAAAAACGG
1651 AGTCCGCAGG CCGCAGGTGT TGTGAAGACC ACTCGTTCTG TGGTTGGGGT
1701 CCTGCAAGAA GGCCTCCTCA GCCCGGGGGC TATGGCCCTG ACCCCAGCTC
1751 TCCACTCTGC TGTTAGAGTG GCAGCTCCGA GCTGGTTGTG GCACAGTAGC
1801 TGGGGAGACC TCAGCAGGGC TGCTCAGTGC CTGCCTCTGA CAAAATTAAA
1851 GCATTGATGG CCTGTGAAAA AAAAAAAAAA AAAAAAAAAA AAAAAA
```

(SEQ ID NO:2)

FEATURES:

5'UTR:        1 - 131
Start Codon:  132
Stop Codon:   1332
3'UTR:        1335

Homologous proteins:
Top 10 BLAST Hits

|  | Score | E |
|---|---|---|
| CRA\|108000024636236 /altid=gi\|298316 /def=gb\|AAB25526.1\| transc... | 793 | 0.0 |
| CRA\|108000024653390 /altid=gi\|12742775 /def=ref\|XP_009922.2\| tr... | 793 | 0.0 |
| CRA\|18000004926133 /altid=gi\|339205 /def=gb\|AAA61057.1\| (L02648... | 792 | 0.0 |
| CRA\|108000024042036 /altid=gi\|12654675 /def=gb\|AAH01176.1\|AAH01... | 792 | 0.0 |
| CRA\|18000004926130 /altid=gi\|4507409 /def=ref\|NP_000346.1\| tran... | 788 | 0.0 |
| CRA\|18000004926132 /altid=gi\|339203 /def=gb\|AAA61056.1\| (L02647... | 786 | 0.0 |
| CRA\|18000005170902 /altid=gi\|7657639 /def=ref\|NP_056564.1\| tran... | 561 | e-159 |
| CRA\|164000136745249 /altid=gi\|11968124 /def=ref\|NP_071979.1\| tr... | 554 | e-156 |

FIGURE 1, page 3 of 4

| | | |
|---|---|---|
| CRA\|18000005218941 /altid=gi\|4572454 /def=gb\|AAD23829.1\|AF12128... | 545 | e-154 |
| CRA\|18000004926134 /altid=gi\|4507407 /def=ref\|NP_001053.1\| tran... | 128 | 1e-28 |

EST:

| | | |
|---|---|---|
| gi\|10725490 /dataset=dbest /taxon=96... | 858 | 0.0 |
| gi\|5936410 /dataset=dbest /taxon=9606 ... | 835 | 0.0 |
| gi\|6888875 /dataset=dbest /taxon=9606... | 726 | 0.0 |
| gi\|6888872 /dataset=dbest /taxon=9606... | 726 | 0.0 |
| gi\|12258937 /dataset=dbest /taxon=960... | 686 | 0.0 |
| gi\|10947399 /dataset=dbest /taxon=96... | 680 | 0.0 |
| gi\|13287907 /dataset=dbest /taxon=96... | 680 | 0.0 |
| gi\|9121897 /dataset=dbest /taxon=9606... | 680 | 0.0 |
| gi\|13280819 /dataset=dbest /taxon=96... | 680 | 0.0 |
| gi\|8150776 /dataset=dbest /taxon=960... | 656 | 0.0 |

EXPRESSION INFORMATION FOR MODULATORY USE:

library source:
gi|10725490| adult adrenal gland
gi|5936410| adult uterus
gi|6888875| adult head_neck
gi|6888872| adult head_neck
gi|12258937| adult lung_tumor
gi|10947399| mammary gland
gi|13287907| retinoblastoma
gi|9121897| retinoblastoma
gi|13280819| adenocarcinoma cell line
gi|8150776|

Tissue Expression:
Human hippocampus

FIGURE 1, page 4 of 4

Isoform 1:
```
  1 MRHLGAFLFL LGVLGALTEM CEIPEMDSHL VEKLGQHLLP WMDRLSLEHL
 51 NPSIYVGLRL SSLQAGTKED LYLHSLKLGY QQCLLGSAFS EDDGDCQGKP
101 SMGQLALYLL ALRANCEFVR GHKGDRLVSQ LKWFLEDEKR AIDTAAMAGL
151 AFTCLKRSNF NPGRRQRITM AIRTVREEIL KAQTPEGHFG NVYSTPLALQ
201 FLMTSPMRGA ELGTACLKAR VALLASLQDG AFQNALMISQ LLPVLNHKTY
251 IDLIFPDCLA PRVMLEPAAE TIPQTQEIIS VTLQVLSLLP PYRQSISVLA
301 GSTVEDVLKK AHELGGFTYE TQASLSGPYL TSVMGKAAGE REFWQLLRDP
351 NTPLLQGIAD YRPKDGETIE LRLVSW
```
(SEQ ID NO:3)

FEATURES:
Functional domains and key regions:
PDOC00005 PS00005 PKC_PHOSPHO_SITE
Protein kinase C phosphorylation site
Number of matches: 2
    1     75-77     SLK
    2    174-176    TVR PDOC00006 PS00006 CK2_PHOSPHO_SITE
Casein kinase II phosphorylation site
Number of matches: 6
    1     67-70    TKED
    2     90-93    SEDD
    3    174-177   TVRE
    4    226-229   SLQD
    5    249-252   TYID
    6    302-305   STVE PDOC00008 PS00008 MYRISTYL
N-myristoylation site
Number of matches: 7
    1     12-17    GVLGAL
    2     57-62    GLRLSS
    3     86-91    GSAFSE
    4    149-154   GLAFTC
    5    190-195   GNVYST
    6    209-214   GAELGT
    7    230-235   GAFQNA PDOC00009 PS00009 AMIDATION
Amidation site
        162-165   PGRR SignalP results:

| Measure | Position | Value | Cutoff | Conclusion |
|---|---|---|---|---|
| max. C | 19 | 0.602 | 0.37 | YES |
| max. Y | 19 | 0.702 | 0.34 | YES |
| max. S | 5 | 0.974 | 0.88 | YES |
| mean S | 1-18 | 0.949 | 0.48 | YES |

Most likely cleavage site between pos. 18 and 19: ALT-EM

BLAST Alignment to Top Hit:
```
>CRA|108000024636236 /altid=gi|298316 /def=gb|AAB25526.1|
        transcobalamin II, TC II [human, endothelial cells,
        Peptide, 427 aa] /org=human /taxon=9606 /dataset=nraa
        /length=427
        Length = 427

Score =  732 bits (1870), Expect = 0.0
Identities = 376/427 (88%), Positives = 376/427 (88%), Gaps = 51/427 (11%)
Frame = +1
```

FIGURE 2, page 1 of 4

```
Query:   31   MRHLGAFLFLLGVLGALTEMCEIPEMDSHLVEKLGQHLLPWMDRLSLEHLNPSIYVGLRL  210
              MRHLGAFLFLLGVLGALTEMCEIPEMDSHLVEKLGQHLLPWMDRLSLEHLNPSIYVGLRL
Sbjct:    1   MRHLGAFLFLLGVLGALTEMCEIPEMDSHLVEKLGQHLLPWMDRLSLEHLNPSIYVGLRL   60

Query:  211   SSLQAGTKEDLYLHSLKLGYQQCLLGSAFSEDDGDCQGKPSMGQLALYLLALRANCEFVR  390
              SSLQAGTKEDLYLHSLKLGYQQCLLGSAFSEDDGDCQGKPSMGQLALYLLALRANCEFVR
Sbjct:   61   SSLQAGTKEDLYLHSLKLGYQQCLLGSAFSEDDGDCQGKPSMGQLALYLLALRANCEFVR  120

Query:  391   GHKGDRLVSQLKWFLEDEKRAI---------------------------------------  456
              GHKGDRLVSQLKWFLEDEKRAI
Sbjct:  121   GHKGDRLVSQLKWFLEDEKRAIGHDHKGHPHTSYYQYGLGILALCLHQKRVHDSVVDKLL  180

Query:  457   --------------DTAAMAGLAFTCLKRSNFNPGRRQRITMAIRTVREEILKAQTPEGHF  597
                            DTAAMAGLAFTCLKRSNFNPGRRQRITMAIRTVREEILKAQTPEGHF
Sbjct:  181   YAVEPFHQGHHSVDTAAMAGLAFTCLKRSNFNPGRRQRITMAIRTVREEILKAQTPEGHF  240

Query:  598   GNVYSTPLALQFLMTSPMRGAELGTACLKARVALLASLQDGAFQNALMISQLLPVLNHKT  777
              GNVYSTPLALQFLMTSPMRGAELGTACLKARVALLASLQDGAFQNALMISQLLPVLNHKT
Sbjct:  241   GNVYSTPLALQFLMTSPMRGAELGTACLKARVALLASLQDGAFQNALMISQLLPVLNHKT  300

Query:  778   YIDLIFPDCLAPRVMLEPAAETIPQTQEIISVTLQVLSLLPPYRQSISVLAGSTVEDVLK  957
              YIDLIFPDCLAPRVMLEPAAETIPQTQEIISVTLQVLSLLPPYRQSISVLAGSTVEDVLK
Sbjct:  301   YIDLIFPDCLAPRVMLEPAAETIPQTQEIISVTLQVLSLLPPYRQSISVLAGSTVEDVLK  360

Query:  958   KAHELGGFTYETQASLSGPYLTSVMGKAAGEREFWQLLRDPNTPLLQGIADYRPKDGETI 1137
              KAHELGGFTYETQASLSGPYLTSVMGKAAGEREFWQLLRDPNTPLLQGIADYRPKDGETI
Sbjct:  361   KAHELGGFTYETQASLSGPYLTSVMGKAAGEREFWQLLRDPNTPLLQGIADYRPKDGETI  420

Query: 1138   ELRLVSW 1158
              ELRLVSW
Sbjct:  421   ELRLVSW 427
(SEQ ID NO:6)
```

HMM results:

| Model | Description | Score | E-value | N |
|---|---|---|---|---|
| PF01122 | Eukaryotic cobalamin-binding protein | 829.9 | 8.6e-246 | 2 |
| CE00052 | CE00052 lymphocyte_transmembrane_protein_KAP | 3.2 | 2.9 | 1 |

Parsed for domains:

| Model | Domain | seq-f | seq-t | hmm-f | hmm-t | score | E-value |
|---|---|---|---|---|---|---|---|
| CE00052 | 1/1 | 1 | 11 [. | 1 | 11 [. | 3.2 | 2.9 |
| PF01122 | 1/2 | 1 | 142 [. | 1 | 143 [. | 296.0 | 4.6e-85 |
| PF01122 | 2/2 | 143 | 376 .] | 197 | 450 .] | 531.8 | 4.8e-156 |

FIGURE 2, page 2 of 4

Isoform 2:

```
  1 MRHLGAFLFL LGVLGALTEM CEIPEMDSHL VEKLGQHLLP WMDRLSLEHL
 51 NPSIYVGLRL SSLQAGTKED LYLHSLMLGY QQCLLGSAFS EDDGDCQGKP
101 SMGQLALYLL ALRANWHDHK GHPHTSYYQY GLGILALCLH QKRVHDSVVD
151 KLLYAVEPFH QGHHSVDTAA MAGLAFTCLK RSNFNPGRRQ RITMAIRTVR
201 EEILKAQTPE GHFGNVYSTP LALQFLMTSP MRGAELGTAC LKARVALLAS
251 LQDGAFQNAL MISQLLPVLN HKTYIDLIFP DCLAPRVMLE PAAETIPQTQ
301 EIISVTLQVL SLLPPYRQSI SVLAGSTVED VLKKAHELGG FTYETQASLS
351 GPYLTSVMGK AAGEREFWQL LRDPNTPLLQ GIADYRPKDG ETIELRLVSW
```
(SEQ ID NO:4)

FEATURES:

Functional domains and key regions:
PDOC00005 PS00005 PKC_PHOSPHO_SITE
Protein kinase C phosphorylation site
        198-200        TVR PDOC00006 PS00006 CK2_PHOSPHO_SITE
Casein kinase II phosphorylation site
Number of matches: 7
| | | |
|---|---|---|
| 1 | 67-70 | TKED |
| 2 | 90-93 | SEDD |
| 3 | 147-150 | SVVD |
| 4 | 198-201 | TVRE |
| 5 | 250-253 | SLQD |
| 6 | 273-276 | TYID |
| 7 | 326-329 | STVE |

PDOC00008 PS00008 MYRISTYL
N-myristoylation site
Number of matches: 7
| | | |
|---|---|---|
| 1 | 12-17 | GVLGAL |
| 2 | 57-62 | GLRLSS |
| 3 | 86-91 | GSAFSE |
| 4 | 173-178 | GLAFTC |
| 5 | 214-219 | GNVYST |
| 6 | 233-238 | GAELGT |
| 7 | 254-259 | GAFQNA |

PDOC00009 PS00009 AMIDATION
Amidation site
        186-189        PGRR

PDOC00428 PS00468 COBALAMIN_BINDING
Eukaryotic cobalamin-binding proteins signature
        165-178        SVDTAAMAGLAFTC

SignalP results:
| Measure | Position | Value | Cutoff | Conclusion |
|---|---|---|---|---|
| max. C | 19 | 0.602 | 0.37 | YES |
| max. Y | 19 | 0.702 | 0.34 | YES |
| max. S | 5 | 0.974 | 0.88 | YES |
| mean S | 1-18 | 0.949 | 0.48 | YES |

Most likely cleavage site between pos. 18 and 19: ALT-EM

BLAST Alignment to Top Hit:
```
>CRA|108000024636236 /altid=gi|298316 /def=gb|AAB25526.1|
       transcobalamin II, TC II [human, endothelial cells,
       Peptide, 427 aa] /org=human /taxon=9606 /dataset=nraa
       /length=427
       Length = 427
```

FIGURE 2, page 3 of 4

```
Score = 793 bits (2026), Expect = 0.0
Identities = 399/427 (93%), Positives = 399/427 (93%), Gaps = 27/427 (6%)

Query:   1 MRHLGAFLFLLGVLGALTEMCEIPEMDSHLVEKLGQHLLPWMDRLSLEHLNPSIYVGLRL  60
           MRHLGAFLFLLGVLGALTEMCEIPEMDSHLVEKLGQHLLPWMDRLSLEHLNPSIYVGLRL
Sbjct:   1 MRHLGAFLFLLGVLGALTEMCEIPEMDSHLVEKLGQHLLPWMDRLSLEHLNPSIYVGLRL  60

Query:  61 SSLQAGTKEDLYLHSLMLGYQQCLLGSAFSEDDGDCQGKPSMGQLALYLLALRAN-----  115
           SSLQAGTKEDLYLHSL LGYQQCLLGSAFSEDDGDCQGKPSMGQLALYLLALRAN
Sbjct:  61 SSLQAGTKEDLYLHSLKLGYQQCLLGSAFSEDDGDCQGKPSMGQLALYLLALRANCEFVR 120

Query: 116 ------------W----------HDHKGHPHTSYYQYGLGILALCLHQKRVHDSVVDKLL 153
                       W           HDHKGHPHTSYYQYGLGILALCLHQKRVHDSVVDKLL
Sbjct: 121 GHKGDRLVSQLKWFLEDEKRAIGHDHKGHPHTSYYQYGLGILALCLHQKRVHDSVVDKLL 180

Query: 154 YAVEPFHQGHHSVDTAAMAGLAFTCLKRSNFNPGRRQRITMAIRTVREEILKAQTPEGHF 213
           YAVEPFHQGHHSVDTAAMAGLAFTCLKRSNFNPGRRQRITMAIRTVREEILKAQTPEGHF
Sbjct: 181 YAVEPFHQGHHSVDTAAMAGLAFTCLKRSNFNPGRRQRITMAIRTVREEILKAQTPEGHF 240

Query: 214 GNVYSTPLALQFLMTSPMRGAELGTACLKARVALLASLQDGAFQNALMISQLLPVLNHKT 273
           GNVYSTPLALQFLMTSPMRGAELGTACLKARVALLASLQDGAFQNALMISQLLPVLNHKT
Sbjct: 241 GNVYSTPLALQFLMTSPMRGAELGTACLKARVALLASLQDGAFQNALMISQLLPVLNHKT 300

Query: 274 YIDLIFPDCLAPRVMLEPAAETIPQTQEIISVTLQVLSLLPPYRQSISVLAGSTVEDVLK 333
           YIDLIFPDCLAPRVMLEPAAETIPQTQEIISVTLQVLSLLPPYRQSISVLAGSTVEDVLK
Sbjct: 301 YIDLIFPDCLAPRVMLEPAAETIPQTQEIISVTLQVLSLLPPYRQSISVLAGSTVEDVLK 360

Query: 334 KAHELGGFTYETQASLSGPYLTSVMGKAAGEREFWQLLRDPNTPLLQGIADYRPKDGETI 393
           KAHELGGFTYETQASLSGPYLTSVMGKAAGEREFWQLLRDPNTPLLQGIADYRPKDGETI
Sbjct: 361 KAHELGGFTYETQASLSGPYLTSVMGKAAGEREFWQLLRDPNTPLLQGIADYRPKDGETI 420

Query: 394 ELRLVSW 400
           ELRLVSW
Sbjct: 421 ELRLVSW 427
(SEQ ID NO:7)
```

HMM results:

| Model | Description | Score | E-value | N |
|---|---|---|---|---|
| PF01122 | Eukaryotic cobalamin-binding protein | 906.3 | 8.6e-269 | 2 |
| CE00052 | CE00052 lymphocyte_transmembrane_protein_KAP | 3.2 | 2.9 | 1 |

Parsed for domains:

| Model | Domain | seq-f | seq-t | hmm-f | hmm-t | score | E-value |
|---|---|---|---|---|---|---|---|
| CE00052 | 1/1 | 1 | 11 [. | 1 | 11 [. | 3.2 | 2.9 |
| PF01122 | 1/2 | 1 | 115 [. | 1 | 115 [. | 241.3 | 1.4e-68 |
| PF01122 | 2/2 | 117 | 400 .] | 145 | 450 .] | 660.5 | 8.7e-195 |

FIGURE 2, page 4 of 4

```
   1 ATATGTATGG GAAATATGCT GTCTTCCTAT TCCTACTCCC CCACCCTCTA
  51 GCACTGAGTC CAGGTAGGTA GGCAGGGGGG TGTCTCCCTC CTTTACTTCG
 101 ACACCCTAAC TACCTTGGGG ATCAGAAGTG ACTCTCTGGA AGGATGCTGC
 151 TGCTTCTCAC CAGAGGCTGA CGATAACGAA GGCTATCCTC CATGGCCACC
 201 TCCTCCAGGC TGCCTTCCTG GAAATAGGAA TCATAATAGT TGTTACTGGA
 251 AACAGGCAGA GGGTTGGGGG AGCCAAGGCA GTCCCACCCA GGACCAAGGT
 301 GGCTCCATTG CACACACTTC ACCATGACTC CCCTGAAGGT CCAAACGTGC
 351 GGTTCTGCGG AAGTTGGGCT CCCCACTGGC CTCCCTCCTT CCTCAGAACC
 401 TCCAGGGGTG CTCCTCCTAG TGGCCACATC CAGCCTTTCT GACTGGACAA
 451 CCTATCATTT AAAATTTTCA AGTAGTTCCG TAAACAGACA CACGTTGCTG
 501 TATTTATTTA TGTCAAGGGC TTGGTTTGTG ATAAGTCAGG CTCAAAAAGA
 551 TTGTCTTAAA AGAGTGAACC TTGGCAATTT ACCATAAAAT AATTGCAATG
 601 CAGATTGTGC ATGGAAATGA TTGGAGATAT TTTAAGGTCA TAGTGTCTTC
 651 ACAAATTGAG CTGAAAGGGA ACTGTTAGGA TGATCTTGCC TAACCCTCTC
 701 ATCTCACACA GGAAGAACTA TTTTAAACTC GAGAGGTTAA GTGACCTGGC
 751 CAAAGTCACA CAGCCACCAC TAGTTAACTC GTATACATTG ATTCTCCTGT
 801 GGGGCTGGGC AGATGAGGAA TCTTTTGTTC TCTTCCCTGT TTGCAGAGAT
 851 TTTTTTTGAG GTTACTTTCC GAGTTCTGGC AAGTACCCCT GCTTCTGGTA
 901 GCTTTGTGTC TCGATTCAAT CTCATTCTTT TTATTTTATT TTATTTTTGA
 951 GACAGGGTCT CACTTTGTCA CCCAAGCTGG AGTGCAGTGG TGTAATCTTG
1001 GCTCACTGTA GCCTCCACCT CTTGGGTTCA AGCGATCCTC CTGCCTCAGC
1051 CCCCCAAGTA GCTGGGATTA CAGACGTCTG CCACCACGCC AGGCTAATTT
1101 ATGGTTTTTT GTATGTGTTT TTGTGTTTT TGTAGAGACA GTGTTTCCCC
1151 ATGTTGCCCA GGCTGGTCTC CAACTCCTGA GCTCAAGTGA TCTGCCCGCC
1201 TCAGCCTTTC AAAGTGCTAG GATTACAGGT GTGAGCCACC GTGCCCGGAC
1251 TTAATCCCAT TCTTTAACTT GTTTTGTTTT GTCCTCTCCA GGAGGCTCCC
1301 AGCCCTTTCG GATTGGTTGA GAAAAGTGGC CTGGCTGGTC TGGGGCCAGC
1351 AGCACCCACC CTCCCCTCAA TTGCCCAACT CCCCCCCCCA CCGAACTGCC
1401 CAACTCCCCC TCCCCAACTG CCCAACTCCC CCACCCCCAC AATCCCTCC
1451 CGCCACAACT GAGGGAGGCG GTGCTGAAAA ACAGCTGACT CCAGCAATGC
1501 TGCTCACGTG ACCACTGCAG CTGCAGCTCC CGTTCCACTC CTTGTCCTGG
1551 GCTAGGTGGG CACTACCAGG GGCTCCTTTG GTAAGGAGTA CCGGGTAGGC
1601 ACCCGGTCCT GCCAATCCAC CACTGGAACA GCTGGGGGGA CAGCAGACAG
1651 GCACGGTCGG ACAGACTTGA CAGATCAGGC ATCAGGCCCT CTGCGCTGGT
1701 CCCGGGCTCT TTAAGCAGGA ACGTGAATGG CCTCAAGATG TCTCACATGG
1751 TCCCACTAGC CCTCCTCCTC CCTTTGTTCC CTACCTCCAG GAGGGCTGCT
1801 CTGCCCTTCC TTCCTCTGTT CTTTGGCCTT ATGTTCCCCG CCACCACAGG
1851 CCTTCCCCCG CCCCACCCCT CTGCAGACTT AGCCGTGCAT TGCAGGCATG
1901 GAGGATTAAT CAGTGACAGG AAGCTGCGTC TCTCGGAGCG GTGACCAGCT
1951 GTGGTCAGGA GAGCCTCAGC AGGGCCAGCC CCAGGAGTCT TTCCCGATTC
2001 TTGCTCACTG CTCACCCACC TGCTGCTGCC ATGAGGCACC TTGGGGCCTT
2051 CCTCTTCCTT CTGGGGGTCC TGGGGGCCCT CACTGAGATG TGTGGTGAGT
2101 AACTCGCCTC TATCCTGTGC CTCTTTCCTC CTGGGTCCTT AGTGGGGTGG
2151 CTAGGGCATA GGATGAGGGA ACTTACCTGC CCTTCTAAGC TCCCATAGCA
2201 GTTTGGGCTT AGCTGGACCT CAGCATTTAA CACATCCTAT TGTGATTGAT
2251 TATATGTTTG ACTCCTCACC AGACAAGATC TCCGTTAATT CAGTCATTCG
2301 TTCACACATT CATTCAGCGC ATACTGAGCC TTTTCTGTGT CAGGCCCAGT
2351 GTTAGCCTTT GGGGAACGTG CAAAGCATGA GACAAGTCTA ATCCCTGCCA
2401 TCCTAGAGCT TATGTTCTAG GGAAGGGGGA CAGACAAAAG AAATGGTTAG
2451 GTGCTCCCAC CTGAAATCTC AGCATTTTGG AAGGCTGAGG CGGGAGGGGA
2501 GGATCGCTTG AGCTCAACAG TTCAAGGTCA GCCTGGGCAA CATAGGGAGA
2551 CCCCATCTCT ACAAAAAATA AAAAAAATTA AAAAATAGCT GGGCATGGGG
2601 AAGACTTTCT GAAGACCAAG AGGACACATG GGAGCTGAAA CTCGAAGGAA
2651 GAAAAGGAGC TGGCAGGAAA GGAGTGGGGG ACACACATTC TAGGCAGCAG
2701 GAAGTGAGCC TTCGGAGGTC CTGCCTGCTC CAGCTCTGTG CCCCAAGGGG
2751 TCTCTTGGAG CACAGTCTCC TGGGACCTGT CTATGAGTCT GAGCTTAGAG
2801 GCTCAGGGCT GCTCCTTCAG ACAGGAGGCA GAAGGCAGAC TTTGGGAACT
2851 TTGGGCCGCC CACGCGCCTT TTCTCCTCCT CTGCACCTAG GATTACGTTG
2901 AGCAATACAC TTTCACCCCC ATGGTCTCTT GAGACCCTGG GGAAACCCTG
2951 AGAGGTGGGT GCAGTCATGT CCAGGTGTCA AGTGAAGAAG TCGAGGGTTG
3001 GAGGGGCTGA GTGACCCACT CAGGGTGCTC CACCTTTTCC AGAGCTTTGC
3051 TGAACTTAGT TTTTAGAACT TGAAGCCTCG TTTGTTTTCG TTTTGTTTTT
3101 TGTTGAGAGA GGTTCTCCCT CTGTTGCCCA GGCTGGAGTG CAGTGGCACG
3151 ATCTTGGCTC ACTGCAGCCT CTGCCTTGTG GGTTCAAGTG ATTCCCCAC
3201 CTCAGCCTCC CAAGTAGCTG GAGACTGCAT GTGCATACTA CCATGCTTGG
3251 CTAATTTTTG TATTTTTTG TAGAGACAGG GTTTCGCCAT GTTGCCCAGG
3301 CTGGTCTCGA ACTCCTGGGC TCAAGTGAAA CTCTTGCCTC GGCCTCCCAA
3351 ATTGCTGAGA TTACAGGCGT GAGCCACCGT GCCCGGCCAG AACTCCAAGC
3401 CTCTCATCTG TGTTCCATAA ATGCAATCAG ACACCTCAGG TCTGGCCCA
3451 GGAACCCCAG CTCTTGGTTC ATGTCCGGAC AGTCCCCAGG GGAGTTCTGG
3501 GTTCAACCAG CAAGAGCTCT TCCTCCTGGC TGATCTGGTC CTCAGCCTTG
```

FIGURE 3, page 1 of 22

```
3551 GACAGTTAGT CCATTAACCT GACCCCACAG GAGCCCCAAT CCCTTGGGGT
3601 CTGGGGAATC TTGAACTGGG GTTTGGGGTG CAAATATCTG CACTGAGTCA
3651 CTTAATTGCA CCCAGCCTCA TTCCTTTATC TGTAAAGTGG GCTAAGAATG
3701 CTCCCCTGCC TTCCTCCTCG GTGTAGTACG AGGAAGGATC CCATGACACC
3751 TGCTCTCCCA GTTTAAAGCT CTATATGTAT GTTGTGAAAT TGACAGGGAT
3801 CGCTGCACAA ACGCTAATGC AAAGTGGGCT CCTGTGCTTC CTTTTCTCTT
3851 TCTTCTTCTT TTTTTTTTTT TTAATTTTCT TCTAGAGATG AGGTCTCACT
3901 ATATTGCCCA GGGTTGGTTT CAAACTCCTA GGGTCAAGCG ATCCTCCCAC
3951 CTTGGCCTCC CAAACTGCTG GTATTACAGG CGTGAGCCAC TCTGTCTGGC
4001 TCCTATGCTT GTGAATGTCA ACAGCAATCA GCCCTTAGCT GGCAGGGCTG
4051 GGTTGGTAGG GCGAGAGCTC ACCCAAGGCT GCTTTTATTA CCCTGCGTGA
4101 ATCTGCCTGG CCCCTTCCTT CTAAGGAGGT TGCTCTGTGG TTGTCAGTCT
4151 CTCCCTTTAC AGCTGGATCC TGATCTTTCA GTTTCTAACC CTGTGCTGAC
4201 TCATCGTGCT GGAAGTGAGA GCCCGGGGTG AGGTCAGGGA ACTCCCTTGC
4251 GCGTTTCAAG AAAAGGGAAA AGGAAAGAGA GGTGAGGAGG GGGGCAGATG
4301 ACCAGAGAGA CACAGGCTGA GAGAGACTGA GACAGACCCA GAGAGCCTCA
4351 CACATTGAGT GACAGAGACG GAGAAATGGA GATAGGCACC AAAAAATGGT
4401 TCTCAGTGAC AGAAAGGGAA AAAAGCAACC CCCCAGTCTC TCTTAACATC
4451 TGGTGAGAAA CCAGCCATGT GCTTTGGTCT GGGCCCACAC AGCAAAGGAT
4501 TATGTAGGGT TTCATGCTGG TGGATGGTCA CCTTATAGCA ACAGGTATCT
4551 GGGGCTGTCG GGAAAACAGA CACGAGGTTG TGGGACCCAG ACCCACAGAG
4601 ATGGAGCTGT TCTAGGAGCT CTGGTCCTCG TTCTGGTCCC CTGGGATATG
4651 GCACAGTGAA GGCCACCATC AGGCAGCTGG AGCCCAGCAG CAACTGGGAG
4701 GCAGTAAACA GGGACCGAAA GTGCAAGGTT ACCTCCGAGG CAAACTACTC
4751 TAAGCTACCC TGTGCTGAGC TCAAGTCCCT TGGAACTATC CCTAAGGCTT
4801 CCGCTTCCAG AGTGTTTGAG TATTTTCGTT GCACAGCTTC GAATAAATCC
4851 CACAGCAACA GGTAAACGGC TGCAAGCTGT GACTGTTTTC TAAGAGCTCA
4901 TCTCACAATC TCAGGTCCTC TTCATTTAAA CAGAGATGGC AGGAAAGGCG
4951 TTATTTTGAG ATCTCATGG AGGAAGTTCA CCAGGCAGCC TCAATTCACC
5001 AGCTGGAAGT TTGCGTTGTT TGGAAATTTG ATGTGTAACA CGTTCTGCAT
5051 GTGGGCTGAT GTTTTTGTAA ACGGGTAGCA CACACATTCA GCAGGGCACC
5101 AAAGAGCGGG GGCTTTGCAG TTAGGTCCAT CCTTGGCTCT GCAGCCTTGT
5151 GTAAGACATG ACACGACTTT GAACTTCTGT TTCCTCTTCT GTGCAAAGCA
5201 ATGATGCAG TATCTACATC ACAGGACTGG CATGAGGACC AAGTGAGATT
5251 GGGCAAGGTG CCCGGGCACA CCAGTCTCAC TGTCACTGCT GATGGGCAGA
5301 GTGGTTGCCT GGCAGTAGCA TCCTCTATCT TCAGCCCACC ACCTCTCTTG
5351 CTGGCTCACT CCAACTGCTC TTTAGAGATA CACGCTTCCC CTCTTTTCTC
5401 CTCCCACTGC CTTTCAGTAT GGCTGCATTT CCCCCTGCAA GTTGGTGTGT
5451 GCTGGGTGGA GGTGGGGGTG AGGACATGTA TTCTCTGGAG AAGGCCCTGG
5501 TAACGTCAAA GCACTTCTTT GCTGGTGGCC TGGCCCTGTG ACCTCATTTG
5551 TACCATTTTC TTTTCTAAGA AATACCAGAG ATGGACAGCC ATCTGGTAGA
5601 GAAGTTGGGC CAGCACCTCT TACCTTGGAT GGACCGGCTT TCCCTGGAGC
5651 ACTTGAACCC CAGCATCTAT GTGGGCCTAC GCCTCTCCAG TCTGCAGGCT
5701 GGGACCAAGG AAGACCTCTA CCTGCACAGC CTCAAGCTTG GTTACCAGCA
5751 GTGCCTCCTA GGGTATTGCC ACACTCTCTT TTTCCATGTC TTGCTCCACA
5801 TACTAAGAGA TGGGAAACTT GGGTACTAGT TTGGGCCTGT CACCACTTTG
5851 TGGGCAGACC TTAGGCAAAT TTTCTCCATC TATAGAATGG AGGACCTTTG
5901 TCCATCTATA GAATGAAGGG GTTGGTTGGA TTAGATCAGA GATGCTAATG
5951 CAAGGCTCCT TTTGCTACTA CTGTCCATCA TGTGTCTGAG GCAGACATAA
6001 CTAATCCGTG ACTATACTCT TTGATGATGA GCCCAGGAGC AGCATCTGAC
6051 TCTATGCTCC CTTAGTGTGC CTGAGGCAGA TATCACTAAT CGATGACTGC
6101 AGTCTTCTAC ATTGAGCTTA GAAGCAGCAT CTGACTCTGT ATGCTCCCCT
6151 CCCATGCATG AGGCAGACAT CAGTAATCCA TGACCGCATT CTTTCATACT
6201 GAGCCCAGAA GCAGCATCTT TTCTTTTCTT TCCTCTCACT CTGTTGCCCA
6251 CGCTAGAGTG CAGTGGCACA ATCTTGGCTT GCCCCAACCT CCAATTCCCG
6301 GGTTCAAGTG ATTCTCGTGC CTCAGCCACC TGAATAGCTG GGATTACAGG
6351 CGTGTGCCAC CATGCCCAGC TGATTTTTGT ATTTTTGGTA GAGATAGGGT
6401 TTCACCATGT TGGCCAGGCT GGTCTTGAAC TCCTGACCTC AGGTGATCCG
6451 CCTGTCTTGG CTTCCCAAAG TGTTGGGATT ATAGGCATGA GCCACTGCAC
6501 CAATCCAAAA GCAGCATCTT TGTGCTCCCT TTTCAAGAGG CATCACAGAG
6551 AGGCCTGTTT TGGGGTTTGA ATGAGAGGCG AAGAATCAGC CATGGAGTGC
6601 CTCTTTCTCA GACTCCCTCT TGAGAAGTGG GTGCAGGGGT GGAGAGAAAA
6651 GAAGACTAGG CATAGTGGCT CATACCTGTA ATCCCAACAT TTTGGGAGGC
6701 TGAGGCAGGA AGATTGCTTG AGCTCAGGAG TTTGAGACCA GCCTAGGCAA
6751 CATAGTGAGA CCACATCTCT TAAAAAAAAG AAAAAGAAAA AAAATGAGCC
6801 AGGTGTAGTG ACTCATGCCT GTGGTCCCCA CTTCTCCGGA GGCAAAGGTG
6851 GGAGGATCTT TTGAGGCTGA GAAATCGAGG CTACAGTGAG CCATGGTGGC
6901 ACCACTGCAC TCCAGCCTGG GAGACAGAGA GACCCTATCT CAGTAAAAAA
6951 AAAAAATAAA AATATGCTG GGTGTGGTGG CTCACGCCTG TAATCCCAGC
7001 ACTTTGGGAG GCCAAGGTAG GTAGATCACA TGAGGTTAGG AGTTCGAAAC
7051 CAGTCTGGCC AACATAGTGA AACCCTGTCT CTACTGAAAA TACAAAAAAT
```

FIGURE 3, page 2 of 22

```
7101 TAGCCAAGGG TGGTGGTGGG CAACTGTAAT CCCAGCTACT TGGGAGGCCG
7151 AGGCAGAAGA ATCGCTTGAA CTCGGGAGGC GGAGGTTGCA GTGAGCTGAG
7201 AACATGCCAC TGCACTCCAG CCTGGGCAAC AAGAGCGAAA CTCTGTCTCA
7251 AAGAAAATAA ATAAATAAAA TAAAAAAATA AAAAAGGAGG GGGCATATGG
7301 GTGAAGTATG GACAAAATAG TGGGGCAGGC ACAGATGATC TGGACACAGG
7351 AGCCCTTGGA GTTTATTCTT GAATCTAACT GTTCATCTTT ATTAAATATT
7401 TGTGGCATAC ACCTCACAAC AACATAGCCA ACACACCTCC TTTTGGAGCT
7451 TTTATCGAAG TTTCCCACTG TTAAGATTTT TTCCCGCTTT GTGATGCGGG
7501 TGGGGTGGGT GCTGTAAGCA GGCTTACGGG GTGGCAGTTT CTCACAAAGG
7551 CATTAACTGG CCTTGTCCTA GGTCTGCCTT CAGCGAGGAT GACGGTGACT
7601 GCCAGGGCAA GCCTTCCATG GGCCAGCTGG CCCTCTACCT GCTCGCTCTC
7651 AGAGCCAACT GTGAGTTTGT CAGGGGCCAC AAGGGGGACA GGCTGGTCTC
7701 ACAGCTCAAA TGGTTCCTGG AGGATGAGAA GAGAGCCATT GGTGAGCAGA
7751 CACCATCCGC TGGGGGTGGG GAGCAGCTGG GAGGGCTCAT CAGATGATAT
7801 TCTCCAATGA GAATCAGAAC TTTGGGTTTT CTCCCCAGGC GTCTTTCCCA
7851 CCATCCATTC TGCCCATCTC ACTGCCTACG TAGAGGCTCG AACCTGTCCC
7901 CATAGCCATC CTTGACCCAG CTTTTCCCGC GCTGCACACA TACTATTGAC
7951 AGGTGTGTTT CGTGGTTTTT TGTTTTTTGT TTGTTTGTTT GTTTTGAGTT
8001 GGAGGTTTGC TCTTGCTGCC CAGGCTGGAG TACAATGGCG CAATCTCAGC
8051 TCACCGCAAT CTCTGCCTCC TGGGTTCAAG CAATTCTCTT GCCTCAGCCT
8101 CCTGAGTAGC TGGGATTACA GGCATGCGCC ACCACACCCA GCTAATTTTG
8151 TATTTTTAGT AGACGTGGGG TTTCTCCATG TTGGTCAGGC TGGTCTCGAA
8201 CTCCTGACCT CAGGTGATCC GCTTGCCTTA GCCTCCGAAA GTGCTGGGAT
8251 TACAGGCATG AGCCACTGCG TTAGGCCCAC TGACAAGCCT TGTATTGGCT
8301 AGCCACCAAG ATTGACTTGA TTATCCACCT TCGGGACAAC TGGACAGCCT
8351 GCTTATGACT TACGCCATAG TCTGTCTCTA CTAGCTCTCC TGCCCTGACT
8401 TGACCCAGCA TACAACAGCC AGAGCCAGCC TTTTCAATAT AAACCTGATC
8451 TTGCTGGCAC TGCTTAAACC CTGCAGGGGC CTCGCACTGC TCCATGGCCC
8501 AGCCTGTCTA CCCTTACCTT CTGCCCAGGC TCTGCTCATC CATTCTCTGC
8551 CTCCCACACA CCTGCCCTCT GTGGGCTCCA GCCATACCAT CTCTCAACTC
8601 ATAAGCCAGT TTTTTCATAC AGGCTCCCTC CATCTGGACT GGCTTCCCTG
8651 CGTGCAGTTC ACTCCTGCTC TACCTTGGC TCTGCCTCCA CCCATCCTCA
8701 GCCGTCTCCA GCATTACCTC CTTGGAGAAT CCTGCCTTGA CTTCCCAGCC
8751 ACCCAAATAT CACTACTTGG TCTGCATTCT CGTTGCAATT GCAGTCGCAT
8801 GAGCAATTGC TGTGGTTGAG GCCCGAACTG CGCAAGTGCC TGTCTGCCAT
8851 GGGTCTCCTG CTTCCTCTAA GCACAGTGCC TGACACACAG TGAGACCTCA
8901 GCACGTATGG GCTGAGGCAA TGAAGGAATG AAGGATCCCA TGACCCAAAA
8951 GAGCCTGTTG GAAAGTGCAG GCCAGGGTCC CAGGTGCTGG CGGGGCTGGC
9001 TGCTGGGTGG GGGCAGAGAG GCAACCCCTC TGTTTTTTTC CCTCTCAGGG
9051 CATGATCACA AGGGCCACCC CCACACTAGC TACTACCAGT ATGGCCTGGG
9101 CATTCTGGCC CTGTGTCTCC ACCAGAAGCG GGTCCATGAC AGCGTGGTGG
9151 ACAAACTTCT GTATGCTGTG GAACCTTTCC ACCAGGGCCA CCATTCTGTG
9201 GGTGAGTAGG TCAGACCGTG CCAAGGCCAG GCTGGCACTC CCTCAGTCCC
9251 CAGGTCTGCA CTGATGACGT CCATACCCTG GCCCCCACAC TCACCTTTCC
9301 TTGGGGCTCC TCCGAATCAA GTCCTTTAGG GACGAATTGG CGAGGGCTCA
9351 TGGGTGATGC TCCAGCTGTG AGCCAGCTTT GGAGCTGGTA GGTGGATCTC
9401 TTGAGGCCAG GAGTTCAAGA CAACGTGGTG AAACCCCATC TCTACTAAAA
9451 ATAAAAAAGT TAGCCGGGCA TGGTGGCACA TGCCTGTAGT CCCAGCTACT
9501 CGGGAGGCTG AGGCAGGAGA ATCACTTGAA CCTGGGAGGC GGAGGCTGCA
9551 GTGAGTGGAG ATCGCACCAC TGCCCTCCAG CCTGGGCAAC AGAGTGAGTG
9601 AGACTCTGTC TCAAAAAATA AAAATAAAA TAAACTCCC CTAGTGATTC
9651 CAATGTGCAG CTAAGTTTGG AAATAGGTGG TATGGGGTCA AGTCCTCTTG
9701 GGCCTCCCTC CTCCAGTCCT TCTCCCTAAC CTCTAGCCCT CAAGTTGCAG
9751 AGTGATCAGC CAAACCAGTT TGCCCAGAAA TGAGCAGTTT CCTGGGACAC
9801 AGGATTTTCA GAGTCCAGAC AAGGAAAGTC TTGGGCAGAC CAGGTTGAGT
9851 TGGTGCCCTT AGCTGATCTG ACCATGTTGC CCTTCTTCTC CAAGCCCTCC
9901 TGTGGTTGTC CATAGCTACA AGGGCCTGAC CCTCAAGCCC CTGCCTGTCC
9951 TGGCCCCTTT GGCTCTCCAG CTCATTGCAT GTTCTGTCCC CCACTTCAAG
10001 ACACAGCAGC CATGGCAGGC TTGGCATTCA CCTGTCTGAA GCGCTCAAAC
10051 TTCAACCCTG GTCGGAGACA ACGGATCACC ATGGCCATCA GAACAGTGCG
10101 AGAGGAGATC TTGAAGGCCC AGACCCCCGA GGGCCACTTT GGGAATGTCT
10151 ACAGCACCCC ATTGGCATTA CAGGTGGGAA AGAGACCCTG GAGCCATGGC
10201 CACCCTGGGG AACAGTCGGG TGGAGTGGTC AGGTGCTGGA ACACCTAGCC
10251 CCTCCCTGCC GGCTGACCTC CTCTCTCTCT TCCTCACTCT ATCACCAGTT
10301 CCTCATGACT TCCCCCATGC CTGGGGCAGA ACTGGGAACA GCATGTCTCA
10351 AGGCGAGGGT TGCTTTGCTG GCCAGTCTGC AGGATGGAGC CTTCCAGAAT
10401 GCTCTCATGA TTTCCCAGCT GCTGCCCGTT CTGAACCACA AGACCTACAT
10451 TGATCTGATC TTCCAGACT GTCTGGCACC ACGAGGTAGC CCAACTTTTT
10501 GTGGAAGCAC AGCCCTTTAC AATCTGCTGC GCACCCATTG ACGTCCCAGT
10551 GAGGGGAGGT TGCTTCATCC TGATTTGCTG AGTCAGCACA AGTTTGTGGG
10601 TGTGCATGGG ACACAGTAGC CAAAATGTGG TCATAGCTTC TAGAAGCTCA
```

FIGURE 3, page 3 of 22

```
10651 CAGTGTGGGG AGGAAGACAG TAAATGGAGA TCCCTGGGCA TATCGCTTGT
10701 GTGATACCCA GTACAGAAAT GTTTGGATGG ATGGATGGAT GGATGGATGG
10751 ATGGATGGAT GGATGGATGG ATGAGGAGAG ACACATTTTG GTTAACTCTA
10801 ATACAACATG ATAAGCCCCA GTAGCAGCAT GATCCAGGCT TTCTCTGAGA
10851 GAGGGTCTGA GGACGTGACT GGGATTTGCC AATTAAGAAT GGAGAAAGAG
10901 GCCAGGTGCA GTGACTCATG CCTGTAATCC CAACACTTTG GGAGGCCGAG
10951 GCGGGTGGCT CACCTGAGGT CAGGAGTTCG AGACCAGCCT GGCTAACATG
11001 GCGAAACTCC ATCTATTAAA AATACAAAAA AGTAGCTGGG TGTGGTGGCG
11051 AGTGCCTGTA ACCCCAGCTA AGCTACTCAG GAGGCTGAGG CAAGAGAATC
11101 ACTTGAACCT CAGAGGTGGA GGTTGCAGTG AGCCAAGATC ATGCCACTGC
11151 ACTCCAGTCT GGGTGACAGA GTAAGACTAT GTCTCAAAAA AAAAAAAAA
11201 AAATGGAGAA GAAGGAAGCT GGACATGGTG GCTCGTGCTT ATAATCCTAG
11251 CACTCTGGGA AGCTGAGGCA GATGGATTGC CTGAGCCCAG GAGTTTGAGA
11301 CCAGCCTGGG CAACATGGTG AAACCCTGTC TTTACTAAAA TACGAAAGAT
11351 TAGCCAGGCA TGGTGGTAGA CACCTATAAT CCCAGCTACT AGGGAGGCTG
11401 AGCCACAAGA ATCACTTGAA CCTGGGAGAC AGAGGTTGCA GTGAGCCGAG
11451 ATCGCGCCAT TGCACTCCAG CCTGGGCGAC AGTGTGAGAC TCTGTCTCCA
11501 GAAAAAACAA GAATGGATAG AGTGGAACCA AGAAGAGGCA GGAAGAACAA
11551 AGACACAGAG GTGCACAGAG TTTGGGGGAA TTTTGAGGAA TGGTCTTGCA
11601 AAAGAGTGGG ATCTGGGAGA ATGAGTGGGA GTGGAAAGCA GATGAATGAA
11651 GAGAAGGTGA GCGCATCAGG GTAACAGAGA TGCGTTGTGA ACAAATGCAT
11701 GTTCTAGGAA GAGCCCTCTG GAGTGCTAGG TGCCAGAGAG GTGGGAGGAA
11751 GGATACTGGA AGCAGAGAAA CCAGTGAGGG GCCTGATCTT GGGTGGTGGG
11801 GAATGAGGGA CAGGGGAGGC CGGGATGGAA GCCAGGTGGT GGGGAATGAG
11851 GGACAGGGGA GGCCGGGATG GAAGCCAGGT TTCAGCTGAG CAGGTGGCGG
11901 TGGCATTGAT GGAGATGAGG ACATGGGGAA GGACAAAGTC CAGGTGTCCT
11951 TGAGGGAAGA CAAGAAGACA AATAATCCAG GCTCTCTGTC CTCACACCAG
12001 CTGCCCGCCC CTTTCTTCCT GGCACAGTCA TGTTGGAACC AGCTGCTGAG
12051 ACCATTCCTC AGACCCAAGA GATCATCAGT GTCACGCTGC AGGTGCTTAG
12101 TCTCTTGCCG CCGTACAGAC AGTCCATCTC TGTTCTGGCC GGGTCCACCG
12151 TGGAAGATGT CCTGAAGAAG GCCCATGAGT TAGGAGGATT CACGTGAGAC
12201 TCCCACCTCC CAGTCCTCAC CCCACCCAAC CTCACATGCC TGATAACAGG
12251 GTCACAGAAA AGACGGGGAA CAGAGGAGAG GGTTCCCTCG GGAGAGACAC
12301 TGGCCCTGCT TCTGCTTCTA CCTGCTCAGC TCCTTTCTTG CCCACGGTGT
12351 TATGGAAACA GGGAGCCATA GGCCAGCATT GTCACTGAGA GAGCAGGCTT
12401 TGGAGGCAGA GCCCCCCAGT TGGAATCCCA ACTCTAACCA GCTAGGTTCC
12451 AGGTAGGCAC CCACAATTCA CCGAGGAGAA CAGTTGTGCC CCTTCCCTGC
12501 AGGGCCAGTG TGAAGAGTCC AGGAGTTAGT ACACATAGAG ATAGTGGCAT
12551 GTGCTTTTTA TATGTGCAAG GTCCAGCACA TAGCAAGCGC TCAACACAGC
12601 GTTGCTTTCA TCAGAGTAAG AACTGTTTTT TGTTTGTTTG TTTGTTTGTT
12651 TTTAAGAGAC AGGGTCTCAA TCTTATCACC CAGGCTGGAG TGTAATTGTG
12701 CAATCACGTC TCACTGCAGT CTCGAACTCT GGGGATGAAG CAACCCTACT
12751 GTCCTGCCTC AGCCTCCCAA ATAGCTGAGA CTATAGGCAC GTGCCACACA
12801 ACCCTGGGTA ATTTTTTTTT TTTTTTTTTT GAGATAGGGT CTCTGTCTGT
12851 TGCCCAGGCT GGTCTCAAAT TCCTGGCCTC AAACCATCCT CACACCTGAG
12901 GCGCTCAAAA TATTGGGATT ATAGGTGCGA GCCATCATGC TCAGCCAGAA
12951 TAATAACTGG TTTTTTTTGT TTTTTTTTG AGACAGAGTC TCACTCTATT
13001 ACCCAGGCTC TGGAGGCCCA ACTCGTGTTT GTGTATTTGT TTATTTTAT
13051 TTATTTATTT ATTTCGAGAC AGAGCCTCTC TCTTTCACCT AGGCTGGAGT
13101 GCAGTGGCGC AATCTCGGCT CACTGCAACC TCCGTCTCCT GGGTTCAAGT
13151 GATTGTCCTG CCTCAGCCTC CTGAGTAGCT GGTGCTACAG GCGCGTGCCA
13201 CCATGCCCAG CTAATTTTTG TATTTTTAGT AGAGACAGGG TTTTACTATG
13251 TTGGCCAGCT GGTTTCTAAC TCCTGAACTC GGGTGATCTG CCTGCCTCGG
13301 CCTCCCAAAG TGCTGGGATT ACAGGCATGG GCCTCCGTGC CCGGCCATGT
13351 ATTTATTTAG GCAAGGTCTC TCTCTGTTAT CCAGGCTGAA GTGCAGTGGC
13401 ACATTCATAG CTCACTGCAG CCTCAAATTA TCCAAGTAAC AGGGACTACA
13451 GGCATGCACC ACCACACCCA TCTACTTTTT TTTGAGATGG AGTCTCCCTC
13501 TGTCGCCCAG ACTGGGTTGC AGTGGCACAA TTTCAGCTCA TGGCAGCATC
13551 TACCTCCCAG GTTCAAGCGA TTCTCCTTCC TCAGTCTCCC GAGTAGCTGG
13601 GACTATGGGC ATGCACCACC ATACCTGGCT AATGTTTATA TTTTGAGTAG
13651 AGATGGAATT TTGCCATTTT GGCCAGGCTG GTCTTGAGCT CTTGACCTCA
13701 AGTGATATGT CTGCCTCAGN NNNNNNNNNN NNNNNNNNNN NNNNNNNNNN
13751 NNNNNNNNNN NNNNNNNNNN NNNNNNNNNN NNNNNNNNNN NNNNNNNNNN
13801 NNNNNNNNNN NNNNNNNNNN NNNNNNNNNN NNNNNNNNNN NNNNNNNNNN
13851 NNNNNNNNNN NNNNNNNNNN NNNNNNNNNN NNNNNNNNNN NNNNNNNNNN
13901 NNNNNNNNNN NNNNNNNNNN NNNNNNNNNN NNNNNNNNNN NNNNNNNNNN
13951 NNNNNNNNNN NNNNNNNNNN NNNNNNNNNN NNNNNNNNNN NNNNNNNNNN
14001 NNNNNNNNNN NNNNNNNNNN NNNNNNNNNN NNNNNNNNNN NNNNNNNNNN
14051 NNNNNNNNNN NNNNNNNNNN NNNNNNNNNN NNNNNNNNNN NNNNNNNNNN
14101 NNNNNNNNNN NNNNNNNNNN NNNNNNNNNN NNNNNNNNNN NNNNNNNNNN
14151 NNNNNNNNNN NNNNNNNNNN NNNNNNNNNN NNNNNNNNNN NNNNNNNNNN
```

FIGURE 3, page 4 of 22

```
14201 NNNNNNNNNN NNNNNNNNNN NNNNNNNNNN NNNNNNNNNN NNNNNNNNNN
14251 NNNNNNNNNN NNNNNNNNNN NNNNNNNNNN NNNNNNNNNN NNNNNNNNNN
14301 NNNNNNNNNN NNNNNNNNNN NNNNNNNNNN NNNNNNNNNN NNNNNNNNNN
14351 NNNNNNNNNN NNNNNNNNNN NNNNNNNNNN NNNNNNNNNN NNNNNNNNNN
14401 NNNNNNNNNN NNNNNNNNNN NNNNNNNNNN NNNNNNNNNN NNNNNNNNNN
14451 NNNNNNNNNN NNNNNNNNNN NNNNNNNNNN NNNNNNNNNN NNNNNNNNNN
14501 NNNNNNNNNN NNNNNNNNNN NNNNNNNNNN NNNNNNNNNN NNNNNNNNNN
14551 NNNNNNNNNN NNNNNNNNNN NNNNNNNNNN NNNNNNNNNN NNNNNNNNNN
14601 NNNNNNNNNN NNNNNNNNNN NNNNNNNNNN NNNNNNNNNN NNNNNNNNNN
14651 NNNNNNNNNN NNNNNNNNNN NNNNNNNNNN NNNNNNNNNN NNNNNNNNNN
14701 NNNNNNNNNN NNNNNNNNNN NNNNNNNNNN NNNNNNNNNN NNNNNNNNNN
14751 NNNNNNNNNN NNNNNNNNNN NNNNNNNNNN NNNNNNNNNN NNNNNNNNNN
14801 NNNNNNNNNN NNNNNNNNNN NNNNNNNNNN NNNNNNNNNN NNNNNNNNNN
14851 NNNNNNNNNN NNNNNNNNNN NNNNNNNNNN NNNNNNNNNN NNNNNNNNNN
14901 NNNNNNNNNN NNNNNNNNNN NNNNNNNNNN NNNNNNNNNN NNNNNNNNNN
14951 NNNNNNNNNN NNNNNNNNNN NNNNNNNNNN NNNNNNNNNN NNNNNNNNNN
15001 NNNNNNNNNN NNNNNNNNNN NNNNNNNNNN NNNNNNNNNN NNNNNNNNNN
15051 NNNNNNNNNN NNNNNNNNNN NNNNNNNNNN NNNNNNNNNN NNNNNNNNNN
15101 NNNNNNNNNN NNNNNNNNNN NNNNNNNNNN NNNNNNNNNN NNNNNNNNNN
15151 NNNNNNNNNN NNNNNNNNNN NNNNNNNNNN NNNNNNNNNN NNNNNNNNNN
15201 NNNNNNNNNN NNNNNNNNNN NNNNNNNNNN NNNNNNNNNN NNNNNNNNNN
15251 NNNNNNNNNN NNNNNNNNNN NNNNNNNNNN NNNNNNNNNN NNNNNNNNNN
15301 NNNNNNNNNN NNNNNNNNNN NNNNNNNNNN NNNNNNNNNN NNNNNNNNNN
15351 NNNNNNNNNN NNNNNNNNNN NNNNNNNNNN NNNNNNNNNN NNNNNNNNNN
15401 NNNNNNNNNN NNNNNNNNNN NNNNNNNNNN NNNNNNNNNN NNNNNNNNNN
15451 NNNNNNNNNN NNNNNNNNNN NNNNNNNNNN NNNNNNNNNN NNNNNNNNNN
15501 NNNNNNNNNN NNNNNNNNNN NNNNNNNNNN NNNNNNNNNN NNNNNNNNNN
15551 NNNNNNNNNN NNNNNNNNNN NNNNNNNNNN NNNNNNNNNN NNNNNNNNNN
15601 NNNNNNNNNN NNNNNNNNNN NNNNNNNNNN NNNNNNNNNN NNNNNNNNNN
15651 NNNNNNNNNN NNNNNNNNNN NNNNNNNNNN NNNNNNNNNN NNNNNNNNNN
15701 NNNNNNNNNN NNNNNNNNNN NNNNNNNNNN NNNNNNNNNN NNNNNNNNNN
15751 NNNNNNNNNN NNNNNNNNNN NNNNNNNNNN NNNNNNNNNN NNNNNNNNNN
15801 NNNNNNNNNN NNNNNNNNNN NNNNNNNNNN NNNNNNNNNN NNNNNNNNNN
15851 NNNNNNNNNN NNNNNNNNNN NNNNNNNNNN NNNNNNNNNN NNNNNNNNNN
15901 NNNNNNNNNN NNNNNNNNNN NNNNNNNNNN NNNNNNNNNN NNNNNNNNNN
15951 NNNNNNNNNN NNNNNNNNNN NNNNNNNNNN NNNNNNNNNN NNNNNNNNNN
16001 NNNNNNNNNN NNNNNNNNNN NNNNNNNNNN NNNNNNNNNN NNNNNNNNNN
16051 NNNNNNNNNN NNNNNNNNNN NNNNNNNNNN NNNNNNNNNN NNNNNNNNNN
16101 NNNNNNNNNN NNNNNNNNNN NNNNNNNNNN NNNNNNNNNN NNNNNNNNNN
16151 NNNNNNNNNN NNNNNNNNNN NNNNNNNNNN NNNNNNNNNN NNNNNNNNNN
16201 NNNNNNNNNN NNNNNNNNNN NNNNNNNNNN NNNNNNNNNN NNNNNNNNNN
16251 NNNNNNNNNN NNNNNNNNNN NNNNNNNNNN NNNNNNNNNN NNNNNNNNNN
16301 NNNNNNNNNN NNNNNNNNNN NNNNNNNNNN NNNNNNNNNN NNNNNNNNNN
16351 NNNNNNNNNN NNNNNNNNNN NNNNNNNNNN NNNNNNNNNN NNNNNNNNNN
16401 NNNNNNNNNN NNNNNNNNNN NNNNNNNNNN NNNNNNNNNN NNNNNNNNNN
16451 NNNNNNNNNN NNNNNNNNNN NNNNNNNNNN NNNNNNNNNN NNNNNNNNNN
16501 NNNNNNNNNN NNNNNNNNNN NNNNNNNNNN NNNNNNNNNN NNNNNNNNNN
16551 NNNNNNNNNN NNNNNNNNNN NNNNNNNNNN NNNNNNNNNN NNNNNNNNNN
16601 NNNNNNNNNN NNNNNNNNNN NNNNNNNNNN NNNNNNNNNN NNNNNNNNNN
16651 NNNNNNNNNN NNNNNNNNNN NNNNNNNNNN NNNNNNNNNN NNNNNNNNNN
16701 NNNNNNNNNN NNNNNNNNNN NNNNNNNNNN NNNNNNNNNN NNNNNNNNNN
16751 NNNNNNNNNN NNNNNNNNNN NNNNNNNNNN NNNNNNNNNN NNNNNNNNNN
16801 NNNNNNNNNN NNNNNNNNNN NNNNNNNNNN NNNNNNNNNN NNNNNNNNNN
16851 NNNNNNNNNN NNNNNNNNNN NNNNNNNNNN NNNNNNNNNN NNNNNNNNNN
16901 NNNNNNNNNN NNNNNNNNNN NNNNNNNNNN NNNNNNNNNN NNNNNNNNNN
16951 NNNNNNNNNN NNNNNNNNNN NNNNNNNNNN NNNNNNNNNN NNNNNNNNNN
17001 NNNNNNNNNN NNNNNNNNNN NNNNNNNNNN NNNNNNNNNN NNNNNNNNNN
17051 NNNNNNNNNN NNNNNNNNNN NNNNNNNNNN NNNNNNNNNN NNNNNNNNNN
17101 NNNNNNNNNN NNNNNNNNNN NNNNNNNNNN NNNNNNNNNN NNNNNNNNNN
17151 NNNNNNNNNN NNNNNNNNNN NNNNNNNNNN NNNNNNNNNN NNNNNNNNNN
17201 NNNNNNNNNN NNNNNNNNNN NNNNNNNNNN NNNNNNNNNN NNNNNNNNNN
17251 NNNNNNNNNN NNNNNNNNNN NNNNNNNNNN NNNNNNNNNN NNNNNNNNNN
17301 NNNNNNNNNN NNNNNNNNNN NNNNNNNNNN NNNNNNNNNN NNNNNNNNNN
17351 NNNNNNNNNN NNNNNNNNNN NNNNNNNNNN NNNNNNNNNN NNNNNNNNNN
17401 NNNNNNNNNN NNNNNNNNNN NNNNNNNNNN NNNNNNNNNN NNNNNNNNNN
17451 NNNNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNNN NNNNNNNNNN NNNNNNNNNN NNNNNNNNNN NNNNNNNNNN
17601 NNNNNNNNNN NNNNNNNNNN NNNNNNNNNN NNNNNNNNNN NNNNNNNNNN
17651 NNNNNNNNNN NNNNNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
```

FIGURE 3, page 5 of 22

```
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNNNNN NNNNNNNNNN NNNNNNNNNN NNNNNNNNNN
18101 NNNNNNNNNN NNNNNNNNNN NNNNNNNNNN NNNNNNNNNN NNNNNNNNNN
18151 NNNNNNNNNN NNNNNNNNNN NNNNNNNNNN NNNNNNNNNN NNNNNNNNNN
18201 NNNNNNNNNN NNNNNNNNNN NNNNNNNNNN NNNNNNNNNN NNNNNNNNNN
18251 NNNNNNNNNN NNNNNNNNNN NNNNNNNNNN NNNNNNNNNN NNNNNNNNNN
18301 NNNNNNNNNN NNNNNNNNNN NNNNNNNNNN NNNNNNNNNN NNNNNNNNNN
18351 NNNNNNNNNN NNNNNNNNNN NNNNNNNNNN NNNNNNNNNN NNNNNNNNNN
18401 NNNNNNNNNN NNNNNNNNNN NNNNNNNNNN NNNNNNNNNN NNNNNNNNNN
18451 NNNNNNNNNN NNNNNNNNNN NNNNNNNNNN NNNNNNNNNN NNNNNNNNNN
18501 NNNNNNNNNN NNNNNNNNNN NNNNNNNNNN NNNNNNNNNN NNNNNNNNNN
18551 NNNNNNNNNN NNNNNNNNNN NNNNNNNNNN NNNNNNNNNN NNNNNNNNNN
18601 NNNNNNNNNN NNNNNNNNNN NNNNNNNNNN NNNNNNNNNN NNNNNNNNNN
18651 NNNNNNNNNN NNNNNNNNNN NNNNNNNNNN NNNNNNNNNN NNNNNNNNNN
18701 NNNNNNNNNN NNNNNNNNNN NNNNNNNNNN NNNNNNNNNN NNNNNNNNNN
18751 NNNNNNNNNN NNNNNNNNNN NNNNNNNNNN NNNNNNNNNN NNNNNNNNNN
18801 NNNNNNNNNN NNNNNNNNNN NNNNNNNNNN NNNNNNNNNN NNNNNNNNNN
18851 NNNNNNNNNN NNNNNNNNNN NNNNNNNNNN NNNNNNNNNN NNNNNNNNNN
18901 NNNNNNNNNN NNNNNNNNNN NNNNNNNNNN NNNNNNNNNN NNNNNNNNNN
18951 NNNNNNNNNN NNNNNNNNNN NNNNNNNNNN NNNNNNNNNN NNNNNNNNNN
19001 NNNNNNNNNN NNNNNNNNNN NNNNNNNNNN NNNNNNNNNN NNNNNNNNNN
19051 NNNNNNNNNN NNNNNNNNNN NNNNNNNNNN NNNNNNNNNN NNNNNNNNNN
19101 NNNNNNNNNN NNNNNNNNNN NNNNNNNNNN NNNNNNNNNN NNNNNNNNNN
19151 NNNNNNNNNN NNNNNNNNNN NNNNNNNNNN NNNNNNNNNN NNNNNNNNNN
19201 NNNNNNNNNN NNNNNNNNNN NNNNNNNNNN NNNNNNNNNN NNNNNNNNNN
19251 NNNNNNNNNN NNNNNNNNNN NNNNNNNNNN NNNNNNNNNN NNNNNNNNNN
19301 NNNNNNNNNN NNNNNNNNNN NNNNNNNNNN NNNNNNNNNN NNNNNNNNNN
19351 NNNNNNNNNN NNNNNNNNNN NNNNNNNNNN NNNNNNNNNN NNNNNNNNNN
19401 NNNNNNNNNN NNNNNNNNNN NNNNNNNNNN NNNNNNNNNN NNNNNNNNNN
19451 NNNNNNNNNN NNNNNNNNNN NNNNNNNNNN NNNNNNNNNN NNNNNNNNNN
19501 NNNNNNNNNN NNNNNNNNNN NNNNNNNNNN NNNNNNNNNN NNNNNNNNNN
19551 NNNNNNNNNN NNNNNNNNNN NNNNNNNNNN NNNNNNNNNN NNNNNNNNNN
19601 NNNNNNNNNN NNNNNNNNNN NNNNNNNNNN NNNNNNNNNN NNNNNNNNNN
19651 NNNNNNNNNN NNNNNNNNNN NNNNNNNNNN NNNNNNNNNN NNNNNNNNNN
19701 NNNNNNNNNN NNNNNNNNNN NNNNNNNNNN NNNNNNNNNN NNNNNNNNNN
19751 NNNNNNNNNN NNNNNNNNNN NNNNNNNNNN NNNNNNNNNN NNNNNNNNNN
19801 NNNNNNNNNN NNNNNNNNNN NNNNNNNNNN NNNNNNNNNN NNNNNNNNNN
19851 NNNNNNNNNN NNNNNNNNNN NNNNNNNNNN NNNNNNNNNN NNNNNNNNNN
19901 NNNNNNNNNN NNNNNNNNNN NNNNNNNNNN NNNNNNNNNN NNNNNNNNNN
19951 NNNNNNNNNN NNNNNNNNNN NNNNNNNNNN NNNNNNNNNN NNNNNNNNNN
20001 NNNNNNNNNN NNNNNNNNNN NNNNNNNNNN NNNNNNNNNN NNNNNNNNNN
20051 NNNNNNNNNN NNNNNNNNNN NNNNNNNNNN NNNNNNNNNN NNNNNNNNNN
20101 NNNNNNNNNN NNNNNNNNNN NNNNNNNNNN NNNNNNNNNN NNNNNNNNNN
20151 NNNNNNNNNN NNNNNNNNNN NNNNNNNNNN NNNNNNNNNN NNCCAAATC
20201 AACCAGTTGC ATAAATCACT CCTCTATCTT CCTTGGGGTG GAAAGTGGAT
20251 GGGAGTTATA ATTTGAGTTC TCTTTTGTCT TAGTCCATTG AAGCTGCTAT
20301 TACAAAATAC CATAAACTGG GTGGCTTATA AACAGCAGAA ATGAGGCCGG
20351 GTGCGGTGGC TCATGCCTAT AATTCCAGCA CTTTGGGAGG CCAAGGCAGG
20401 TGGATCACCT GAGATCAGTA GTTCAAGACT AGCCTGACCA ACATGGTGAA
20451 ACCCTGTCTC TACTAAAAAT ACAAAAAATT AGCTGGGGGT GGTGGCGGGC
20501 ACCTGTAATC CCAGCTACTC AGGAGGCTGA GGCAGGAGAA TCGCTTGAAC
20551 CCAGGAGGCG GAGGTTGCCG TGAGCTGAGA TCACGCCATT GCATTTCAGC
20601 CTGGGCACAA AGAGTGAAAC TCCATCTCAA AATGAAATAA AATAACAGAA
20651 ATGTATTTCT TAACAGTTCT GGAGGTTGGG TGGGCAGTCC CAGATCAGGA
20701 CACTGACAGA TTCAGTGTCT GATCGGGGCC CACTTTCTGG TGTTACCTGC
20751 TGGCTGTGTT CTCACATGGT GGAAGGAACA TGCAACTTT CTGGGGCCTT
20801 GTTTTTTAAT TTAAAAAAAA AAAATATTTT CCTGGCCCTT GCCTGCTGAA
20851 GGAACCTCTT TTATAATGGT ACTTAAAAAT TTTTTTTTTT GAGATGGGGG
20901 TCTCACTCTG TCACCCACGC TGAGTGCAGT ATCACAATCT CAGCTCACTG
20951 CAACCTCTGC CTCCCTGGTT TAAGCGATCC TCCCACCTCA GCCTCCTGAG
21001 TACGTGTGAC CATAGGCCCA TGGCACAAAG CCCAGCTAAT TTTTTGTATT
21051 TTTAGTAGAA ATGTGGTTTC ACCATGTTGC ATAGGCTGGT CTCGAACTTC
21101 TGAACTCAAG TGATCTGCCT GCCTTGGCCT CCCAAAGTGC TGGGATTCTA
21151 GGTATGAGCC ACCCTGCTCG GCCTATAATG GCACTTTCCT ATCCCATTGA
21201 TGAGGCTCTA CTCTCATGAC CTAATCATCT CCCAAAGGCC CTAAGGCCTC
21251 CTGATACCAT CACCTTTGGG GTTAGGTTTT AACATATACA TTTTGGGGGG
```

FIGURE 3, page 6 of 22

```
21301 ACACAGACAT TTTAGACCAT AGCACCTCCA TTGAAAGGAA ACATTTCTGA
21351 CACCTGGCTA TCTCAAAGGG CCCTTTCAGT TCCCCTGCAG GCTGCATTCC
21401 CACATCACCA ACAAGAGCAG CGACACTCAC TCAGAGGTTA AATAACTTGT
21451 CCAGAGTCAC AGCAGTAATG AATGACAGAG CTGGGGCTTG AATCCAGGCG
21501 TCCTCCTAGA GCCTGGATTC TGTGTAGTGA GTGAAAGCTG ACTCCTGGGA
21551 GACTTCTGCG TGGTCCTGGT TCTCTCTCCA GACTGCACTG CGCAAGTTTC
21601 TCTTCCTGAT GGTCCCTAGG GTATTACAAA GACAGTGGCC CTGCCTGTCA
21651 GGTGTTTTTA TTACCAGATG AGGTCATGGC CTCAGGAACC CTGTAGGAAG
21701 CTGAGTTCAG AGTCTTTGAG CAGGCTTTAG GGAGGTTCCA GCTTCCCACC
21751 ACCAAGCCCC AGGTGGATTC TTACAGACTC TAGCCTCAGG GTGGGGGGTC
21801 TGGAAGATGA GGTTGCGGGG TGCGATATTC TGCCCAATTC GCCCCTCCTT
21851 GCTCAATCTG TTTCTGCAGG TATTGCTGAC TACAGACCCA AGGATGGAGA
21901 AACCATTGAG CTGAGGCTGG TTAGCTGGTA GCCCCTGAGC TCCCTCATCC
21951 CAGCAGCCTC GCACACTCCC TAGGCTTCTA CCCTCCCTCC TGATGTCCCT
22001 GGAACAGGAA CTCGCCTGAC CCTGCTGCCA CCTCCTGTGC ACTTTGAGCA
22051 ATGCCCCCTG GGATCACCCC AGCCACAAGC CCTTCGAGGG CCCTATACCA
22101 TGGCCCACCT TGGAGCAGAG AGCCAAGCAT CTTCCCTGGG AAGTCTTTCT
22151 GGCCAAGTCT GGCCAGCCTG GCCCTGCAGG TCTCCCATGA AGGCCACCCC
22201 ATGGTCTGAT GGGCATGAAG CATCTCAGAC TCCTTGGCAA AAAACGGAGT
22251 CCGCAGGCCG CAGGTGTTGT GAAGACCACT CGTTCTGTGG TTGGGGTCCT
22301 GCAAGAAGGC CTCCTCAGCC CGGGGGCTAT GGCCCTGACC CCAGCTCTCC
22351 ACTCTGCTGT TAGAGTGGCA GCTCCGAGCT GGTTGTGGCA CAGTAGCTGG
22401 GGAGACCTCA GCAGGGCTGC TCAGTGCCTG CCTCTGACAA AATTAAAGCA
22451 TTGATGGCCT GTGGACCTGC TACAGTGGCC TGGTGCCTCA TACTCCTCAG
22501 GTGCAGGGGC AGGGACAAGA GAAGGGGGAA GTAACCCCAT CAGGGAGGAG
22551 TGGAGGGTGC CTGAGCCGCC ATGTGGGCAT TGGGGGAGTG ATGGGAATGC
22601 CAGCAGTGAT GACGTTGACT ACTGACTGAG CACCCACTAC TATGACTGAG
22651 CACTCACTCG CTAGATACTA TCTTGAACTG CTCTGTGAGG TTGTTGATAT
22701 TTTCATTTTT ATCTGTGCTT TACAAATCAG GAAACTGGGA GGCCGGGCGT
22751 GGTGGCTCAC GCCTGTAATC CCAGCACTTT AGGAGGCCAA GGCAGGTGGA
22801 TCACAAGGTC AGGAGTTTGA GATCAGCCTG GCCAACATGG TGAAACTCCA
22851 TCTTTACTAA AAATACAAAA AATTAGCCAG GCATGGTGTT GCATGCCTGC
22901 ATGCCTGTAA TCCCAGTTAC TTGGGAAGCT GAGGCAGGAG AATTGCTTGA
22951 ACCCTGGAGG CGGAGGTTGT AGTGAGCCGA GATCACGCCA TTGCACTCCA
23001 GCTTGGGCAA GAAGAGAAAC ACTCTCAAAA AAAAAAAAAA ATCAGGAAAC
23051 TGGTGCTCAA AAAGGAAAAG TGACTCACCA AGGTCACAGA CTAGGCAGTG
23101 ATGCTGGGGG AACCTGGCTC AGGGGACACA GACCTGGCCT GGGGCAGCCT
23151 TGCAGCTCCT CCACTAAAAT ACTGAAAATG AGGGGCTTCG ATGATGGTTA
23201 TAATCGTATG GCAGAGCCCC AACTCAACTG GAGCCCTGGG ACCCAGAAGC
23251 TAGGGTCTCA CTCCCTGCTT TTCCACAAGG CACCATTAGG GCATCACCCC
23301 AGGCCTCGGC AGCCACGACG CAGGGATCCT GCCTCTCATT GGTTGGGGGC
23351 TTAGGGGCTC TGGGCTGCCC TCTTGAAGAG GGGGTTCAGC CCAGCGAGGC
23401 ACCCCCTATG CTGCACCCCA CCAAGGTTAG GAAGAGGTCC TGTCCTCAGT
23451 GGGGCCCTCT GATGAACAGC CCATCAGGTC TGCGTCCACA TGCCTTGGAA
23501 GAGATGGTGA CATACTCAAA GTCCTTGAAG CCGCATATTA AACCACCTAG
23551 AGCACCATCT TCAAACATTT AGGGTCTGAG AAGATAGGGG AAGTAAGCAA
23601 TTTAAAACAT TTCTTTATAT TGGGCCAGGT GCAATGGCTC ACGTCTGTAA
23651 TCCCAGCGCT TTGGGAGGAC GAGGATCACC TGAGGTCAGG AGTTCAAGAT
23701 CAGCCTGGCC AACATGGAGA AACCCCATCT CTACTAAAAA TACAAAAATT
23751 AGCTCAGGCG TGGTGATGTG CACCTGTAAT CCTAGCTATT CAGGAGGCTG
23801 AGGCACAAGA ATTGCTTGAG TCAATATTGC ACCACTGCAC TCCAGCCTGG
23851 GCAACAGCGA GACTCTTGTC TCAAAAAAAA AAAAAGATAT TTGCTGAAAA
23901 GACCCAGCCT GCCAAACTCA GGGGCAGCCA AGGGAGGTAG TGAAATGGAA
23951 GTTGGAGCTC AGCGCTCCCA CACCTCCACT GCCCTCAGGC CTTCTCTGCC
24001 TCTTTCCCAT CAGTCAGCTG CTTCTGGGCA TGGTCCTGGC AGAGACTTGG
24051 CCTCCTTCCA GTTCAAGCTC CCTCTTAGAT TGTGTCCCAC GCCACTGAGT
24101 CTTTGGGACA CTGGGTCAGA TGTCTAGTCT GGCACAATTG GCAGGAATCC
24151 CAAGAAACAG TGTGAGTGAG GGGACAGTCG TGTTGAGTGC CCTCCATCTG
24201 GGACTGGGAG GCAGGTCTAT GTCAGGCCTG CATTTAGATC TCTAATGGCT
24251 CCAGACAAGC CCCTTCAGCT CACTAAGCCT GTTTCCTAAC ACAGCTGTGG
24301 GATGGTGCTT TGGTTTACAT AGCACGCGAT ACCATCATAG ATCACATGGG
24351 GAAACTGAGG CCCCAGGAGT GATCTGCTGG CACATGCAGT GACAAGAGGA
24401 GAGGCCCATC TCAGCCTTGC AGCAAGGTTG CCAGAAATCG ATTCTCGCCC
24451 CCATCCCGTA AAGATAGCTG GGATTACAGG TGTGCACCAC CATGCCCAGC
24501 CTAATTTTTG TATTATTAGT AGAGATGGGG TTTCACCATG TTGTCCAGGC
24551 TGGTCATGAA CTCCTGACCT CAAGTGATCC ACCCGCTTTG GCCTCCCAAA
24601 GTGCTGGGAT TACAAGCATG AGCCACAGTG CCTGGCCTGA CCCTGCTCTT
24651 TTGAAAGACC ATTCCCCCAA ATTCTGTGCA CCTGTGTGCC TTTCTTCTCT
24701 CTGCCTCCTC TCAGCTCTGC CCCGCTCTCC TCCCTTCTCC TCTGGCAAAT
24751 CCCACTCATC TCTTGAAGCC CTTCTTCCAG GGAAGCCCT GATCATGCTG
24801 CTTTCTCCTG TGGGAGGGAT GAAGGACGTG GCCCACGGAG TTTGTTTTGT
```

```
24851 TTTGTTTTGA GATGGAGTTT TGCTCATGTT GCCCAGGCTG GGGTACAATG
24901 GTACGATCTC AGCTCACTGC AACCTCTACG TCCCGGGTTC AAGCGGTTCT
24951 CCTGCCTTAG CCTCCCCAGT AGCTGGGATT ACTGGCATGA ACCACCACAC
25001 CTGGCTAATT TTGTGTTTTT AGTAGAGATG GGGTTTCTTC ATGTTGGTCA
25051 GGCTGGTCTC GAACTCCCAA CCTCAGGTGA TCTGCCTGCC TCGGCCTCCC
25101 AAAGTACTGG GATTACAGGG TTGAGCCACT GTGCCTGGCC CAGGCCCACG
25151 GAGTTTTAAG AGGCTTCCTG TGGCAGTGGC ATCCAGACGG AGTGCAGAAA
25201 CTCAAAGTTG AAGGCCAGAA GCTCAGGGAA GGGGGAGTGT GAGTTGAGGA
25251 GTCTCTTGGC TGCCAGGGCC AGAAACCGAA CTCCAAGCCT CTCCACAACA
25301 GCGGGTGTAG AGCATGTAGA ATCAGAGAGG AGGCTGAGCC ATGCAGCCCC
25351 GAGAAGAGGG AATGCCACT GAGCCACAGA GACCCAGTGC CACTGCCAGG
25401 TGTCTCTGCC TCCACTTCCC ATGACCCGGC CTGTCTCTGT ATGCAGGCTT
25451 CACCCTCTCT CGTTGTACAT TGTACACATT CTAGGTGACA CCAGCAGCTT
25501 CTGATTCTCA TCTCCCATAA CATCAGCCCC CCAGAGAGGG GACAACTGCT
25551 GAGCTGATAA CATAATAGAT GCCCCTTTCC TGGAGGCCAT GGTCATGGTC
25601 AGCGTGGAGA GGATGAAGCC TGAGCAGGCA GGATCGGGGG TCTAGAGGGG
25651 AAGGAGGTGG AAGTTGAGAT CACAGACCTG TGGTCAGGTG GCCTGGGAAG
25701 GGTTTGACGA GTGTCGGCCC AAAGAGCTTG GAAGGGATTT TGCTGCTGTG
25751 GGTGAGCACT GCCTCTCCCC TTAGGGACAA CAGCCACCTC TTCTCTCCCC
25801 ATTTGCCTTT CCCTTCTGTA GATATGAAAC ACAGGCCTCC TTGTCAGGCC
25851 CCTACTTAAC CTCCGTGATG GGGAAAGCGG CCGGAGAAAG GGAGTTCTGG
25901 CAGCTTCTCC GAGACCCCAA CACCCCACTG TTGCAAGGTG AGTCATGGCC
25951 TGACACTCTG GATGTGTCCC CTACCCCAAG CTTACTCAGC CAAGAGGCTT
26001 CATCAACTCA CCCCAGCTTT CCCTAGCACC CTCCTGGGCC ACACCTTCAC
26051 AAAATCACTG ATGCTCAAAG TTGGATATAA TATATTGAAC TGAAGCCTTA
26101 GCATTTTTAT GCAAGTTACT GTGGAAATTC TAGGAAACCA GACAGATTAC
26151 AAAAAAAAAA AAAAACTAGA AGAAAATTAA CATCACCTAG GATATACTAC
26201 CTAGGAATAA CGTCTTTTAT TTTGAGATGG AGTTTCGCTC TTGTTGCCCA
26251 GGCTGGAGTG CAGCGGTATG ATCTCGGCTC GCTGCAACCT CCGCCTCCTG
26301 GGTTCATGTG ATTCTTCCAC CTCGGCCTTC CTAGAGCCCA AGTGGTCTGC
26351 CTGCCTCTGC CTCCCAAAGT TCTGGGATTA CAGGCATGAG CCACCGCACC
26401 CAGCCAAAAT TACTTAACTT TCTTCTAGA TACTTTTAA AAATATGGCA
26451 GTAAGTTTTT CATAAAAAAT GGAGCCATGC TATCCAGTGG AAATTTAATG
26501 TTGCCCACAT GTATAACTTA AAAATTTCAT ATATGTGTAT ACATATATAT
26551 GAAATATATA TACAGACA CACATATATA TGTATACATA TATATACACA
26601 TATATATGTA TACATATATA CACACATATA TGTATACATA TATATACACA
26651 CATATACACA TATATACACA CACATACATA TATACACACA CATATATACA
26701 CACATATATA CACACATGCA CACATATATA TGTATACATA TATACACACA
26751 TGTATACGTA TATATACACA CATATATACA CACATATATA TACACACATA
26801 TACACACATA CACACATATA TATACACACA TATATACACA CATATATACA
26851 CACATATATA TGTATACATA TATATACACA CATATATACA CATACACACA
26901 TACATATATA CACATATACA CATATACACA CACATATACA CACATGTATA
26951 CATATATATA CACACATGTA TACATATGTA TACACACACA TATATGTATA
27001 CATATATACA CACATACATA TGTGTACATA TATACACACA TACATATGTA
27051 TACATATATA CACACAT
(SEQ ID NO:5)
```

Isoform 1:

FEATURES:

| | |
|---|---|
| Exon: | 2031-2094 |
| Intron: | 2095-5569 |
| Exon: | 5570-5762 |
| Intron: | 5763-7571 |
| Exon: | 7572-7741 |
| Intron: | 7742-10000 |
| Exon: | 10001-10173 |
| Intron: | 10174-10298 |
| Exon: | 10299-10485 |
| Intron: | 10486-12027 |
| Exon: | 12028-12193 |
| Intron: | 12194-25821 |
| Exon: | 25822-25939 |

Allelic Variants (SNPs):

| DNA Position | Major | Minor | Domain | Protein Position | Major | Minor |
|---|---|---|---|---|---|---|
| 921 | C | T | Beyond ORF(5') | | | |
| 1781 | C | T | Beyond ORF(5') | | | |
| 1850 | G | A | Beyond ORF(5') | | | |
| 2839 | A | G | Intron | | | |
| 3730 | G | A | Intron | | | |
| 6631 | G | A | Intron | | | |
| 6945 | - | A | Intron | | | |
| 6952 | A | T | Intron | | | |
| 7457 | G | A | Intron | | | |
| 7830 | T | A | Intron | | | |
| 8089 | T | C | Intron | | | |
| 8551 | C | T | Intron | | | |
| 9269 | G | C | Intron | | | |
| 9362 | C | T | Intron | | | |
| 9782 | G | T | Intron | | | |
| 11493 | G | A T | Intron | | | |
| 12260 | A | G | Intron | | | |
| 13086 | T | C | Intron | | | |
| 13183 | T | C | Intron | | | |
| 21240 | C | G | Intron | | | |
| 21695 | A | G | Intron | | | |
| 22058 | C | T | Intron | | | |
| 22233 | C | A | Intron | | | |
| 22245 | C | - | Intron | | | |
| 22375 | C | T | Intron | | | |
| 23042 | A | - T | Intron | | | |
| 23344 | T | C | Intron | | | |
| 23873 | A | - | Intron | | | |
| 24764 | G | T | Intron | | | |
| 24939 | T | C | Intron | | | |
| 24945 | G | A | Intron | | | |
| 25092 | C | T | Intron | | | |
| 25428 | T | G | Intron | | | |
| 25513 | C | T | Intron | | | |
| 25684 | C | T | Intron | | | |
| 26165 | A | - | Beyond ORF(3') | | | |

Context:
DNA
Position

921  TTGGAGATATTTTAAGGTCATAGTGTCTTCACAAATTGAGCTGAAAGGGAACTGTTAGGA
     TGATCTTGCCTAACCCTCTCATCTCACACAGGAAGAACTATTTTAAACTCGAGAGGTTAA
     GTGACCTGGCCAAAGTCACACAGCCACCACTAGTTAACTCGTATACATTGATTCTCCTGT
     GGGGCTGGGCAGATGAGGAATCTTTTGTTCTCTTCCCTGTTTGCAGAGATTTTTTTTGAG
     GTTACTTTCCGAGTTCTGGCAAGTACCCCTGCTTCTGGTAGCTTTGTGTCTCGATTCAAT
     [C,T]
     TCATTCTTTTTATTTTATTTTATTTTTGAGACAGGGTCTCACTTTGTCACCCAAGCTGGA
     GTGCAGTGGTGTAATCTTGGCTCACTGTAGCCTCCACCTCTTGGGTTCAAGCGATCCTCC

```
           TGCCTCAGCCCCCCAAGTAGCTGGGATTACAGACGTCTGCCACCACGCCAGGCTAATTTA
           TGGTTTTTTGTATGTGTTTTTTGTGTTTTTGTAGAGACAGTGTTTCCCCATGTTGCCCAG
           GCTGGTCTCCAACTCCTGAGCTCAAGTGATCTGCCCGCCTCAGCCTTTCAAAGTGCTAGG

1781   ACAGCTGACTCCAGCAATGCTGCTCACGTGACCACTGCAGCTGCAGCTCCCGTTCCACTC
           CTTGTCCTGGGCTAGGTGGGCACTACCAGGGGCTCCTTTGGTAAGGAGTACCGGGTAGGC
           ACCCGGTCCTGCCAATCCACCACTGGAACAGCTGGGGGGACAGCAGACAGGCACGGTCGG
           ACAGACTTGACAGATCAGGCATCAGGCCCTCTGCGCTGGTCCCGGGCTCTTTAAGCAGGA
           ACGTGAATGGCCTCAAGATGTCTCACATGGTCCCACTAGCCCTCCTCCTCCCTTTGTTCC
           [C,T]
           TACCTCCAGGAGGGCTGCTCTGCCCTTCCTTCCTCTGTTCTTTGGCCTTATGTTCCCCGC
           CACCACAGGCCTTCCCCCGCCCCACCCCTCTGCAGACTTAGCCGTGCATTGCAGGCATGG
           AGGATTAATCAGTGACAGGAAGCTGCGTCTCTCGGAGCGGTGACCAGCTGTGGTCAGGAG
           AGCCTCAGCAGGGCCAGCCCCAGGAGTCTTTCCCGATTCTTGCTCACTGCTCACCCACCT
           GCTGCTGCCATGAGGCACCTTGGGGCCTTCCTCTTCCTTCTGGGGGTCCTGGGGGCCCTC

1850   GGCTAGGTGGGCACTACCAGGGGCTCCTTTGGTAAGGAGTACCGGGTAGGCACCCGGTCC
           TGCCAATCCACCACTGGAACAGCTGGGGGGACAGCAGACAGGCACGGTCGGACAGACTTG
           ACAGATCAGGCATCAGGCCCTCTGCGCTGGTCCCGGGCTCTTTAAGCAGGAACGTGAATG
           GCCTCAAGATGTCTCACATGGTCCCACTAGCCCTCCTCCTCCCTTTGTTCCCTACCTCCA
           GGAGGGCTGCTCTGCCCTTCCTTCCTCTGTTCTTTGGCCTTATGTTCCCCGCCACCACAG
           [G,A]
           CCTTCCCCCGCCCCACCCCTCTGCAGACTTAGCCGTGCATTGCAGGCATGGAGGATTAAT
           CAGTGACAGGAAGCTGCGTCTCTCGGAGCGGTGACCAGCTGTGGTCAGGAGAGCCTCAGC
           AGGGCCAGCCCCAGGAGTCTTTCCCGATTCTTGCTCACTGCTCACCCACCTGCTGCTGCC
           ATGAGGCACCTTGGGGCCTTCCTCTTCCTTCTGGGGGTCCTGGGGGCCCTCACTGAGATG
           TGTGGTGAGTAACTCGCCTCTATCCTGTGCCTCTTTCCTCCTGGGTCCTTAGTGGGGTGG

2839   AACATAGGGAGACCCCATCTCTACAAAAAATAAAAAAAATTAAAAAATAGCTGGGCATGG
           GGAAGACTTTCTGAAGACCAAGAGGACACATGGGAGCTGAAACTCGAAGGAAGAAAAGGA
           GCTGGCAGGAAAGGAGTGGGGGACACACATTCTAGGCAGCAGGAAGTGAGCCTTCGGAGG
           TCCTGCCTGCTCCAGCTCTGTGCCCCAAGGGGTCTCTTGGAGCACAGTCTCCTGGGACCT
           GTCTATGAGTCTGAGCTTAGAGGCTCAGGGCTGCTCCTTCAGACAGGAGGCAGAAGGCAG
           [A,G]
           CTTTGGGAACTTTGGGCCGCCCACGCGCCTTTTCTCCTCCTCTGCACCTAGGATTACGTT
           GAGCAATACACTTTCACCCCCATGGTCTCTTGAGACCCTGGGGAAACCCTGAGAGGTGGG
           TGCAGTCATGTCCAGGTGTCAAGTGAAGAAGTCGAGGGTTGGAGGGGCTGAGTGACCCAC
           TCAGGGTGCTCCACCTTTTCCAGAGCTTTGCTGAACTTAGTTTTTAGAACTTGAAGCCTC
           GTTTGTTTTCGTTTTGTTTTTTGTTGAGAGAGGTTCTCCCTCTGTTGCCCAGGCTGGAGT

3730   GACACCTCAGGTCTGGGCCCAGGAACCCCAGCTCTTGGTTCATGTCCGGACAGTCCCCAG
           GGGAGTTCTGGGTTCAACCAGCAAGAGCTCTTCCTCCTGGCTGATCTGGTCCTCAGCCTT
           GGACAGTTAGTCCATTAACCTGACCCCACAGGAGCCCCAATCCCTTGGGGTCTGGGGAAT
           CTTGAACTGGGGTTTGGGGTGCAAATATCTGCACTGAGTCACTTAATTGCACCCAGCCTC
           ATTCCTTTATCTGTAAAGTGGGCTAAGAATGCTCCCCTGCCTTCCTCCTCGGTGTAGTAC
           [G,A]
           AGGAAGGATCCCATGACACCTGCTCTCCCAGTTTAAAGCTCTATATGTATGTTGTGAAAT
           TGACAGGGATCGCTGCACAAACGCTAATGCAAAGTGGGCTCCTGTGCTTCCTTTTCTCTT
           TCTTCTTCTTTTTTTTTTTTTAATTTTCTTCTAGAGATGAGGTCTCACTATATTGCCCA
           GGGTTGGTTTCAAACTCCTAGGGTCAAGCGATCCTCCCACCTTGGCCTCCCAAACTGCTG
           GTATTACAGGCGTGAGCCACTCTGTCTGGCTCCTATGCTTGTGAATGTCAACAGCAATCA

6631   TGAATAGCTGGGATTACAGGCGTGTGCCACCATGCCCAGCTGATTTTTGTATTTTTGGTA
           GAGATAGGGTTTCACCATGTTGGCCAGGCTGGTCTTGAACTCCTGACCTCAGGTGATCCG
           CCTGTCTTGGCTTCCCAAAGTGTTGGGATTATAGGCATGAGCCACTGCACCAATCCAAAA
           GCAGCATCTTTGTGCTCCCTTTTCAAGAGGCATCACAGAGAGGCCTGTTTTGGGGTTTGA
           ATGAGAGGCGAAGAATCAGCCATGGAGTGCCTCTTTCTCAGACTCCCTCTTGAGAAGTGG
           [G,A]
           TGCAGGGGTGGAGAGAAAAGAAGACTAGGCATAGTGGCTCATACCTGTAATCCCAACATT
           TTGGGAGGCTGAGGCAGGAAGATTGCTTGAGCTCAGGAGTTTGAGACCAGCCTAGGCAAC
           ATAGTGAGACCACATCTCTTAAAAAAAAGAAAAAGAAAAAAAATGAGCCAGGTGTAGTGA
           CTCATGCCTGTGGTCCCCACTTCTCCGGAGGCAAAGGTGGGAGGATCTTTTGAGGCTGAG
           AAATCGAGGCTACAGTGAGCCATGGTGGCACCACTGCACTCCAGCCTGGGAGACAGAGAG

6945   AGAAAAGAAGACTAGGCATAGTGGCTCATACCTGTAATCCCAACATTTTGGGAGGCTGAG
           GCAGGAAGATTGCTTGAGCTCAGGAGTTTGAGACCAGCCTAGGCAACATAGTGAGACCAC
           ATCTCTTAAAAAAAAGAAAAAGAAAAAAAATGAGCCAGGTGTAGTGACTCATGCCTGTGG
           TCCCCACTTCTCCGGAGGCAAAGGTGGGAGGATCTTTTGAGGCTGAGAAATCGAGGCTAC
           AGTGAGCCATGGTGGCACCACTGCACTCCAGCCTGGGAGACAGAGAGACCCTATCTCAGT
           [-,A]
           AAAAAAAAAAATAAAAATATGGCTGGGTGTGGTGGCTCACGCCTGTAATCCCAGCACTTT
```

```
        GGGAGGCCAAGGTAGGTAGATCACATGAGGTTAGGAGTTCGAAACCAGTCTGGCCAACAT
        AGTGAAACCCTGTCTCTACTGAAAATACAAAAAATTAGCCAAGGGTGGTGGTGGGCAACT
        GTAATCCCAGCTACTTGGGAGGCCGAGGCAGAAGAATCGCTTGAACTCGGGAGGCGGAGG
        TTGCAGTGAGCTGAGAACATGC

6952    AAGACTAGGCATAGTGGCTCATACCTGTAATCCCAACATTTTGGGAGGCTGAGGCAGGAA
        GATTGCTTGAGCTCAGGAGTTTGAGACCAGCCTAGGCAACATAGTGAGACCACATCTCTT
        AAAAAAAAGAAAAGAAAAAAAATGAGCCAGGTGTAGTGACTCATGCCTGTGGTCCCCAC
        TTCTCCGGAGGCAAAGGTGGGAGGATCTTTTGAGGCTGAGAAATCGAGGCTACAGTGAGC
        CATGGTGGCACCACTGCACTCCAGCCTGGGAGACAGAGAGACCCTATCTCAGTAAAAAAA
        [A,T]
        AAAATAAAAATATGGCTGGGTGTGGTGGCTCACGCCTGTAATCCCAGCACTTTGGGAGGC
        CAAGGTAGGTAGATCACATGAGGTTAGGAGTTCGAAACCAGTCTGGCCAACATAGTGAAA
        CCCTGTCTCTACTGAAAATACAAAAAATTAGCCAAGGGTGGTGGTGGGCAACTGTAATCC
        CAGCTACTTGGGAGGCCGAGGCAGAAGAATCGCTTGAACTCGGGAGGCGGAGGTTGCAGT
        GAGCTGAGAACATGCCACTGCACTCCAGCCTGGGCAACAAGAGCGAAACTCTGTCTCAAA

7457    AAGAATCGCTTGAACTCGGGAGGCGGAGGTTGCAGTGAGCTGAGAACATGCCACTGCACT
        CCAGCCTGGGCAACAAGAGCGAAACTCTGTCTCAAAGAAAATAAATAAATAAAATAAAAA
        AATAAAAAAGGAGGGGGCATATGGGTGAAGTATGGACAAAATAGTGGGGCAGGCACAGAT
        GATCTGGACACAGGAGCCCTTGGAGTTTATTCTTGAATCTAACTGTTCATCTTTATTAAA
        TATTTGTGGCATACACCTCACAACAACATAGCCAACACACCTCCTTTTGGAGCTTTTATC
        [G,A]
        AAGTTTCCCACTGTTAAGATTTTTTCCCGCTTTGTGATGCGGGTGGGGTGGGTGCTGTAA
        GCAGGCTTACGGGGTGGCAGTTTCTCACAAAGGCATTAACTGGCCTTGTCCTAGGTCTGC
        CTTCAGCGAGGATGACGGTGACTGCCAGGGCAAGCCTTCCATGGGCCAGCTGGCCCTCTA
        CCTGCTCGCTCTCAGAGCCAACTGTGAGTTTGTCAGGGGCCACAAGGGGGACAGGCTGGT
        CTCACAGCTCAAATGGTTCCTGGAGGATGAGAAGAGAGCCATTGGTGAGCAGACACCATC

7830    GGTGGCAGTTTCTCACAAAGGCATTAACTGGCCTTGTCCTAGGTCTGCCTTCAGCGAGGA
        TGACGGTGACTGCCAGGGCAAGCCTTCCATGGGCCAGCTGGCCCTCTACCTGCTCGCTCT
        CAGAGCCAACTGTGAGTTTGTCAGGGGCCACAAGGGGGACAGGCTGGTCTCACAGCTCAA
        ATGGTTCCTGGAGGATGAGAAGAGAGCCATTGGTGAGCAGACACCATCCGCTGGGGGTGG
        GGAGCAGCTGGGAGGGCTCATCAGATGATATTCTCCAATGAGAATCAGAACTTTGGGTTT
        [T,A]
        CTCCCCAGGCGTCTTTCCCACCATCCATTCTGCCCATCTCACTGCCTACGTAGAGGCTCG
        AACCTGTCCCCATAGCCATCCTTGACCCAGCTTTTCCCGCGCTGCACACATACTATTGAC
        AGGTGTGTTTCGTGGTTTTTGTTTTTGTTTGTTTGTTTGTTTTGAGTTGGAGGTTTGC
        TCTTGCTGCCCAGGCTGGAGTACAATGGCGCAATCTCAGCTCACCGCAATCTCTGCCTCC
        TGGGTTCAAGCAATTCTCTTGCCTCAGCCTCCTGAGTAGCTGGGATTACAGGCATGCGCC

8089    ATCAGATGATATTCTCCAATGAGAATCAGAACTTTGGGTTTTCTCCCCAGGCGTCTTTCC
        CACCATCCATTCTGCCCATCTCACTGCCTACGTAGAGGCTCGAACCTGTCCCCATAGCCA
        TCCTTGACCCAGCTTTTCCCGCGCTGCACACATACTATTGACAGGTGTGTTTCGTGGTTT
        TTTGTTTTTGTTTGTTTGTTTTGAGTTGGAGGTTTGCTCTTGCTGCCCAGGCTGG
        AGTACAATGGCGCAATCTCAGCTCACCGCAATCTCTGCCTCCTGGGTTCAAGCAATTCTC
        [T,C]
        TGCCTCAGCCTCCTGAGTAGCTGGGATTACAGGCATGCGCCACCACACCCAGCTAATTTT
        GTATTTTTAGTAGACGTGGGGTTTCTCCATGTTGGTCAGGCTGGTCTCGAACTCCTGACC
        TCAGGTGATCCGCTTGCCTTAGCCTCCGAAAGTGCTGGGATTACAGGCATGAGCCACTGC
        GTTAGGCCCACTGACAAGCCTTGTATTGGCTAGCCACCAAGATTGACTTGATTATCCACC
        TTCGGGACAACTGGACAGCCTGCTTATGACTTACGCCATAGTCTGTCTCTACTAGCTCTC

8551    TACAGGCATGAGCCACTGGGTTAGGCCCACTGACAAGCCTTGTATTGGCTAGCCACCAAG
        ATTGACTTGATTATCCACCTTCGGGACAACTGGACAGCCTGCTTATGACTTACGCCATAG
        TCTGTCTCTACTAGCTCTCCTGCCCTGACTTGACCCAGCATACAACAGCCAGAGCCAGCC
        TTTTCAATATAAACCTGATCTTGCTGGCACTGCTTAAACCCTGCAGGGGCCTCGCACTGC
        TCCATGGCCCAGCCTGTCTACCCTTACCTTCTGCCCAGGCTCTGCTCATCCATTCTCTGC
        [C,T]
        TCCCACACACCTGCCCTCTGTGGGCTCCAGCCATACCATCTCTCAACTCATAAGCCAGTT
        TTTTCATACAGGCTCCCTCCATCTGGACTGGCTTCCCTGCGTGCAGTTCACTCCTGCTCT
        ACCTTTGGCTCTGCCTCCACCCATCCTCAGCCGTCTCCAGCATTACCTCCTTGGAGAATC
        CTGCCTTGACTTCCCAGCCACCCAAATATCACTACTTGGTCTGCATTCTCGTTGCAATTG
        CAGTCGCATGAGCAATTGCTGTGGTTGAGGCCCGAACTGCGCAAGTGCCTGTCTGCCATG

9269    AGGCCAGGGTCCCAGGTGCTGGCGGGGCTGGCTGCTGGGTGGGGGCAGAGAGGCAACCCC
        TCTGTTTTTTTCCCTCTCAGGGCATGATCACAAGGGCCACCCCCACACTAGCTACTACCA
        GTATGGCCTGGGCATTCTGGCCCTGTGTCTCCACCAGAAGCGGGTCCATGACAGCGTGGT
        GGACAAACTTCTGTATGCTGTGGAACCTTTCCACCAGGGCCACCATTCTGTGGGTGAGTA
        GGTCAGACCGTGCCAAGGCCAGGCTGGCACTCCCTCAGTCCCCAGGTCTGCACTGATGAC
        [G,C]
```

FIGURE 3, page 11 of 22

```
      TCCATACCCTGGCCCCCACACTCACCTTTCCTTGGGGCTCCTCCGAATCAAGTCCTTTAG
      GGACGAATTGGCGAGGGCTCATGGGTGATGCTCCAGCTGTGAGCCAGCTTTGGAGCTGGT
      AGGTGGATCTCTTGAGGCCAGGAGTTCAAGACAACGTGGTGAAACCCCATCTCTACTAAA
      AATAAAAAAGTTAGCCGGGCATGGTGGCACATGCCTGTAGTCCCAGCTACTCGGGAGGCT
      GAGGCAGGAGAATCACTTGAACCTGGGAGGCGGAGGCTGCAGTGAGTGGAGATCGCACCA

9362  GGGCCACCCCCACACTAGCTACTACCAGTATGGCCTGGGCATTCTGGCCCTGTGTCTCCA
      CCAGAAGCGGGTCCATGACAGCGTGGTGGACAAACTTCTGTATGCTGTGGAACCTTTCCA
      CCAGGGCCACCATTCTGTGGGTGAGTAGGTCAGACCGTGCCAAGGCCAGGCTGGCACTCC
      CTCAGTCCCCAGGTCTGCACTGATGACGTCCATACCCTGGCCCCCACACTCACCTTTCCT
      TGGGGCTCCTCCGAATCAAGTCCTTTAGGGACGAATTGGCGAGGGCTCATGGGTGATGCT
      [C,T]
      CAGCTGTGAGCCAGCTTTGGAGCTGGTAGGTGGATCTCTTGAGGCCAGGAGTTCAAGACA
      ACGTGGTGAAACCCCATCTCTACTAAAAATAAAAAAGTTAGCCGGGCATGGTGGCACATG
      CCTGTAGTCCCAGCTACTCGGGAGGCTGAGGCAGGAGAATCACTTGAACCTGGGAGGCGG
      AGGCTGCAGTGAGTGGAGATCGCACCACTGCCCTCCAGCCTGGGCAACAGAGTGAGTGAG
      ACTCTGTCTCAAAAAATAAAAAATAAAATAAAACTCCCCTAGTGATTCCAATGTGCAGCT

9782  GCCTGTAGTCCCAGCTACTCGGGAGGCTGAGGCAGGAGAATCACTTGAACCTGGGAGGCG
      GAGGCTGCAGTGAGTGGAGATCGCACCACTGCCCTCCAGCCTGGGCAACAGAGTGAGTGA
      GACTCTGTCTCAAAAAATAAAAAATAAAATAAAACTCCCCTAGTGATTCCAATGTGCAGC
      TAAGTTTGGAAATAGGTGGTATGGGGTCAAGTCCTCTTGGGCCTCCCTCCTCCAGTCCTT
      CTCCCTAACCTCTAGCCCTCAAGTTGCAGAGTGATCAGCCAAACCAGTTTGCCCAGAAAT
      [G,T]
      AGCAGTTTCCTGGGACACAGGATTTTCAGAGTCCAGACAAGGAAAGTCTTGGGCAGACCA
      GGTTGAGTTGGTGCCCTTAGCTGATCTGACCATGTTGCCCTTCTTCTCCAAGCCCTCCTG
      TGGTTGTCCATAGCTACAAGGGCCTGACCCTCAAGCCCCTGCCTGTCCTGGCCCCTTTGG
      CTCTCCAGCTCATTGCATGTTCTGTCCCCACTTCAAGACACAGCAGCCATGGCAGGCTT
      GGCATTCACCTGTCTGAAGCGCTCAAACTTCAACCCTGGTCGGAGACAACGGATCACCAT

11493 AAAAAAAAAAATGGAGAAGAAGGAAGCTGGACATGGTGGCTCGTGCTTATAATCCTAGCA
      CTCTGGGAAGCTGAGGCAGATGGATTGCCTGAGCCCAGGAGTTTGAGACCAGCCTGGGCA
      ACATGGTGAAACCCTGTCTCTTTACTAAAATACGAAAGATTAGCCAGGCATGGTGGTAGACA
      CCTATAATCCCAGCTACTAGGGAGGCTGAGCCACAAGAATCACTTGAACCTGGGAGACAG
      AGGTTGCAGTGAGCCGAGATCGCGCCATTGCACTCCAGCCTGGGCGACAGTGTGAGACTC
      [G,A,T]
      GTCTCCAGAAAAAACAAGAATGGATAGAGTGGAGCCAAGAAGAGGCAGGAAGAACAAAGA
      CACAGAGGTGCACAGAGTTTGGGGGAATTTTGAGGAATGGTCTTGCAAAAGAGTGGGATC
      TGGGAGAATGAGTGGGAGTGGAAAGCAGATGAATGAAGAGAAGGTGAGCGCATCAGGGTA
      ACAGAGATGCGTTGTGAACAAATGCATGTTCTAGGAAGAGCCCTCTGGAGTGCTAGGTGC
      CAGAGAGGTGGGAGGAAGGATACTGGAAGCAGAGAAACCAGTGAGGGGCCTGATCTTGGG

12260 ACAAGAAGACAAATAATCCAGGCTCTCTGTCCTCACACCAGCTGCCCGCCCCTTTCTTCC
      TGGCACAGTCATGTTGGAACCAGCTGCTGAGACCATTCCTCAGACCCAAGAGATCATCAG
      TGTCACGCTGCAGGTGCTTAGTCTCTTGCCGCCGTACAGACAGTCCATCTCTGTTCTGGC
      CGGGTCCACCGTGGAAGATGTCCTGAAGAAGGCCCATGAGTTAGGAGGATTCACGTGAGA
      CTCCCACCTCCCAGTCCTCACCCCACCCAACCTCACATGCCTGATAACAGGGTCACAGAA
      [A,G]
      AGACGGGGAACAGAGGAGAGGGTTCCCTCGGGAGAGACACTGGCCCTGCTTCTGCTTCTA
      CCTGCTCAGCTCCTTTCTTGCCCACGGTGTTATGGAAACAGGGAGCCATAGGCCAGCATT
      GTCACTGAGAGAGCAGGCTTTGGAGGCAGAGCCCCCAGTTGGAATCCCAACTCTAACCA
      GCTAGGTTCCAGGTAGGCACCCACAATTCACCGAGGAGAACAGTTGTGCCCCTTCCCTGC
      AGGGCCAGTGTGAAGAGTCCAGGAGTTAGTACACATAGAGATAGTGGCATGTGCTTTTTA

13086 GGCACGTGCCACACAACCCTGGGTAATTTTTTTTTTTTTTTTTGAGATAGGGTCTCTG
      TCTGTTGCCCAGGCTGGTCTCAAATTCCTGGGCTCAAACCATCCTCACACCTGAGGCGCT
      CAAAATATTGGGATTATAGGTGCGAGCCATCATGCTCAGCCAGAATAATAACTGGTTTTT
      TTTGTTTTTTTTTGAGACAGAGTCTCACTCTATTACCCAGGCTCTGGAGGCCCAACTCG
      TGTTTGTGTATTTGTTTATTTTTATTTATTTATTTCGAGACAGAGCCTCTCTCTTT
      [T,C]
      ACCTAGGCTGGAGTGCAGTGGCGCAATCTCGGCTCACTGCAACCTCCGTCTCCTGGGTTC
      AAGTGATTGTCCTGCCTCAGCCTCCTGAGTAGCTGGTGCTACAGGGCGCGTGCCACCATGC
      CCAGCTAATTTTTGTATTTTTAGTAGAGACAGGGTTTTACTATGTTGGCCAGCTGGTTTC
      TAACTCCTGAACTCGGGTGATCTGCCTGCCTCGGCCTCCCAAAGTGCTGGGATTACAGGC
      ATGGGCCTCCGTGCCCGGCCATGTATTTATTTAGGCAAGGTCTCTCTCTGTTATCCAGGC

13183 ACCATCCTCACACCTGAGGCGCTCAAAATATTGGGATTATAGGTGCGAGCCATCATGCTC
      AGCCAGAATAATAACTGGTTTTTTTTGTTTTTTTTTGAGACAGAGTCTCACTCTATTAC
      CCAGGCTCTGGAGGCCCAACTCGTGTTTGTGTATTTGTTTATTTTTATTTATTTATTTAT
      TTCGAGACAGAGCCTCTCTCTTTCACCTAGGCTGGAGTGCAGTGGCGCAATCTCGGCTCA
      CTGCAACCTCCGTCTCCTGGGTTCAAGTGATTGTCCTGCCTCAGCCTCCTGAGTAGCTGG
```

```
         [T,C]
         GCTACAGGCGCGTGCCACCATGCCCAGCTAATTTTTGTATTTTTAGTAGAGACAGGGTTT
         TACTATGTTGGCCAGCTGGTTTCTAACTCCTGAACTCGGGTGATCTGCCTGCCTCGGCCT
         CCCAAAGTGCTGGGATTACAGGCATGGGCCTCCGTGCCCGGCCATGTATTTATTTAGGCA
         AGGTCTCTCTCTGTTATCCAGGCTGAAGTGCAGTGGCACATTCATAGCTCACTGCAGCCT
         CAAATTATCCAAGTAACAGGGACTACAGGCATGCACCACCACACCCATCTACTTTTTTTT

21240    TCAGCTCACTGCAACCTCTGCCTCCCTGGCTTAAGCGATCCTCCCACCTCAGCCTCCTGA
         GTACGTGTGACCATAGGCCCATGGCACAAAGCCCAGCTAATTTTTTGTATTTTTAGTAGA
         AATGTGGTTTCACCATGTTGCATAGGCTGGTCTCGAACTTCTGAACTCAAGTGATCTGCC
         TGCCTTGGCCTCCCAAAGTGCTGGGATTCTAGGTATGAGCCACCCTGCTCGGCCTATAAT
         GGCACTTTCCTATCCCATTGATGAGGCTCTACTCTCATGACCTAATCATCTCCCAAAGGC
         [C,G]
         CTAAGGCCTCCTGATACCATCACCTTTGGGGTTAGGTTTTAACATATACATTTTGGGGGG
         ACACAGACATTTTAGACCATAGCACCTCCATTGAAAGGAAACATTTCTGACACCTGGCTA
         TCTCAAAGGGCCCTTTCAGTTCCCCTGCAGGCTGCATTCCCACATCACCAACAAGAGCAG
         CGACACTCACTCAGAGGTTAAATAACTTGTCCAGAGTCACAGCAGTAATGAATGACAGAG
         CTGGGGCTTGAATCCAGGCGTCCTCCTAGAGCCTGGATTCTGTGTAGTGAGTGAAAGCTG

21695    CATTCCCACATCACCAACAAGAGCAGCGACACTCACTCAGAGGTTAAATAACTTGTCCAG
         AGTCACAGCAGTAATGAATGACAGAGCTGGGGCTTGAATCCAGGCGTCCTCCTAGAGCCT
         GGATTCTGTGTAGTGAGTGAAAGCTGACTCCTGGGAGACTTCTGCGTGGTCCTGGTTCTC
         TCTCCAGACTGCACTGCGCAAGTTTCTCTTCCTGATGGTCCCTAGGGTATTACAAAGACA
         GTGGCCCTGCCTGTCAGGTGTTTTTATTACCAGATGAGGTCATGGCCTCAGGAACCCTGT
         [A,G]
         GGAAGCTGAGTTCAGAGTCTTTGAGCAGGCTTTAGGGAGGTTCCAGCTTCCCACCACCAA
         GCCCCAGGTGGATTCTTACAGACTCTAGCCTCAGGGTGGGGGGTCTGGAAGATGAGGTTG
         CGGGGTGCGATATTCTGCCCAATTCGCCCCTCCTTGCTCAATCTGTTTCTGCAGGTATTG
         CTGACTACAGACCCAAGGATGGAGAAACCATTGAGCTGAGGCTGGTTAGCTGGTAGCCCC
         TGAGCTCCCTCATCCCAGCAGCCTCGCACACTCCCTAGGCTTCTACCCTCCCTCCTGATG

22058    CCCAGGTGGATTCTTACAGACTCTAGCCTCAGGGTGGGGGTCTGGAAGATGAGGTTGCG
         GGGTGCGATATTCTGCCCAATTCGCCCCTCCTTGCTCAATCTGTTTCTGCAGGTATTGCT
         GACTACAGACCCAAGGATGGAGAAACCATTGAGCTGAGGCTGGTTAGCTGGTAGCCCCTG
         AGCTCCCTCATCCCAGCAGCCTCGCACACTCCCTAGGCTTCTACCCTCCCTCCTGATGTC
         CCTGGAACAGGAACTCGCCTGACCCTGCTGCCACCTCCTGTGCACTTTGAGCAATGCCCC
         [C,T]
         TGGGATCACCCCAGCCACAAGCCCTTCGAGGGCCCTATACCATGGCCCACCTTGGAGCAG
         AGAGCCAAGCATCTTCCCTGGGAAGTCTTTCTGGCCAAGTCTGGCCAGCCTGGCCCTGCA
         GGTCTCCCATGAAGGCCACCCCATGGTCTGATGGGCATGAAGCATCTCAGACTCCTTGGC
         AAAAAACGGAGTCCGCAGGCCGCAGGTGTTGTGAAGACCACTCGTTCTGTGGTTGGGGTC
         CTGCAAGAAGGCCTCCTCAGCCCGGGGGCTATGGCCCTGACCCCAGCTCTCCACTCTGCT

22233    CCCTGAGCTCCCTCATCCCAGCAGCCTCGCACACTCCCTAGGCTTCTACCCTCCCTCCTG
         ATGTCCCTGGAACAGGAACTCGCCTGACCCTGCTGCCACCTCCTGTGCACTTTGAGCAAT
         GCCCCCTGGGATCACCCCAGCCACAAGCCCTTCGAGGGCCCTATACCATGGCCCCACCTTG
         GAGCAGAGAGCCAAGCATCTTCCCTGGGAAGTCTTTCTGGCCAAGTCTGGCCAGCCTGGC
         CCTGCAGGTCTCCCATGAAGGCCACCCCATGGTCTGATGGGCATGAAGCATCTCAGACTC
         [C,A]
         TTGGCAAAAAACGGAGTCCGCAGGCCGCAGGTGTTGTGAAGACCACTCGTTCTGTGGTTG
         GGGTCCTGCAAGAAGGCCTCCTCAGCCCGGGGGCTATGGCCCTGACCCCAGCTCTCCACT
         CTGCTGTTAGAGTGGCAGCTCCGAGCTGGTTGTGGCACAGTAGCTGGGGAGACCTCAGCA
         GGGCTGCTCAGTGCCTGCCTCTGACAAAATTAAAGCATTGATGGCCTGTGGACCTGCTAC
         AGTGGCCTGGTGCCTCATACTCCTCAGGTGCAGGGGCAGGGACAAGAGAAGGGGAAGTA

22245    TCATCCCAGCAGCCTCGCACACTCCCTAGGCTTCTACCCTCCCTCCTGATGTCCCTGGAA
         CAGGAACTCGCCTGACCCTGCTGCCACCTCCTGTGCACTTTGAGCAATGCCCCCTGGGAT
         CACCCCAGCCACAAGCCCTTCGAGGGCCCTATACCATGGCCCACCTTGGAGCAGAGAGCC
         AAGCATCTTCCCTGGGAAGTCTTTCTGGCCAAGTCTGGCCAGCCTGGCCCTGCAGGTCTC
         CCATGAAGGCCACCCCATGGTCTGATGGGCATGAAGCATCTCAGACTCCTTGGCAAAAAA
         [C,-]
         GGAGTCCGCAGGCCGCAGGTGTTGTGAAGACCACTCGTTCTGTGGTTGGGGTCCTGCAAG
         AAGGCCTCCTCAGCCCGGGGGCTATGGCCCTGACCCCAGCTCTCCACTCTGCTGTTAGAG
         TGGCAGCTCCGAGCTGGTTGTGGCACAGTAGCTGGGGAGACCTCAGCAGGGCTGCTCAGT
         GCCTGCCTCTGACAAAATTAAAGCATTGATGGCCTGTGGACCTGCTACAGTGGCCTGGTG
         CCTCATACTCCTCAGGTGCAGGGGCAGGGACAAGAGAAGGGGAAGTAACCCCATCAGGG

22375    ACAAGCCCTTCGAGGGCCCTATACCATGGCCCACCTTGGAGCAGAGAGCCAAGCATCTTC
         CCTGGGAAGTCTTTCTGGCCAAGTCTGGCCAGCCTGGCCCTGCAGGTCTCCCATGAAGGC
         CACCCCATGGTCTGATGGGCATGAAGCATCTCAGACTCCTTGGCAAAAAACGGAGTCCGC
         AGGCCGCAGGTGTTGTGAAGACCACTCGTTCTGTGGTTGGGGTCCTGCAAGAAGGCCTCC
```

FIGURE 3, page 13 of 22

```
         TCAGCCCGGGGGCTATGGCCCTGACCCCAGCTCTCCACTCTGCTGTTAGAGTGGCAGCTC
         [C,T]
         GAGCTGGTTGTGGCACAGTAGCTGGGGAGACCTCAGCAGGGCTGCTCAGTGCCTGCCTCT
         GACAAAATTAAAGCATTGATGGCCTGTGGACCTGCTACAGTGGCCTGGTGCCTCATACTC
         CTCAGGTGCAGGGGCAGGGACAAGAGAAGGGGGAAGTAACCCCATCAGGGAGGAGTGGAG
         GGTGCCTGAGCCGCCATGTGGGCATTGGGGGAGTGATGGGAATGCCAGCAGTGATGACGT
         TGACTACTGACTGAGCACCCACTACTATGACTGAGCACTCACTCGCTAGATACTATCTTG

23042    GCCGGGCGTGGTGGCTCACGCCTGTAATCCCAGCACTTTAGGAGGCCAAGGCAGGTGGAT
         CACAAGGTCAGGAGTTTGAGATCAGCCTGGCCAACATGGTGAAACTCCATCTTTACTAAA
         AATACAAAAAATTAGCCAGGCATGGTGTTGCATGCCTGCATGCCTGTAATCCCAGTTACT
         TGGGAAGCTGAGGCAGGAGAATTGCTTGAACCCTGGAGGCGGAGGTTGTAGTGAGCCGAG
         ATCACGCCATTGCACTCCAGCTTGGGCAAGAAGAGAAACACTCTCAAAAAAAAAAAAAAA
         [A,-,T]
         CAGGAAACTGGTGCTCAAAAAGGAAAAGTGACTCACCAAGGTCACAGACTAGGCAGTGAT
         GCTGGGGGAACCTGGCTCAGGGGACACAGACCTGGCCTGGGGCAGCCTTGCAGCTCCTCC
         ACTAAAATACTGAAAATGAGGGGCTTCGATGATGGTTATAATCGTATGGCAGAGCCCCAA
         CTCAACTGGAGCCCTGGGACCCAGAAGCTAGGGTCTCACTCCCTGCTTTTCCACAAGGCA
         CCATTAGGGCATCACCCCAGGCCTCGGCAGCCACGACGCAGGGATCCTGCCTCTCATTGG

23344    AGGAAACTGGTGCTCAAAAAGGAAAAGTGACTCACCAAGGTCACAGACTAGGCAGTGATG
         CTGGGGGAACCTGGCTCAGGGGACACAGACCTGGCCTGGGGCAGCCTTGCAGCTCCTCCA
         CTAAAATACTGAAAATGAGGGGCTTCGATGATGGTTATAATCGTATGGCAGAGCCCCAAC
         TCAACTGGAGCCCTGGGACCCAGAAGCTAGGGTCTCACTCCCTGCTTTTCCACAAGGCAC
         CATTAGGGCATCACCCCAGGCCTCGGCAGCCACGACGCAGGGATCCTGCCTCTCATTGGT
         [T,C]
         GGGGGCTTAGGGGCTCTGGGCTGCCCTCTTGAAGAGGGGGTTCAGCCCAGCGAGGCACCC
         CCTATGCTGCACCCCACCAAGGTTAGGAAGAGGTCCTGTCCTCAGTGGGGCCCTCTGATG
         AACAGCCCATCAGGTCTGCGTCCACATGCCTTGGAAGAGATGGTGACATACTCAAAGTCC
         TTGAAGCCGCATATTAAACCACCTAGAGCACCATCTTCAAACATTTAGGGTCTGAGAAGA
         TAGGGGAAGTAAGCAATTTAAAACATTTCTTTATATTGGGCCAGGTGCAATGGCTCACGT

23873    GGTCTGAGAAGATAGGGGAAGTAAGCAATTTAAAACATTTCTTTATATTGGGCCAGGTGC
         AATGGCTCACGTCTGTAATCCCAGCGCTTTGGGAGGACGAGGATCACCTGAGGTCAGGAG
         TTCAAGATCAGCCTGGCCAACATGGAGAAACCCCATCTCTACTAAAAATACAAAAATTAG
         CTCAGGCGTGGTGATGTGCACCTGTAATCCTAGCTATTCAGGAGGCTGAGGCACAAGAAT
         TGCTTGAGTCAATATTGCACCACTGCACTCCAGCCTGGGCAACAGCGAGACTCTTGTCTC
         [A,-]
         AAAAAAAAAAAAGATATTTGCTGAAAAGACCCAGCCTGCCAAACTCAGGGGCAGCCAAGG
         GAGGTAGTGAAATGGAAGTTGGAGCTCAGCGCTCCCACACCTCCACTGCCCTCAGGCCTT
         CTCTGCCTCTTTCCCATCAGTCAGCTGCTTCTGGGCATGGTCCTGGCAGAGACTTGGCCT
         CCTTCCAGTTCAAGCTCCCTCTTAGATTGTGTCCCACGCCACTGAGTCTTTGGGACACTG
         GGTCAGATGTCTAGTCTGGCACAATTGGCAGGAATCCCAAGAAACAGTGTGAGTGAGGGG

24764    ATAGCTGGGATTACAGGTGTGCACCACCATGCCCAGCCTAATTTTTGTATTATTAGTAGA
         GATGGGGTTTCACCATGTTGTCCAGGCTGGTCATGAACTCCTGACCTCAAGTGATCCACC
         CGCTTTGGCCTCCCAAAGTGCTGGGATTACAAGCATGAGCCACAGTGCCTGGCCTGACCC
         TGCTCTTTTGAAAGACCATTCCCCCAAATTCTGTGCACCTGTGTGCCTTTCTTCTCTCTG
         CCTCCTCTCAGCTCTGCCCCGCTCTCCTCCCTTCTCCTCTGGCAAATCCCACTCATCTCT
         [G,T]
         GAAGCCCTTCTTCCAGGGGAAGCCCTGATCATGCTGCTTTCTCCTGTGGGAGGGATGAAG
         GACGTGGCCCACGGAGTTTGTTTTGTTTTGAGATGGAGTTTTGCTCATGTTGCCC
         AGGCTGGGGTACAATGGTACGATCTCAGCTCACTGCAACCTCTACGTCCCGGGTTCAAGC
         GGTTCTCCTGCCTTAGCCTCCCCAGTAGCTGGGATTACTGGCATGAACCACCACACCTGG
         CTAATTTTGTGTTTTTAGTAGAGATGGGGTTTCTTCATGTTGGTCAGGCTGGTCTCGAAC

24939    GACCCTGCTCTTTTGAAAGACCATTCCCCCAAATTCTGTGCACCTGTGTGCCTTTCTTCT
         CTCTGCCTCCTCTCAGCTCTGCCCCGCTCTCCTCCCTTCTCCTCTGGCAAATCCCACTCA
         TCTCTTGAAGCCCTTCTTCCAGGGGAAGCCCTGATCATGCTGCTTTCTCCTGTGGGAGGG
         ATGAAGGACGTGGCCCACGGAGTTTGTTTTGTTTTGTTTTGAGATGGAGTTTTGCTCATG
         TTGCCCAGGCTGGGGTACAATGGTACGATCTCAGCTCACTGCAACCTCTACGTCCCGGGT
         [T,C]
         CAAGCGGTTCTCCTGCCTTAGCCTCCCCAGTAGCTGGGATTACTGGCATGAACCACCACA
         CCTGGCTAATTTTGTGTTTTTAGTAGAGATGGGGTTTCTTCATGTTGGTCAGGCTGGTCT
         CGAACTCCCAACCTCAGGTGATCTGCCTGCCTCGGCCTCCCAAAGTACTGGGATTACAGG
         GTTGAGCCACTGTGCCTGGCCCAGGCCCACGGAGTTTTAAGAGGCTTCCTGTGGCAGTGG
         CATCCAGACGGAGTGCAGAAACTCAAAGTTGAAGGCCAGAAGCTCAGGGAAGGGGGAGTG

24945    GCTCTTTTGAAAGACCATTCCCCCAAATTCTGTGCACCTGTGTGCCTTTCTTCTCTCTGC
         CTCCTCTCAGCTCTGCCCCGCTCTCCTCCCTTCTCCTCTGGCAAATCCCACTCATCTCTT
         GAAGCCCTTCTTCCAGGGGAAGCCCTGATCATGCTGCTTTCTCCTGTGGGAGGGATGAAG
```

```
         GACGTGGCCCACGGAGTTTGTTTTGTTTTGTTTTGAGATGGAGTTTTGCTCATGTTGCCC
         AGGCTGGGGTACAATGGTACGATCTCAGCTCACTGCAACCTCTACGTCCCGGGTTCAAGC
         [G,A]
         GTTCTCCTGCCTTAGCCTCCCCAGTAGCTGGGATTACTGGCATGAACCACCACACCTGGC
         TAATTTTGTGTTTTTAGTAGAGATGGGGTTTCTTCATGTTGGTCAGGCTGGTCTCGAACT
         CCCAACCTCAGGTGATCTGCCTGCCTCGGCCTCCCAAAGTACTGGGATTACAGGGTTGAG
         CCACTGTGCCTGGCCCAGGCCCACGGAGTTTTAAGAGGCTTCCTGTGGCAGTGGCATCCA
         GACGGAGTGCAGAAACTCAAAGTTGAAGGCCAGAAGCTCAGGGAAGGGGGAGTGTGAGTT

25092    ATCATGCTGCTTTCTCCTGTGGGAGGGATGAAGGACGTGGCCCACGGAGTTTGTTTTGTT
         TTGTTTTGAGATGGAGTTTTGCTCATGTTGCCCAGGCTGGGGTACAATGGTACGATCTCA
         GCTCACTGCAACCTCTACGTCCCGGGTTCAAGCGGTTCTCCTGCCTTAGCCTCCCCAGTA
         GCTGGGATTACTGGCATGAACCACCACACCTGGCTAATTTTGTGTTTTTAGTAGAGATGG
         GGTTTCTTCATGTTGGTCAGGCTGGTCTCGAACTCCCAACCTCAGGTGATCTGCCTGCCT
         [C,T]
         GGCCTCCCAAAGTACTGGGATTACAGGGTTGAGCCACTGTGCCTGGCCCAGGCCCACGGA
         GTTTTAAGAGGCTTCCTGTGGCAGTGGCATCCAGACGGAGTGCAGAAACTCAAAGTTGAA
         GGCCAGAAGCTCAGGGAAGGGGGAGTGTGAGTTGAGGAGTCTCTTGGCTGCCAGGGCCAG
         AAACCGAACTCCAAGCCTCTCCACAACAGCGGGTGTAGAGCATGTAGAATCAGAGAGGAG
         GCTGAGCCATGCAGCCCCGAGAAGAGGGGAATGCCACTGAGCCACAGAGACCCAGTGCCA

25428    AGTGCAGAAACTCAAAGTTGAAGGCCAGAAGCTCAGGGAAGGGGGAGTGTGAGTTGAGGA
         GTCTCTTGGCTGCCAGGGCCAGAAACCGAACTCCAAGCCTCTCCACAACAGCGGGTGTAG
         AGCATGTAGAATCAGAGAGGAGGCTGAGCCATGCAGCCCCGAGAAGAGGGGAATGCCACT
         GAGCCACAGAGACCCAGTGCCACTGCCAGGTGTCTCTGCCTCCACTTCCCATGACCC
         [T,G]
         GCCTGTCTCTGTATGCAGGCTTCACCCTCTCTCGTTGTACATTGTACACATTCTAGGTGA
         CACCAGCAGCTTCTGATTCTCATCTCCCATAACATCAGCCCCCCAGAGAGGGGACAACTG
         CTGAGCTGATAACATAATAGATGCCCCTTTCCTGGAGGCCATGGTCATGGTCAGCGTGGA
         GAGGATGAAGCCTGAGCAGGCAGGATCGGGGGTCTAGAGGGGAAGGAGGTGGAAGTT

25513    GGCCAGAAGCTCAGGGAAGGGGGAGTGTGAGTTGAGGAGTCTCTTGGCTGCCAGGGCCAG
         AAACCGAACTCCAAGCCTCTCCACAACAGCGGGTGTAGAGCATGTAGAATCAGAGAGGAG
         GCTGAGCCATGCAGCCCCGAGAAGAGGGGAATGCCACTGAGCCACAGAGACCCAGTGCCA
         CTGCCAGGTGTCTCTGCCTCCACTTCCCATGACCCGGCCTGTCTCTGTATGCAGGCTTCA
         CCCTCTCTCGTTGTACATTGTACACATTCTAGGTGACACCAGCAGCTTCTGATTCTCATC
         [C,T]
         CCCATAACATCAGCCCCCCAGAGAGGGGACAACTGCTGAGCTGATAACATAATAGATGCC
         CCTTTCCTGGAGGCCATGGTCATGGTCAGCGTGGAGAGGATGAAGCCTGAGCAGGCAGGA
         TCGGGGGTCTAGAGGGGAAGGAGGTGGAAGTTGAGATCACAGACCTGTGGTCAGGTGGCC
         TGGGAAGGGTTTGACGAGTGTCGGCCCAAAGAGCTTGGAAGGGATTTTGCTGCTGTGGGT
         GAGCACTGCCTCTCCCCTTAGGGACAACAGCCACCTCTTCTCTCCCCATTTGCCTTTCCC

25684    CCAGTGCCACTGCCAGGTGTCTCTGCCTCCACTTCCCATGACCCGGCCTGTCTCTGTATG
         CAGGCTTCACCCTCTCTCGTTGTACATTGTACACATTCTAGGTGACACCAGCAGCTTCTG
         ATTCTCATCTCCCATAACATCAGCCCCCCAGAGAGGGGACAACTGCTGAGCTGATAACAT
         AATAGATGCCCCTTTCCTGGAGGCCATGGTCATGGTCAGCGTGGAGAGGATGAAGCCTGA
         GCAGGCAGGATCGGGGGTCTAGAGGGGAAGGAGGTGGAAGTTGAGATCACAGACCTGTGG
         [C,T]
         CAGGTGGCCTGGGAAGGGTTTGACGAGTGTCGGCCCAAAGAGCTTGGAAGGGATTTTGCT
         GCTGTGGGTGAGCACTGCCTCTCCCCTTAGGGACAACAGCCACCTCTTCTCTCCCCATTT
         GCCTTTCCCTTCTGTAGATATGAAACACAGGCCTCCTTGTCAGGCCCCTACTTAACCTCC
         GTGATGGGGAAAGCGGCCGGAGAAAGGGAGTTCTGGCAGCTTCTCCGAGACCCCAACACC
         CCACTGTTGCAAGGTGAGTCATGGCCTGACACTCTGGATGTGTCCCCTACCCCAAGCTTA

26165    GTGATGGGGAAAGCGGCCGGAGAAAGGGAGTTCTGGCAGCTTCTCCGAGACCCCAACACC
         CCACTGTTGCAAGGTGAGTCATGGCCTGACACTCTGGATGTGTCCCCTACCCCAAGCTTA
         CTCAGCCAAGAGGCTTCATCAACTCACCCCAGCTTTCCCTAGCACCCTCCTGGGCCACAC
         CTTCACAAAATCACTGATGCTCAAAGTTGGATATAATATATTGAACTGAAGCCTTAGCAT
         TTTTATGCAAGTTACTGTGGAAATTCTAGGAAACCAGACAGATTACAAAAAAAAAAAAAA
         [A,-]
         CTAGAAGAAAATTAACATCACCTAGGATATACTACCTAGGAATAACGTCTTTTATTTTGA
         GATGGAGTTTCGCTCTTGTTGCCCAGGCTGGAGTGCAGCGGTATGATCTCGGCTCGCTGC
         AACCTCCGCCTCCTGGGTTCATGTGATTCTTCCACCTCGGCCTTCCTAGAGCCCAAGTGG
         TCTGCCTGCCTCTGCCTCCCAAAGTTCTGGGATTACAGGCATGAGCCACCGCACCCAGCC
         AAAATTACTTAACTTTTCTTCTAGATACTTTTTAAAAATATGGCAGTAAGTTTTTCATAA
```

FIGURE 3, page 15 of 22

Isoform 2:

FEATURES:

| | |
|---|---|
| Exon: | 2132-2195 |
| Intron: | 2196-5670 |
| Exon: | 5671-5863 |
| Intron: | 5864-7672 |
| Exon: | 7673-7761 |
| Intron: | 7762-9149 |
| Exon: | 9150-9302 |
| Intron: | 9303-10101 |
| Exon: | 10102-10274 |
| Intron: | 10275-10399 |
| Exon: | 10400-10586 |
| Intron: | 10587-12128 |
| Exon: | 12129-12294 |
| Intron: | 12295-25922 |
| Exon: | 25923-26040 |

Allelic Variants (SNPs):

| DNA Position | Major | Minor | Domain | Protein Position | Major | Minor |
|---|---|---|---|---|---|---|
| 1022 | C | T | Beyond ORF(5') | | | |
| 1882 | C | T | Beyond ORF(5') | | | |
| 1951 | G | A | Beyond ORF(5') | | | |
| 2940 | A | G | Intron | | | |
| 3831 | G | A | Intron | | | |
| 6732 | G | A | Intron | | | |
| 7558 | G | A | Intron | | | |
| 7931 | T | A | Intron | | | |
| 8190 | T | C | Intron | | | |
| 8652 | C | T | Intron | | | |
| 9370 | G | C | Intron | | | |
| 9463 | C | T | Intron | | | |
| 9883 | G | T | Intron | | | |
| 11594 | G | A T | Intron | | | |
| 12361 | A | G | Intron | | | |
| 13187 | T | C | Intron | | | |
| 13284 | T | C | Intron | | | |
| 21341 | C | G | Intron | | | |
| 21796 | A | G | Intron | | | |
| 22159 | C | T | Intron | | | |
| 22334 | C | A | Intron | | | |
| 22346 | C | - | Intron | | | |
| 22476 | C | T | Intron | | | |
| 23143 | A | - T | Intron | | | |
| 23445 | T | C | Intron | | | |
| 23974 | A | - | Intron | | | |
| 24865 | G | T | Intron | | | |
| 25040 | T | C | Intron | | | |
| 25046 | G | A | Intron | | | |
| 25193 | C | T | Intron | | | |
| 25529 | T | G | Intron | | | |
| 25614 | C | T | Intron | | | |
| 25785 | C | T | Intron | | | |
| 26266 | A | - | Beyond ORF(3') | | | |

Context:
DNA
Position

1022   TTGGAGATATTTTAAGGTCATAGTGTCTTCACAAATTGAGCTGAAAGGGAACTGTTAGGA
       TGATCTTGCCTAACCCTCTCATCTCACACAGGAAGAACTATTTTAAACTCGAGAGGTTAA
       GTGACCTGGCCAAAGTCACACAGCCACCACTAGTTAACTCGTATACATTGATTCTCCTGT
       GGGGCTGGGCAGATGAGGAATCTTTTGTTCTCTTCCCTGTTTGCAGAGATTTTTTTTGAG
       GTTACTTTCCGAGTTCTGGCAAGTACCCCTGCTTCTGGTAGCTTTGTGTCTCGATTCAAT
       [C,T]
       TCATTCTTTTTATTTTATTTTATTTTTGAGACAGGGTCTCACTTTGTCACCCAAGCTGGA

```
       GTGCAGTGGTGTAATCTTGGCTCACTGTAGCCTCCACCTCTTGGGTTCAAGCGATCCTCC
       TGCCTCAGCCCCCCAAGTAGCTGGGATTACAGACGTCTGCCACCACGCCAGGCTAATTTA
       TGGTTTTTTGTATGTGTTTTTTGTGTTTTTGTAGAGACAGTGTTTCCCCATGTTGCCCAG
       GCTGGTCTCCAACTCCTGAGCTCAAGTGATCTGCCCGCCTCAGCCTTTCAAAGTGCTAGG

1882   ACAGCTGACTCCAGCAATGCTGCTCACGTGACCACTGCAGCTGCAGCTCCCGTTCCACTC
       CTTGTCCTGGGCTAGGTGGGCACTACCAGGGGCTCCTTTGGTAAGGAGTACCGGGTAGGC
       ACCCGGTCCTGCCAATCCACCACTGGAACAGCTGGGGGGACAGCAGACAGGCACGGTCGG
       ACAGACTTGACAGATCAGGCATCAGGCCCTCTGCGCTGGTCCCGGGCTCTTTAAGCAGGA
       ACGTGAATGGCCTCAAGATGTCTCACATGGTCCCACTAGCCCTCCTCCTCCCTTTGTTCC
       [C,T]
       TACCTCCAGGAGGGCTGGTCTGCCCTTCCTTCCTCTGTTCTTTGGCCTTATGTTCCCCGC
       CACCACAGGCCTTCCCCCGCCCCACCCCTCTGCAGACTTAGCCGTGCATTGCAGGCATGG
       AGGATTAATCAGTGACAGGAAGCTGCGTCTCTCGGAGCGGTGACCAGCTGTGGTCAGGAG
       AGCCTCAGCAGGGCCAGCCCCAGGAGTCTTTCCCGATTCTTGCTCACTGCTCACCCACCT
       GCTGCTGCCATGAGGCACCTTGGGGCCTTCCTCTTCCTTCTGGGGGTCCTGGGGGCCCTC

1951   GGCTAGGTGGGCACTACCAGGGGCTCCTTTGGTAAGGAGTACCGGGTAGGCACCCGGTCC
       TGCCAATCCACCACTGGAACAGCTGGGGGGACAGCAGACAGGCACGGTCGGACAGACTTG
       ACAGATCAGGCATCAGGCCCTCTGCGCTGGTCCCGGGCTCTTTAAGCAGGAACGTGAATG
       GCCTCAAGATGTCTCACATGGTCCCACTAGCCCTCCTCCTCCCTTTGTTCCCTACCTCCA
       GGAGGGCTGCTCTGCCCTTCCTTCCTCTGTTCTTTGGCCTTATGTTCCCCGCCACCACAG
       [G,A]
       CCTTCCCCCGCCCCACCCCTCTGCAGACTTAGCCGTGCATTGCAGGCATGGAGGATTAAT
       CAGTGACAGGAAGCTGCGTCTCTCGGAGCGGTGACCAGCTGTGGTCAGGAGAGCCTCAGC
       AGGGCCAGCCCCAGGAGTCTTTCCCGATTCTTGCTCACTGCTCACCCACCTGCTGCTGCC
       ATGAGGCACCTTGGGGCCTTCCTCTTCCTTCTGGGGGTCCTGGGGGCCCTCACTGAGATG
       TGTGGTGAGTAACTCGCCTCTATCCTGTGCCTCTTTCCTCCTGGGTCCTTAGTGGGGTGG

2940   AACATAGGGAGACCCCATCTCTACAAAAAATAAAAAAAATTAAAAAATAGCTGGGCATGG
       GGAAGACTTTCTGAAGACCAAGAGGACACATGGGAGCTGAAACTCGAAGGAAGAAAAGGA
       GCTGGCAGGAAAGGAGTGGGGGACACACATTCTAGGCAGCAGGAAGTGAGCCTTCGGAGG
       TCCTGCCTGCTCCAGCTCTGTGCCCCAAGGGGTCTCTTGGAGCACAGTCTCCTGGGACCT
       GTCTATGAGTCTGAGCTTAGAGGCTCAGGGCTGCTCCTTCAGACAGGAGGCAGAAGGCAG
       [A,G]
       CTTTGGGAACTTTGGGCCGCCCACGCGCCTTTTCTCCTCCTCTGCACCTAGGATTACGTT
       GAGCAATACACTTTCACCCCCATGGTCTCTTGAGACCCTGGGGAAACCCTGAGAGGTGGG
       TGCAGTCATGTCCAGGTGTCAAGTGAAGAAGTCGAGGGTTGGAGGGGCTGAGTGACCCAC
       TCAGGGTGCTCCACCTTTTCCAGAGCTTTGCTGAACTTAGTTTTTAGAACTTGAAGCCTC
       GTTTGTTTTCGTTTTGTTTTTTGTTGAGAGAGGTTCTCCCTCTGTTGCCCAGGCTGGAGT

3831   GACACCTCAGGTCTGGGCCCAGGAACCCCAGCTCTTGGTTCATGTCCGGACAGTCCCCAG
       GGGAGTTCTGGGTTCAACCAGCAAGAGCTCTTCCTCCTGGCTGATCTGGTCCTCAGCCTT
       GGACAGTTAGTCCATTAACCTGACCCCACAGGAGCCCCAATCCCTTGGGGTCTGGGGAAT
       CTTGAACTGGGGTTTGGGGTGCAAATATCTGCACTGAGTCACTTAATTGCACCCAGCCTC
       ATTCCTTTATCTGTAAAGTGGGCTAAGAATGCTCCCCTGCCTTCCTCCTCGGTGTAGTAC
       [G,A]
       AGGAAGGATCCCATGACACCTGCTCTCCCAGTTTAAAGCTCTATATGTATGTTGTGAAAT
       TGACAGGGATCGCTGCACAAACGCTAATGCAAAGTGGGCTCCTGTGCTTCCTTTTCTCTT
       TCTTCTTCTTTTTTTTTTTTTAATTTTCTTCTAGAGATGAGGTCTCACTATATTGCCCA
       GGGTTGGTTTCAAACTCCTAGGGTCAAGCGATCCTCCCACCTTGGCCTCCCAAACTGCTG
       GTATTACAGGCGTGAGCCACTCTGTCTGGCTCCTATGCTTGTGAATGTCAACAGCAATCA

6732   TGAATAGCTGGGATTACAGGCGTGTGCCACCATGCCCAGCTGATTTTTGTATTTTTGGTA
       GAGATAGGGTTTCACCATGTTGGCCAGGCTGGTCTTGAACTCCTGACCTCAGGTGATCCG
       CCTGTCTTGGCTTCCCAAAGTGTTGGGATTATAGGCATGAGCCACTGCACCAATCCAAAA
       GCAGCATCTTTGTGCTCCCTTTTCAAGAGGCATCACAGAGAGGCCTGTTTTGGGGTTTGA
       ATGAGAGGCGAAGAATCAGCCATGGAGTGCCTCTTTCTCAGACTCCCTCTTGAGAAGTGG
       [G,A]
       TGCAGGGGTGGAGAGAAAAGAAGACTAGGCATAGTGGCTCATACCTGTAATCCCAACATT
       TTGGGAGGCTGAGGCAGGAAGATTGCTTGAGCTCAGGAGTTTGAGACCAGCCTAGGCAAC
       ATAGTGAGACCACATCTCTTAAAAAAAAGAAAAAGAAAAAAAATGAGCCAGGTGTAGTGA
       CTCATGCCTGTGGTCCCCACTTCTCCGGAGGCAAAGGTGGGAGGATCTTTTGAGGCTGAG
       AAATCGAGGCTACAGTGAGCCATGGTGGCACCACTGCACTCCAGCCTGGGAGACAGAGAG

7558   AAGAATCGCTTGAACTCGGGAGGCGGAGGTTGCAGTGAGCTGAGAACATGCCACTGCACT
       CCAGCCTGGGCAACAAGAGCGAAACTCTGTCTCAAAGAAAATAAATAAATAAAATAAAAA
       AATAAAAAAGGAGGGGGCATATGGGTGAAGTATGGACAAAATAGTGGGGCAGGCACAGAT
       GATCTGGACACAGGAGCCCTTGGAGTTTATTCTTGAATCTAACTGTTCATCTTTATTAAA
       TATTTGTGGCATACACCTCACAACAACATAGCCAACACACCTCCTTTTGGAGCTTTTATC
       [G,A]
```

```
         AAGTTTCCCACTGTTAAGATTTTTTCCCGCTTTGTGATGCGGGTGGGGTGGGTGCTGTAA
         GCAGGCTTACGGGGTGGCAGTTTCTCACAAAGGCATTAACTGGCCTTGTCCTAGGTCTGC
         CTTCAGCGAGGATGACGGTGACTGCCAGGGCAAGCCTTCCATGGGCCAGCTGGCCCTCTA
         CCTGCTCGCTCTCAGAGCCAACTGTGAGTTTGTCAGGGGCCACAAGGGGGACAGGCTGGT
         CTCACAGCTCAAATGGTTCCTGGAGGATGAGAAGAGAGCCATTGGTGAGCAGACACCATC

7931     GGTGGCAGTTTCTCACAAAGGCATTAACTGGCCTTGTCCTAGGTCTGCCTTCAGCGAGGA
         TGACGGTGACTGCCAGGGCAAGCCTTCCATGGGCCAGCTGGCCCTCTACCTGCTCGCTCT
         CAGAGCCAACTGTGAGTTTGTCAGGGGCCACAAGGGGGACAGGCTGGTCTCACAGCTCAA
         ATGGTTCCTGGAGGATGAGAAGAGAGCCATTGGTGAGCAGACACCATCCGCTGGGGGTGG
         GGAGCAGCTGGGAGGGCTCATCAGATGATATTCTCCAATGAGAATCAGAACTTTGGGTTT
         [T,A]
         CTCCCCAGGCGTCTTTCCCACCATCCATTCTGCCCATCTCACTGCCTACGTAGAGGCTCG
         AACCTGTCCCCATAGCCATCCTTGACCCAGCTTTTCCCGCGCTGCACACATACTATTGAC
         AGGTGTGTTTCGTGGTTTTTTGTTTTTTGTTTGTTTGTTTGTTTTGAGTTGGAGGTTTGC
         TCTTGCTGCCCAGGCTGGAGTACAATGGCGCAATCTCAGCTCACCGCAATCTCTGCCTCC
         TGGGTTCAAGCAATTCTCTTGCCTCAGCCTCCTGAGTAGCTGGGATTACAGGCATGCGCC

8190     ATCAGATGATATTCTCCAATGAGAATCAGAACTTTGGGTTTTCTCCCCAGGCGTCTTTCC
         CACCATCCATTCTGCCCATCTCACTGCCTACGTAGAGGCTCGAACCTGTCCCCATAGCCA
         TCCTTGACCCAGCTTTTCCCGCGCTGCACACATACTATTGACAGGTGTGTTTCGTGGTTT
         TTTGTTTTTTGTTTGTTTGTTTGTTTTGAGTTGGAGGTTTGCTCTTGCTGCCCAGGCTGG
         AGTACAATGGCGCAATCTCAGCTCACCGCAATCTCTGCCTCCTGGGTTCAAGCAATTCTC
         [T,C]
         TGCCTCAGCCTCCTGAGTAGCTGGGATTACAGGCATGCGCCACCACACCCAGCTAATTTT
         GTATTTTTAGTAGACGTGGGGTTTCTCCATGTTGGTCAGGCTGGTCTCGAACTCCTGACC
         TCAGGTGATCCGCTTGCCTTAGCCTCCGAAAGTGCTGGGATTACAGGCATGAGCCACTGC
         GTTAGGCCCACTGACAAGCCTTGTATTGGCTAGCCACCAAGATTGACTTGATTATCCACC
         TTCGGGACAACTGGACAGCCTGCTTATGACTTACGCCATAGTCTGTCTCTACTAGCTCTC

8652     TACAGGCATGAGCCACTGCGTTAGGCCCACTGACAAGCCTTGTATTGGCTAGCCACCAAG
         ATTGACTTGATTATCCACCTTCGGGACAACTGGACAGCCTGCTTATGACTTACGCCATAG
         TCTGTCTCTACTAGCTCTCCTGCCCTGACTTGACCCAGCATACAACAGCCAGAGCCAGCC
         TTTTCAATATAAACCTGATCTTGCTGGCACTGCTTAAACCCTGCAGGGGCCTCGCACTGC
         TCCATGGCCCAGCCTGTCTACCCTTACCTTCTGCCCAGGCTCTGCTCATCCATTCTCTGC
         [C,T]
         TCCCACACACCTGCCCTCTGTGGGCTCCAGCCATACCATCTCTCAACTCATAAGCCAGTT
         TTTTCATACAGGCTCCCTCCATCTGGACTGGCTTCCCTGCGTGCAGTTCACTCCTGCTCT
         ACCTTTGGCTCTGCCTCCACCCATCCTCAGCCGTCTCCAGCATTACCTCCTTGGAGAATC
         CTGCCTTGACTTCCCAGCCACCCAAATATCACTACTTGGTCTGCATTCTCGTTGCAATTG
         CAGTCGCATGAGCAATTGCTGTGGTTGAGGCCCGAACTGCGCAAGTGCCTGTCTGCCATG

9370     AGGCCAGGGTCCCAGGTGCTGGCGGGGCTGGCTGCTGGGTGGGGGCAGAGAGGCCAACCCC
         TCTGTTTTTTTCCCTCTCAGGGCATGATCACAAGGGCCACCCCCACACTAGCTACTACCA
         GTATGGCCTGGGCATTCTGGCCCTGTGTCTCCACCAGAAGCGGGTCCATGACAGCGTGGT
         GGACAAACTTCTGTATGCTGTGGAACCTTTCCACCAGGGCCACCATTCTGTGGGTGAGTA
         GGTCAGACCGTGCCAAGGCCAGGCTGGCACTCCCTCAGTCCCCAGGTCTGCACTGATGAC
         [G,C]
         TCCATACCCTGGCCCCCACACTCACCTTTCCTTGGGGCTCCTCCGAATCAAGTCCTTTAG
         GGACGAATTGGCGAGGGCTCATGGGTGATGCTCCAGCTGTGAGCCAGCTTTGGAGCTGGT
         AGGTGGATCTCTTGAGGCCAGGAGTTCAAGACAACGTGGTGAAACCCCATCTCTACTAAA
         AATAAAAAAGTTAGCCGGGCATGGTGGCACATGCCTGTAGTCCCAGCTACTCGGGAGGCT
         GAGGCAGGAGAATCACTTGAACCTGGGAGGCGGAGGCTGCAGTGAGTGGAGATCGCACCA

9463     GGGCCACCCCCACACTAGCTACTACCAGTATGGCCTGGGCATTCTGGCCCTGTGTCTCCA
         CCAGAAGCGGGTCCATGACAGCGTGGTGGACAAACTTCTGTATGCTGTGGAACCTTTCCA
         CCAGGGCCACCATTCTGTGGGTGAGTAGGTCAGACCGTGCCAAGGCCAGGCTGGCACTCC
         CTCAGTCCCCAGGTCTGCACTGATGACGTCCATACCCTGGCCCCCACACTCACCTTTCCT
         TGGGGCTCCTCCGAATCAAGTCCTTTAGGGACGAATTGGCGAGGGCTCATGGGTGATGCT
         [C,T]
         CAGCTGTGAGCCAGCTTTGGAGCTGGTAGGTGGATCTCTTGAGGCCAGGAGTTCAAGACA
         ACGTGGTGAAACCCCATCTCTACTAAAAATAAAAAAGTTAGCCGGGCATGGTGGCACATG
         CCTGTAGTCCCAGCTACTCGGGAGGCTGAGGCAGGAGAATCACTTGAACCTGGGAGGCGG
         AGGCTGCAGTGAGTGGAGATCGCACCACTGCCCTCCAGCCTGGGCAACAGAGTGAGTGAG
         ACTCTGTCTCAAAAAATAAAAAATAAAATAAAACTCCCCTAGTGATTCCAATGTGCAGCT

9883     GCCTGTAGTCCCAGCTACTCGGGAGGCTGAGGCAGGAGAATCACTTGAACCTGGGAGGCG
         GAGGCTGCAGTGAGTGGAGATCGCACCACTGCCCTCCAGCCTGGGCAACAGAGTGAGTGA
         GACTCTGTCTCAAAAAATAAAAAATAAAATAAAACTCCCCTAGTGATTCCAATGTGCAGC
         TAAGTTTGGAAATAGGTGGTATGGGGTCAAGTCCTCTTGGGCCTCCCTCCTCCAGTCCTT
         CTCCCTAACCTCTAGCCCTCAAGTTGCAGAGTGATCAGCCAAACCAGTTTGCCCAGAAAT
```

FIGURE 3, page 18 of 22

```
       [G,T]
       AGCAGTTTCCTGGGACACAGGATTTTCAGAGTCCAGACAAGGAAAGTCTTGGGCAGACCA
       GGTTGAGTTGGTGCCCTTAGCTGATCTGACCATGTTGCCCTTCTTCTCCAAGCCCTCCTG
       TGGTTGTCCATAGCTACAAGGGCCTGACCCTCAAGCCCCTGCCTGTCCTGGCCCCTTTGG
       CTCTCCAGCTCATTGCATGTTCTGTCCCCCACTTCAAGACACAGCAGCCATGGCAGGCTT
       GGCATTCACCTGTCTGAAGCGCTCAAACTTCAACCCTGGTCGGAGACAACGGATCACCAT

11594  AAAAAAAAAAATGGAGAAGAAGGAAGCTGGACATGGTGGCTCGTGCTTATAATCCTAGCA
       CTCTGGGAAGCTGAGGCAGATGGATTGCCTGAGCCCAGGAGTTTGAGACCAGCCTGGGCA
       ACATGGTGAAACCCTGTCTTTACTAAAATACGAAAGATTAGCCAGGCATGGTGGTAGACA
       CCTATAATCCCAGCTACTAGGGAGGCTGAGCCACAAGAATCACTTGAACCTGGGAGACAG
       AGGTTGCAGTGAGCCGAGATCGCGCCATTGCACTCCAGCCTGGGCGACAGTGTGAGACTC
       [G,A,T]
       GTCTCCAGAAAAAACAAGAATGGATAGAGTGGAGCCAAGAAGAGGCAGGAAGAACAAAGA
       CACAGAGGTGCACAGAGTTTGGGGGAATTTTGAGGAATGGTCTTGCAAAAGAGTGGGATC
       TGGGAGAATGAGTGGGAGTGGAAAGCAGATGAATGAAGAGAAGGTGAGCGCATCAGGGTA
       ACAGAGATGCGTTGTGAACAAATGCATGTTCTAGGAAGAGCCCTCTGGAGTGCTAGGTGC
       CAGAGAGGTGGGAGGAAGGATACTGGAAGCAGAGAAACCAGTGAGGGGCCTGATCTTGGG

12361  ACAAGAAGACAAATAATCCAGGCTCTCTGTCCTCACACCAGCTGCCCGCCCCTTTCTTCC
       TGGCACAGTCATGTTGGAACCAGCTGCTGAGACCATTCCTCAGACCCAAGAGATCATCAG
       TGTCACGCTGCAGGTGCTTAGTCTCTTGCCGCCGTACAGACAGTCCATCTCTGTTCTGGC
       CGGGTCCACCGTGGAAGATGTCCTGAAGAAGGCCCATGAGTTAGGAGGATTCACGTGAGA
       CTCCCACCTCCCAGTCCTCACCCCACCCAACCTCACATGCCTGATAACAGGGTCACAGAA
       [A,G]
       AGACGGGGAACAGAGGAGAGGGTTCCCTCGGGAGAGACACTGGCCCTGCTTCTGCTTCTA
       CCTGCTCAGCTCCTTTCTTGCCCACGGTGTTATGGAAACAGGGAGCCATAGGCCAGCATT
       GTCACTGAGAGAGCAGGCTTTGGAGGCAGAGCCCCCCAGTTGGAATCCCAACTCTAACCA
       GCTAGGTTCCAGGTAGGCACCCACAATTCACCGAGGAGAACAGTTGTGCCCCTTCCCTGC
       AGGGCCAGTGTGAAGAGTCCAGGAGTTAGTACACATAGAGATAGTGGCATGTGCTTTTTA

13187  GGCACGTGCCACACAACCCTGGGTAATTTTTTTTTTTTTTTTTGAGATAGGGTCTCTG
       TCTGTTGCCCAGGCTGGTCTCAAATTCCTGGCCTCAAACCATCCTCACACCTGAGGCGCT
       CAAAATATTTGGGATTATAGGTGCGAGCCATCATGCTCAGCCAGAATAATAACTGGTTTTT
       TTTGTTTTTTTTTTGAGACAGAGTCTCACTCTATTACCCAGGCTCTGGAGGCCCAACTCG
       TGTTTGTGTATTTGTTTATTTTTATTTATTTATTTATTTCGAGACAGAGCCTCTCTCTTT
       [T,C]
       ACCTAGGCTGGAGTGCAGTGGCGCAATCTCGGCTCACTGCAACCTCCGTCTCCTGGGTTC
       AAGTGATTGTCCTGCCTCAGCCTCCTGAGTAGCTGGTGCTACAGGCGCGTGCCACCATGC
       CCAGCTAATTTTTGTATTTTTAGTAGAGACAGGGTTTTACTATGTTGGCCAGCTGGTTTC
       TAACTCCTGAACTCGGGTGATCTGCCTGCCTCGGCCTCCCAAAGTGCTGGGATTACAGGC
       ATGGGCCTCCGTGCCCGGCCATGTATTTATTTAGGCAAGGTCTCTCTCTGTTATCCAGGC

13284  ACCATCCTCACACCTGAGGCGCTCAAAATATTGGGATTATAGGTGCGAGCCATCATGCTC
       AGCCAGAATAATAACTGGTTTTTTTTGTTTTTTTTTGAGACAGAGTCTCACTCTATTAC
       CCAGGCTCTGGAGGCCCAACTCGTGTTTGTGTATTTGTTTATTTTTATTTATTTATTTAT
       TTCGAGACAGAGCCTCTCTCTTTCACCTAGGCTGGAGTGCAGTGGCGCAATCTCGGCTCA
       CTGCAACCTCCGTCTCCTGGGTTCAAGTGATTGTCCTGCCTCAGCCTCCTGAGTAGCTGG
       [T,C]
       GCTACAGGCGCGTGCCACCATGCCCAGCTAATTTTTGTATTTTTAGTAGAGACAGGGTTT
       TACTATGTTGGCCAGCTGGTTTCTAACTCCTGAACTCGGGTGATCTGCCTGCCTCGGCCT
       CCCAAAGTGCTGGGATTACAGGCATGGGCCTCCGTGCCCGGCCATGTATTTATTTAGGCA
       AGGTCTCTCTCTGTTATCCAGGCTGAAGTGCAGTGGCACATTCATAGCTCACTGCAGCCT
       CAAATTATCCAAGTAACAGGGACTACAGGCATGCACCACCACACCCATCTACTTTTTTTT

21341  TCAGCTCACTGCAACCTCTGCCTCCCTGGCTTAAGCGATCCTCCCACCTCAGCCTCCTGA
       GTACGTGTGACCATAGGCCCATGGCACAAAGCCCAGCTAATTTTTTGTATTTTTAGTAGA
       AATGTGGTTTCACCATGTTGCATAGGCTGGTCTCGAACTTCTGAACTCAAGTGATCTGCC
       TGCCTTGGCCTCCCAAAGTGCTGGGATTCTAGGTATGAGCCACCCTGCTCGGCCTATAAT
       GGCACTTTCCTATCCCATTGATGAGGCTCTACTCTCATGACCTAATCATCTCCCAAAGGC
       [C,G]
       CTAAGGCCTCCTGATACCATCACCTTTGGGGTTAGGTTTTAACATATACATTTTGGGGGG
       ACACAGACATTTTAGACCATAGCACCTCCATTGAAAGGAAACATTTCTGACACCTGGCTA
       TCTCAAAGGGCCCTTTCAGTTCCCCTGCAGGCTGCATTCCCACATCACCAACAAGAGCAG
       CGACACTCACTCAGAGGTTAAATAACTTGTCCAGAGTCACAGCAGTAATGAATGACAGAG
       CTGGGGCTTGAATCCAGGCGTCCTCCTAGAGCCTGGATTCTGTGTAGTGAGTGAAAGCTG

21796  CATTCCCACATCACCAACAAGAGCAGCGACACTCACTCAGAGGTTAAATAACTTGTCCAG
       AGTCACAGCAGTAATGAATGACAGAGCTGGGGCTTGAATCCAGGCGTCCTCCTAGAGCCT
       GGATTCTGTGTAGTGAGTGAAAGCTGACTCCTGGGAGACTTCTGCGTGGTCCTGGTTCTC
       TCTCCAGACTGCACTGCGCAAGTTTCTCTTCCTGATGGTCCCTAGGGTATTACAAAGACA
```

FIGURE 3, page 19 of 22

```
            GTGGCCCTGCCTGTCAGGTGTTTTTATTACCAGATGAGGTCATGGCCTCAGGAACCCTGT
            [A,G]
            GGAAGCTGAGTTCAGAGTCTTTGAGCAGGCTTTAGGGAGGTTCCAGCTTCCCACCACCAA
            GCCCCAGGTGGATTCTTACAGACTCTAGCCTCAGGGTGGGGGGTCTGGAAGATGAGGTTG
            CGGGGTGCGATATTCTGCCCAATTCGCCCCTCCTTGCTCAATCTGTTTCTGCAGGTATTG
            CTGACTACAGACCCAAGGATGGAGAAACCATTGAGCTGAGGCTGGTTAGCTGGTAGCCCC
            TGAGCTCCCTCATCCCAGCAGCCTCGCACACTCCCTAGGCTTCTACCCTCCCTCCTGATG

22159       CCCAGGTGGATTCTTACAGACTCTAGCCTCAGGGTGGGGGGTCTGGAAGATGAGGTTGCG
            GGGTGCGATATTCTGCCCAATTCGCCCCTCCTTGCTCAATCTGTTTCTGCAGGTATTGCT
            GACTACAGACCCAAGGATGGAGAAACCATTGAGCTGAGGCTGGTTAGCTGGTAGCCCCTG
            AGCTCCCTCATCCCAGCAGCCTCGCACACTCCCTAGGCTTCTACCCTCCCTCCTGATGTC
            CCTGGAACAGGAACTCGCCTGACCCTGCTGCCACCTCCTGTGCACTTTGAGCAATGCCCC
            [C,T]
            TGGGATCACCCCAGCCACAAGCCCTTCGAGGGCCCTATACCATGGCCCACCTTGGAGCAG
            AGAGCCAAGCATCTTCCCTGGGAAGTCTTTCTGGCCAAGTCTGGCCAGCCTGGCCCTGCA
            GGTCTCCCATGAAGGCCACCCCATGGTCTGATGGGCATGAAGCATCTCAGACTCCTTGGC
            AAAAAACGGAGTCCGCAGGCCGCAGGTGTTGTGAAGACCACTCGTTCTGTGGTTGGGGTC
            CTGCAAGAAGGCCTCCTCAGCCCGGGGGCTATGGCCCTGACCCCAGCTCTCCACTCTGCT

22334       CCCTGAGCTCCCTCATCCCAGCAGCCTCGCACACTCCCTAGGCTTCTACCCTCCCTCCTG
            ATGTCCCTGGAACAGGAACTCGCCTGACCCTGCTGCCACCTCCTGTGCACTTTGAGCAAT
            GCCCCCTGGGATCACCCCAGCCACAAGCCCTTCGAGGGCCCTATACCATGGCCCACCTTG
            GAGCAGAGAGCCAAGCATCTTCCCTGGGAAGTCTTTCTGGCCAAGTCTGGCCAGCCTGGC
            CCTGCAGGTCTCCCATGAAGGCCACCCCATGGTCTGATGGGCATGAAGCATCTCAGACTC
            [C,A]
            TTGGCAAAAAACGGAGTCCGCAGGCCGCAGGTGTTGTGAAGACCACTCGTTCTGTGGTTG
            GGGTCCTGCAAGAAGGCCTCCTCAGCCCGGGGGCTATGGCCCTGACCCCAGCTCTCCACT
            CTGCTGTTAGAGTGGCAGCTCCGAGCTGGTTGTGGCACAGTAGCTGGGGAGACCTCAGCA
            GGGCTGCTCAGTGCCTGCCTCTGACAAAATTAAAGCATTGATGGCCTGTGGACCTGCTAC
            AGTGGCCTGGTGCCTCATACTCCTCAGGTGCAGGGGCAGGGACAAGAGAAGGGGGAAGTA

22346       TCATCCCAGCAGCCTCGCACACTCCCTAGGCTTCTACCCTCCCTCCTGATGTCCCTGGAA
            CAGGAACTCGCCTGACCCTGCTGCCACCTCCTGTGCACTTTGAGCAATGCCCCCTGGGAT
            CACCCCAGCCACAAGCCCTTCGAGGGCCCTATACCATGGCCCACCTTGGAGCAGAGAGCC
            AAGCATCTTCCCTGGGAAGTCTTTCTGGCCAAGTCTGGCCAGCCTGGCCCTGCAGGTCTC
            CCATGAAGGCCACCCCATGGTCTGATGGGCATGAAGCATCTCAGACTCCTTGGCAAAAAA
            [C,-]
            GGAGTCCGCAGGCCGCAGGTGTTGTGAAGACCACTCGTTCTGTGGTTGGGGTCCTGCAAG
            AAGGCCTCCTCAGCCCGGGGGCTATGGCCCTGACCCCAGCTCTCCACTCTGCTGTTAGAG
            TGGCAGCTCCGAGCTGGTTGTGGCACAGTAGCTGGGGAGACCTCAGCAGGGCTGCTCAGT
            GCCTGCCTCTGACAAAATTAAAGCATTGATGGCCTGTGGACCTGCTACAGTGGCCTGGTG
            CCTCATACTCCTCAGGTGCAGGGGCAGGGACAAGAGAAGGGGGAAGTAACCCCATCAGGG

22476       ACAAGCCCTTCGAGGGCCCTATACCATGGCCCACCTTGGAGCAGAGAGCCAAGCATCTTC
            CCTGGGAAGTCTTTCTGGCCAAGTCTGGCCAGCCTGGCCCTGCAGGTCTCCCATGAAGGC
            CACCCCATGGTCTGATGGGCATGAAGCATCTCAGACTCCTTGGCAAAAAACGGAGTCCGC
            AGGCCGCAGGTGTTGTGAAGACCACTCGTTCTGTGGTTGGGGTCCTGCAAGAAGGCCTCC
            TCAGCCCGGGGGCTATGGCCCTGACCCCAGCTCTCCACTCTGCTGTTAGAGTGGCAGCTC
            [C,T]
            GAGCTGGTTGTGGCACAGTAGCTGGGGAGACCTCAGCAGGGCTGCTCAGTGCCTGCCTCT
            GACAAAATTAAAGCATTGATGGCCTGTGGACCTGCTACAGTGGCCTGGTGCCTCATACTC
            CTCAGGTGCAGGGGCAGGGACAAGAGAAGGGGGAAGTAACCCCATCAGGGAGGAGTGGAG
            GGTGCCTGAGCCGCCATGTGGGCATTGGGGAGTGATGGGAATGCCAGCAGTGATGACGT
            TGACTACTGACTGAGCACCCACTACTATGACTGAGCACTCACTCGCTAGATACTATCTTG

23143       GCCGGGCGTGGTGGCTCACGCCTGTAATCCCAGCACTTTAGGAGGCCAAGGCAGGTGGAT
            CACAAGGTCAGGAGTTTGAGATCAGCCTGGCCAACATGGTGAAACTCCATCTTTACTAAA
            AATACAAAAAATTAGCCAGGCATGGTGTTGCATGCCTGCATGCCTGTAATCCCAGTTACT
            TGGGAAGCTGAGGCAGGAGAATTGCTTGAACCCTGGAGGCGGAGGTTGTAGTGAGCCGAG
            ATCACGCCATTGCACTCCAGCTTGGGCAAGAAGAGAAACACTCTCAAAAAAAAAAAAAAA
            [A,-,T]
            CAGGAAACTGGTGCTCAAAAAGGAAAAGTGACTCACCAAGGTCACAGACTAGGCAGTGAT
            GCTGGGGGAACCTGGCTCAGGGGACACAGACCTGGCCTGGGGCAGCCTTGCAGCTCCTCC
            ACTAAAATACTGAAAATGAGGGGCTTCGATGATGGTTATAATCGTATGGCAGAGCCCCAA
            CTCAACTGGAGCCCTGGGACCCAGAAGCTAGGGTCTCACTCCCTGCTTTTCCACAAGGCA
            CCATTAGGGCATCACCCCAGGCCTCGGCAGCCACGACGCAGGGATCCTGCCTCTCATTGG

23445       AGGAAACTGGTGCTCAAAAAGGAAAAGTGACTCACCAAGGTCACAGACTAGGCAGTGATG
            CTGGGGGAACCTGGCTCAGGGGACACAGACCTGGCCTGGGGCAGCCTTGCAGCTCCTCCA
            CTAAAATACTGAAAATGAGGGGCTTCGATGATGGTTATAATCGTATGGCAGAGCCCCAAC
```

FIGURE 3, page 20 of 22

```
          TCAACTGGAGCCCTGGGACCCAGAAGCTAGGGTCTCACTCCCTGCTTTTCCACAAGGCAC
          CATTAGGGCATCACCCCAGGCCTCGGCAGCCACGACGCAGGGATCCTGCCTCTCATTGGT
          [T,C]
          GGGGGCTTAGGGGCTCTGGGCTGCCCTCTTGAAGAGGGGGTTCAGCCCAGCGAGGCACCC
          CCTATGCTGCACCCCACCAAGGTTAGGAAGAGGTCCTGTCCTCAGTGGGGCCCTCTGATG
          AACAGCCCATCAGGTCTGCGTCCACATGCCTTGGAAGAGATGGTGACATACTCAAAGTCC
          TTGAAGCCGCATATTAAACCACCTAGAGCACCATCTTCAAACATTTAGGGTCTGAGAAGA
          TAGGGGAAGTAAGCAATTTAAAACATTTCTTTATATTGGGCCAGGTGCAATGGCTCACGT

23974   GGTCTGAGAAGATAGGGGAAGTAAGCAATTTAAAACATTTCTTTATATTGGGCCAGGTGC
          AATGGCTCACGTCTGTAATCCCAGCGCTTTGGGAGGACGAGGATCACCTGAGGTCAGGAG
          TTCAAGATCAGCCTGGCGAACATGGAGAAACCCCATCTCTACTAAAAATACAAAAATTAG
          CTCAGGCGTGGTGATGTGCACCTGTAATCCTAGCTATTCAGGAGGCTGAGGCACAAGAAT
          TGCTTGAGTCAATATTGCACCACTGCACTCCAGCCTGGGCAACAGCGAGACTCTTGTCTC
          [A,-]
          AAAAAAAAAAAAGATATTTGCTGAAAAGACCCAGCCTGCCAAAACTCAGGGGCAGCCAAGG
          GAGGTAGTGAAATGGAAGTTGGAGCTCAGCGCTCCCACACCTCCACTGCCCTCAGGCCTT
          CTCTGCCTCTTTCCCATCAGTCAGCTGCTTCTGGGCATGGTCCTGGCAGAGACTTGGCCT
          CCTTCCAGTTCAAGCTCCCTCTTAGATTGTGTCCCACGCCACTGAGTCTTTGGGACACTG
          GGTCAGATGTCTAGTCTGGCACAATTGGCAGGAATCCCAAGAAACAGTGTGAGTGAGGGG

24865   ATAGCTGGGATTACAGGTGTGCACCACCATGCCCAGCCTAATTTTTGTATTATTAGTAGA
          GATGGGGTTTCACCATGTTGTCCAGGCTGGTCATGAACTCCTGACCTCAAGTGATCCACC
          CGCTTTGGCCTCCCAAAGTGCTGGGATTACAAGCATGAGCCACAGTGCCTGGCCTGACCC
          TGCTCTTTTGAAAGACCATTCCCCCAAATTCTGTGCACCTGTGTGCCTTTCTTCTCTCTG
          CCTCCTCTCAGCTCTGCCCCGCTCTCCTCCCTTCTCCTCTGGCAAATCCCACTCATCTCT
          [G,T]
          GAAGCCCTTCTTCCAGGGGAAGCCCTGATCATGCTGCTTTCTCCTGTGGGAGGGATGAAG
          GACGTGGCCCACGGAGTTTGTTTTGTTTTGTTTTGAGATGGAGTTTTGCTCATGTTGCCC
          AGGCTGGGGTACAATGGTACGATCTCAGCTCACTGCAACCTCTACGTCCCGGGTTCAAGC
          GGTTCTCCTGCCTTAGCCTCCCCAGTAGCTGGGATTACTGGCATGAACCACCACACCTGG
          CTAATTTTGTGTTTTTAGTAGAGATGGGGTTTCTTCATGTTGGTCAGGCTGGTCTCGAAC

25040   GACCCTGCTCTTTTGAAAGACCATTCCCCCAAATTCTGTGCACCTGTGTGCCTTTCTTCT
          CTCTGCCTCCTCTCAGCTCTGCCCCGCTCTCCTCCCTTCTCCTCTGGCAAATCCCACTCA
          TCTCTTGAAGCCCTTCTTCCAGGGGAAGCCCTGATCATGCTGCTTTCTCCTGTGGGAGGG
          ATGAAGGACGTGGCCCACGGAGTTTGTTTTGTTTTGTTTTGAGATGGAGTTTTGCTCATG
          TTGCCCAGGCTGGGGTACAATGGTACGATCTCAGCTCACTGCAACCTCTACGTCCCGGGT
          [T,C]
          CAAGCGGTTCTCCTGCCTTAGCCTCCCCAGTAGCTGGGATTACTGGCATGAACCACCACA
          CCTGGCTAATTTTGTGTTTTTAGTAGAGATGGGGTTTCTTCATGTTGGTCAGGCTGGTCT
          CGAACTCCCAACCTCAGGTGATCTGCCTGCCTCGGCCTCCCAAAGTACTGGGATTACAGG
          GTTGAGCCACTGTGCCTGGCCCAGGCCCACGGAGTTTTAAGAGGCTTCCTGTGGCAGTGG
          CATCCAGACGGAGTGCAGAAACTCAAAGTTGAAGGCCAGAAGCTCAGGGAAGGGGGAGTG

25046   GCTCTTTTGAAAGACCATTCCCCCAAATTCTGTGCACCTGTGTGCCTTTCTTCTCTCTGC
          CTCCTCTCAGCTCTGCCCCGCTCTCCTCCCTTCTCCTCTGGCAAATCCCACTCATCTCTT
          GAAGCCCTTCTTCCAGGGGAAGCCCTGATCATGCTGCTTTCTCCTGTGGGAGGGATGAAG
          GACGTGGCCCACGGAGTTTGTTTTGTTTTGTTTTGAGATGGAGTTTTGCTCATGTTGCCC
          AGGCTGGGGTACAATGGTACGATCTCAGCTCACTGCAACCTCTACGTCCCGGGTTCAAGC
          [G,A]
          GTTCTCCTGCCTTAGCCTCCCCAGTAGCTGGGATTACTGGCATGAACCACCACACCTGGC
          TAATTTTGTGTTTTTAGTAGAGATGGGGTTTCTTCATGTTGGTCAGGCTGGTCTCGAACT
          CCCAACCTCAGGTGATCTGCCTGCCTCGGCCTCCCAAAGTACTGGGATTACAGGGTTGAG
          CCACTGTGCCTGGCCCAGGCCCACGGAGTTTTAAGAGGCTTCCTGTGGCAGTGGCATCCA
          GACGGAGTGCAGAAACTCAAAGTTGAAGGCCAGAAGCTCAGGGAAGGGGGAGTGTGAGTT

25193   ATCATGCTGCTTTCTCCTGTGGGAGGGATGAAGGACGTGGCCCACGGAGTTTGTTTTGTT
          TTGTTTTGAGATGGAGTTTTGCTCATGTTGCCCAGGCTGGGGTACAATGGTACGATCTCA
          GCTCACTGCAACCTCTACGTCCCGGGTTCAAGCGGTTCTCCTGCCTTAGCCTCCCCAGTA
          GCTGGGATTACTGGCATGAACCACCACACCTGGCTAATTTTGTGTTTTTAGTAGAGATGG
          GGTTTCTTCATGTTGGTCAGGCTGGTCTCGAACTCCCAACCTCAGGTGATCTGCCTGCCT
          [C,T]
          GGCCTCCCAAAGTACTGGGATTACAGGGTTGAGCCACTGTGCCTGGCCCAGGCCCACGGA
          GTTTTAAGAGGCTTCCTGTGGCAGTGGCATCCAGACGGAGTGCAGAAACTCAAAGTTGAA
          GGCCAGAAGCTCAGGGAAGGGGGAGTGTGAGTTGAGGAGTCTCTTGGCTGCCAGGGCCAG
          AAACCGAACTCCAAGCCTCTCCACAACAGCGGGTGTAGAGCATGTAGAATCAGAGAGGAG
          GCTGAGCCATGCAGCCCCGAGAAGAGGGGAATGCCACTGAGCCACAGAGACCCAGTGCCA

25529   AGTGCAGAAACTCAAAGTTGAAGGCCAGAAGCTCAGGGAAGGGGGAGTGTGAGTTGAGGA
          GTCTCTTGGCTGCCAGGGCCAGAAACCGAACTCCAAGCCTCTCCACAACAGCGGGTGTAG
```

FIGURE 3, page 21 of 22

```
        AGCATGTAGAATCAGAGAGGAGGCTGAGCCATGCAGCCCCGAGAAGAGGGGAATGCCACT
        GAGCCACAGAGACCCAGTGCCACTGCCAGGTGTCTCTGCCTCCACTTCCCATGACCC
        [T,G]
        GCCTGTCTCTGTATGCAGGCTTCACCCTCTCTCGTTGTACATTGTACACATTCTAGGTGA
        CACCAGCAGCTTCTGATTCTCATCTCCCATAACATCAGCCCCCCAGAGAGGGGACAACTG
        CTGAGCTGATAACATAATAGATGCCCCTTTCCTGGAGGCCATGGTCATGGTCAGCGTGGA
        GAGGATGAAGCCTGAGCAGGCAGGATCGGGGGTCTAGAGGGGAAGGAGGTGGAAGTT

25614   GGCCAGAAGCTCAGGGAAGGGGGAGTGTGAGTTGAGGAGTCTCTTGGCTGCCAGGGCCAG
        AAACCGAACTCCAAGCCTCTCCACAACAGCGGGTGTAGAGCATGTAGAATCAGAGAGGAG
        GCTGAGCCATGCAGCCCCGAGAAGAGGGGAATGCCACTGAGCCACAGAGACCCAGTGCCA
        CTGCCAGGTGTCTCTGCCTCCACTTCCCATGACCCGGCCTGTCTCTGTATGCAGGCTTCA
        CCCTCTCTCGTTGTACATTGTACACATTCTAGGTGACACCAGCAGCTTCTGATTCTCATC
        [C,T]
        CCCATAACATCAGCCCCCCAGAGAGGGGACAACTGCTGAGCTGATAACATAATAGATGCC
        CCTTTCCTGGAGGCCATGGTCATGGTCAGCGTGGAGAGGATGAAGCCTGAGCAGGCAGGA
        TCGGGGGTCTAGAGGGGAAGGAGGTGGAAGTTGAGATCACAGACCTGTGGTCAGGTGGCC
        TGGGAAGGGTTTGACGAGTGTCGGCCCAAAGAGCTTGGAAGGGATTTTGCTGCTGTGGGT
        GAGCACTGCCTCTCCCCTTAGGGACAACAGCCACCTCTTCTCTCCCCATTTGCCTTTCCC

25785   CCAGTGCCACTGCCAGGTGTCTCTGCCTCCACTTCCCATGACCCGGCCTGTCTCTGTATG
        CAGGCTTCACCCTCTCTCGTTGTACATTGTACACATTCTAGGTGACACCAGCAGCTTCTG
        ATTCTCATCTCCCATAACATCAGCCCCCCAGAGAGGGGACAACTGCTGAGCTGATAACAT
        AATAGATGCCCCTTTCCTGGAGGCCATGGTCATGGTCAGCGTGGAGAGGATGAAGCCTGA
        GCAGGCAGGATCGGGGGTCTAGAGGGGAAGGAGGTGGAAGTTGAGATCACAGACCTGTGG
        [C,T]
        CAGGTGGCCTGGGAAGGGTTTGACGAGTGTCGGCCCAAAGAGCTTGGAAGGGATTTTGCT
        GCTGTGGGTGAGCACTGCCTCTCCCCTTAGGGACAACAGCCACCTCTTCTCTCCCCATTT
        GCCTTTCCCTTCTGTAGATATGAAACACAGGCCTCCTTGTCAGGCCCCTACTTAACCTCC
        GTGATGGGAAAGCGGCCGGAGAAAGGGAGTTCTGGCAGCTTCTCCGAGACCCCAACACC
        CCACTGTTGCAAGGTGAGTCATGGCCTGACACTCTGGATGTGTCCCCTACCCCAAGCTTA

26266   GTGATGGGGAAAGCGGCCGGAGAAAGGGAGTTCTGGCAGCTTCTCCGAGACCCCAACACC
        CCACTGTTGCAAGGTGAGTCATGGCCTGACACTCTGGATGTGTCCCCTACCCCAAGCTTA
        CTCAGCCAAGAGGCTTCATCAACTCACCCCAGCTTTCCCTAGCACCTCCTGGGCCACAC
        CTTCACAAAATCACTGATGCTCAAAGTTGGATATAATATATTGAACTGAAGCCTTAGCAT
        TTTTATGCAAGTTACTGTGGAAATTCTAGGAAACCAGACAGATTACAAAAAAAAAAAAAA
        [A,-]
        CTAGAAGAAAATTAACATCACCTAGGATATACTACCTAGGAATAACGTCTTTTATTTTGA
        GATGGAGTTTCGCTCTTGTTGCCCAGGCTGGAGTGCAGCGGTATGATCTCGGCTCGCTGC
        AACCTCCGCCTCCTGGGTTCATGTGATTCTTCCACCTCGGCCTTCCTAGAGCCCAAGTGG
        TCTGCCTGCCTCTGCCTCCCAAAGTTCTGGGATTACAGGCATGAGCCACCGCACCCAGCC
        AAAATTACTTAACTTTTCTTCTAGATACTTTTTAAAAATATGGCAGTAAGTTTTTCATAA
```

FIGURE 3, page 22 of 22

ISOLATED HUMAN SECRETED PROTEINS, NUCLEIC ACID MOLECULES ENCODING HUMAN SECRETED PROTEINS, AND USES THEREOF

FIELD OF THE INVENTION

The present invention is in the field of secreted proteins that are related to the transcobalamin II secreted subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Secreted Proteins

Many human proteins serve as pharmaceutically active compounds. Several classes of human proteins that serve as such active compounds include hormones, cytokines, cell growth factors, and cell differentiation factors. Most proteins that can be used as a pharmaceutically active compound fall within the family of secreted proteins. It is, therefore, important in developing new pharmaceutical compounds to identify secreted proteins that can be tested for activity in a variety of animal models. The present invention advances the state of the art by providing many novel human secreted proteins.

Secreted proteins are generally produced within cells at rough endoplasmic reticulum, are then exported to the golgi complex, and then move to secretory vesicles or granules, where they are secreted to the exterior of the cell via exocytosis.

Secreted proteins are particularly useful as diagnostic markers. Many secreted proteins are found, and can easily be measured, in serum. For example, a 'signal sequence trap' technique can often be utilized because many secreted proteins, such as certain secretory breast cancer proteins, contain a molecular signal sequence for cellular export. Additionally, antibodies against particular secreted serum proteins can serve as potential diagnostic agents, such as for diagnosing cancer.

Secreted proteins play a critical role in a wide array of important biological processes in humans and have numerous utilities; several illustrative examples are discussed herein. For example, fibroblast secreted proteins participate in extracellular matrix formation. Extracellular matrix affects growth factor action, cell adhesion, and cell growth. Structural and quantitative characteristics of fibroblast secreted proteins are modified during the course of cellular aging and such aging related modifications may lead to increased inhibition of cell adhesion, inhibited cell stimulation by growth factors, and inhibited cell proliferative ability (Eleftheriou et al., *Mutat Res* 1991 March-November; 256 (2–6): 127–38).

The secreted form of amyloid beta/A4 protein precursor (APP) functions as a growth and/or differentiation factor. The secreted form of APP can stimulate neurite extension of cultured neuroblastoma cells, presumably through binding to a cell surface receptor and thereby triggering intracellular transduction mechanisms. (Roch et al., *Ann N Y Acad Sci* Sep. 24, 1993;695:149–57). Secreted APPs modulate neuronal excitability, counteract effects of glutamate on growth cone behaviors, and increase synaptic complexity. The prominent effects of secreted APPs on synaptogenesis and neuronal survival suggest that secreted APPs play a major role in the process of natural cell death and, furthermore, may play a role in the development of a wide variety of neurological disorders, such as stroke, epilepsy, and Alzheimer's disease (Mattson et al., *Perspect Dev Neurobiol* 1998; 5(4):337–52).

Breast cancer cells secrete a 52K estrogen-regulated protein (see Rochefort et al., *Ann N Y Acad Sci* 1986;464:190–201). This secreted protein is therefore useful in breast cancer diagnosis.

Two secreted proteins released by platelets, platelet factor 4 (PF4) and beta-thromboglobulin (betaTG), are accurate indicators of platelet involvement in hemostasis and thrombosis and assays that measure these secreted proteins are useful for studying the pathogenesis and course of thromboembolic disorders (Kaplan, *Adv Exp Med Biol* 1978;102:105–19).

Vascular endothelial growth factor (VEGF) is another example of a naturally secreted protein. VEGF binds to cell-surface heparan sulfates, is generated by hypoxic endothelial cells, reduces apoptosis, and binds to high-affinity receptors that are up-regulated by hypoxia (Asahara et al., *Semin Interv Cardiol* 1996 September;1(3):225–32).

Many critical components of the immune system are secreted proteins, such as antibodies, and many important functions of the immune system are dependent upon the action of secreted proteins. For example, Saxon et al., *Biochem Soc Trans* 1997 May;25(2):383–7, discusses secreted IgE proteins.

For a further review of secreted proteins, see Nilsen-Hamilton et al., *Cell Biol Int Rep* 1982 September;6(9): 815–36.

Transcobalamin II

Many biochemical reactions require the involvement of cobalamin ("Cbl"), also known as vitamin B12, as coenzyme factors. Human Cbl-dependent metabolism includes the biosynthesis of methionine from homocysteine and the isomerization of methylmalonyl-CoA to succinyl-CoA. Although cobalamin is highly water-soluble, it is nevertheless impervious to plasma membrane. Cobalamin is delivered into the designated subcellular locations through multiple physiological steps.

The cellular uptake of cobalamin is mediated by transcobalamin II (TCII), a plasma protein that binds Cbl and is secreted by human umbilical vein endothelial (HUVE) cells. These cells synthesize and secrete TC II and, therefore, served as the source of the library from which the TC II cDNA was isolated. This full-length cDNA consists of 1866 nucleotides that code for a leader peptide of 18 amino acids, a secreted protein of 409 amino acids, a 5'-untranslated segment of 37 nucleotides, and a 3'-untranslated region of 548 nucleotides. A single 1.9-kilobase species of mRNA corresponding to the size of the cDNA was identified by Northern blot analysis of the RNA isolated from HUVE cells. TCII has 20% amino acid homology and greater than 50% nucleotide homology with human transcobalamin I (TCI) and with rat intrinsic factor (R-IF). TCII has no homology with the amino-terminal region of R-IF that has been reported to have significant primary as well as secondary structural homology with the nucleotide-binding domain of NAD-dependent oxidoreductases. The regions of homology that are common to all three proteins are located in seven domains of the amino acid sequence. One or more of these conserved domains is likely to be involved in Cbl binding, a function that is common to all three proteins.

However, the difference in the affinity of TCII, TCI, and R-IF for Cbl and Cbl analogues indicates, a priori, that structural differences in the ligand-binding site of these proteins exist and these probably resulted from divergence of a common ancestral gene. (Platica, et al., J Biol Chem Apr 25;266(12):7860–3 (1991))

Extracellularly secreted cobalamin is continually transported across cellular space through transcytosis within the endomembrane-secretory system, within which transcobalamin II ("TC II") binds to proteolytically-released Cbl. TC II-Cbl-containing vesicles release their contents into the circulation system. The uptake of TC II-Cbl from the circulating fluids utilizes similar pathways, including receptor-mediated translocation, vesicle-dependent trafficking and targeting, and lysosome-based proteolytical release.

TC II is a non-glycosylated secretory protein of molecular mass 43 kDa in plasma while its homologs IF and haptocorrin are heavily glycosylated. A conserved Cbl-binding domain (ProSite pattern: PS000468) exists among the three types of the proteins (Seetharam and Li, Vitam. Horm. 59:337–366 (2000); Seetharam B, et al., Annu. Rev. Nutr. 19:173–195 (1999); Hofman, et al., Nuc. Acid Res. 27: 215–219 (1999)). The affinity toward Cbl is suggested to be the highest for haptocorrin (Fedosov, et al., Biochim. Biophys. Acta 1292:113–119 (1996)). Of two TCs, TC I has been identified as a major protein constituent of secondary granules in neotrophil and mapped onto chromosome 11q11-q12 (Johnston, et al., J. Biol. Chem. 264:15754–15757 (1989)). IF (Chr 11), TC I and TC II (Chr 22q) are proposed to be diverged from a common ancestral gene as they are conserved in the multiple regions, but with different affinity toward Cbl (Platica, et al., J Biol Chem Apr 25;266(12): 7860–3 (1991)).

Disorders of transport proteins such as TC II can lead to abnormal function of methylmalonyl-CoA mutase and methionine synthase (Fowler, Eur. J. Pediatr. 157(suppl. 2):S60-S66 (1998)). Clinical evidence has demonstrated that autosomal recessive mutations of TC II gene can lead to a disorder whose observed symptoms include megaloblastic anemia, impaired immune response and neurological manifestations. Li, et al., Hum. Mol. Genet. 3:1835–1840 (1994). Single nucleotide deletions in patients were reported to cause TC II deficiency disease. (Li, et al., Biochem. Biophys. Res. Commun. 204:1111–1118 (1994)).

Cancer cells are commonly characterized by a disturbed balance of methionine metabolism, resulting in ceased proliferation of methionine-dependent cells and overproduction of methionine-independent cells. The imbalance between methionine comsumption and formation is related to methionine synthase and methylcobalamin cofactor. The lack of cellular methylcobalamin, resulted from various defects in cobalamin metabolism as depicted above, causes a low rate of homocysteine remethylation, and thus methionine production (Fiskerstrand, et al., J. Biol. Chem. 273: 20180–20184 (1998)).

Secreted proteins, particularly members of the transcobalamin II secreted protein subfamily, are a major target for drug action and development. Accordingly, it is valuable to the field of pharmaceutical development to identify and characterize previously unknown members of this subfamily of secreted proteins. The present invention advances the state of the art by providing previously unidentified human secreted proteins that have homology to members of the transcobalamin II secreted protein subfamily.

SUMMARY OF THE INVENTION

The present invention is based in part on the identification of amino acid sequences of human secreted peptides and proteins that are related to the transcobalamin II secreted protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate secreted protein activity in cells and tissues that express the secreted protein. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus.

DESCRIPTION OF THE FIGURE SHEETS

FIG. 1 provides the nucleotide sequence of a cDNA molecule or transcript sequence that encodes the secreted protein of the present invention. (SEQ ID NOS: 1–2) In addition, structure and functional information is provided, such as ATG start, stop and tissue distribution, where available, that allows one to readily determine specific uses of inventions based on this molecular sequence. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus.

FIG. 2 provides the predicted amino acid sequence of the secreted protein of the present invention. (SEQ ID NOS:3–4) In addition structure and functional information such as protein family, function, and modification sites is provided where available, allowing one to readily determine specific uses of inventions based on this molecular sequence.

FIG. 3 provides genomic sequences that span the gene encoding the secreted protein of the present invention. (SEQ ID NO:5) In addition structure and functional information, such as intron/exon structure, promoter location, etc., is provided where available, allowing one to readily determine specific uses of inventions based on this molecular sequence. As illustrated in FIG. 3, SNPs were identified for isoform 1 at 36 different nucleotide positions and for isoform 2 at 34 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a secreted protein or part of a secreted protein and are related to the transcobalamin II secreted protein subfamily. Utilizing these sequences, additional genomic sequences were assembled and transcript and/or cDNA sequences were isolated and characterized. Based on this analysis, the present invention provides amino acid sequences of human secreted peptides and proteins that are related to the transcobalamin II secreted protein subfamily, nucleic acid sequences in the form of transcript sequences, cDNA sequences and/or genomic sequences that encode these secreted peptides and proteins, nucleic acid variation (allelic information), tissue distribution of expression, and information about the closest art known protein/peptide/domain that has structural or sequence homology to the secreted protein of the present invention.

In addition to being previously unknown, the peptides that are provided in the present invention are selected based on their ability to be used for the development of commercially important products and services. Specifically, the present peptides are selected based on homology and/or structural relatedness to known secreted proteins of the transcobalamin II secreted protein subfamily and the expression pattern observed. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known transcobalamin II family or subfamily of secreted proteins.

Specific Embodiments

Peptide Molecules

The present invention provides nucleic acid sequences that encode protein molecules that have been identified as being members of the secreted protein family of proteins and are related to the transcobalamin II secreted protein subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the secreted peptides of the present invention, secreted peptides, or peptides/proteins of the present invention.

The present invention provides isolated peptide and protein molecules that consist of, consist essentially of, or comprise the amino acid sequences of the secreted peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the secreted peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated secreted peptide can be purified from cells that naturally express it, purified from cells that have been altered to express it (recombinant), or synthesized using known protein synthesis methods. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. For example, a nucleic acid molecule encoding the secreted peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NOS:3–4), for example, proteins encoded by the transcript/cDNA nucleic acid sequences shown in FIG. 1 (SEQ ID NOS:1–2) and the genomic sequences provided in FIG. 3 (SEQ ID NO:5). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NOS:3–4), for example, proteins encoded by the transcript/cDNA nucleic acid sequences shown in FIG. 1 (SEQ ID NOS:1–2) and the genomic sequences provided in FIG. 3 (SEQ ID NO:5). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NOS:3–4), for example, proteins encoded by the transcript/cDNA nucleic acid sequences shown in FIG. 1 (SEQ ID NOS:1–2) and the genomic sequences provided in FIG. 3 (SEQ ID NO:5). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the secreted peptides of the present invention are the naturally occurring mature proteins. A brief description of how various types of these proteins can be made/isolated is provided below.

The secreted peptides of the present invention can be attached to heterologous sequences to form chimeric or fusion proteins. Such chimeric and fusion proteins comprise a secreted peptide operatively linked to a heterologous protein having an amino acid sequence not substantially homologous to the secreted peptide. "Operatively linked" indicates that the secreted peptide and the heterologous protein are fused in-frame. The heterologous protein can be fused to the N-terminus or C-terminus of the secreted peptide.

In some uses, the fusion protein does not affect the activity of the secreted peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant secreted peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A secreted peptide-encoding nucleic acid can be cloned into such an expression vector such that the fusion moiety is linked in-frame to the secreted peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the secreted peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the secreted peptides of the present invention as well as being encoded by the same genetic locus as the secreted peptide provided herein.

Allelic variants of a secreted peptide can readily be identified as being a human protein having a high degree (significant) of sequence homology/identity to at least a portion of the secreted peptide as well as being encoded by the same genetic locus as the secreted peptide provided herein. Genetic locus can readily be determined based on the genomic information provided in FIG. 3, such as the genomic sequence mapped to the reference human. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a secreted peptide encoding nucleic acid molecule under stringent conditions as more fully described below.

FIG. 3 provides information on SNPs that have been found in the gene encoding the enzyme of the present invention. SNPs were identified for isoform 1 at 36 different nucleotide positions, and for isoform 2 at 34 different nucleotide positions. Changes in the amino acid sequence caused by these SNPs is indicated in FIG. 3 and can readily be determined using the universal genetic code and the protein sequence provided in FIG. 2 as a reference. Some of these SNPs that are located outside the ORF and in introns may affect gene expression. Positioning of each SNP in an exon, intron, or outside the ORF can readily be determined using the DNA position given for each SNP and the start/stop, exon, and intron genomic coordinates given in FIG. 3.

Paralogs of a secreted peptide can readily be identified as having some degree of significant sequence homology/identity to at least a portion of the secreted peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a secreted peptide encoding nucleic acid molecule under moderate to stringent conditions as more fully described below.

Orthologs of a secreted peptide can readily be identified as having some degree of significant sequence homology/identity to at least a portion of the secreted peptide as well as being encoded by a gene from another organism. Preferred orthologs will be isolated from mammals, preferably primates, for the development of human therapeutic targets and agents. Such orthologs will be encoded by a nucleic acid sequence that will hybridize to a secreted peptide encoding nucleic acid molecule under moderate to stringent conditions, as more fully described below, depending on the degree of relatedness of the two organisms yielding the proteins.

Non-naturally occurring variants of the secreted peptides of the present invention can readily be generated using recombinant techniques. Such variants include, but are not limited to deletions, additions and substitutions in the amino acid sequence of the secreted peptide. For example, one class of substitutions are conserved amino acid substitution. Such substitutions are those that substitute a given amino acid in a secreted peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant secreted peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as secreted protein activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the secreted peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a secreted peptide. Such fragments can be chosen based on the ability to retain one or more of the biological activities of the secreted peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the secreted peptide, e.g., active site or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in secreted peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N. Y Acad. Sci.* 663:48–62 (1992)).

Accordingly, the secreted peptides of the present invention also encompass derivatives or analogs in which a substituted amino acid residue is not one encoded by the genetic code, in which a substituent group is included, in which the mature secreted peptide is fused with another compound, such as a compound to increase the half-life of the secreted peptide (for example, polyethylene glycol), or in which the additional amino acids are fused to the mature secreted peptide, such as a leader or secretory sequence or a sequence for purification of the mature secreted peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a secreted protein-effector protein interaction or secreted protein-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, secreted proteins isolated from humans and their human/mammalian orthologs serve as targets for identifying agents for use in mammalian therapeutic applications, e.g. a human drug, particularly in modulating a biological or pathological response in a cell or tissue that expresses the secreted protein. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus. A large percentage of pharmaceutical agents are being developed that modulate the activity of secreted proteins, particularly members of the transcobalamin II subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. Such uses can readily be determined using the information provided herein, that which is known in the art, and routine experimentation.

The proteins of the present invention (including variants and fragments that may have been disclosed prior to the present invention) are useful for biological assays related to secreted proteins that are related to members of the transcobalamin II subfamily. Such assays involve any of the known secreted protein functions or activities or properties useful for diagnosis and treatment of secreted protein-related conditions that are specific for the subfamily of secreted proteins that the one of the present invention belongs to, particularly in cells and tissues that express the secreted protein. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus.

The proteins of the present invention are also useful in drug screening assays, in cell-based or cell-free systems. Cell-based systems can be native, i.e., cells that normally express the secreted protein, as a biopsy or expanded in cell culture. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. In an alternate embodiment, cell-based assays involve recombinant host cells expressing the secreted protein.

The polypeptides can be used to identify compounds that modulate secreted protein activity of the protein in its natural state or an altered form that causes a specific disease or pathology associated with the secreted protein. Both the secreted proteins of the present invention and appropriate variants and fragments can be used in high-throughput screens to assay candidate compounds for the ability to bind to the secreted protein. These compounds can be further screened against a functional secreted protein to determine the effect of the compound on the secreted protein activity. Further, these compounds can be tested in animal or invertebrate systems to determine activity/effectiveness. Compounds can be identified that activate (agonist) or inactivate (antagonist) the secreted protein to a desired degree.

Further, the proteins of the present invention can be used to screen a compound for the ability to stimulate or inhibit interaction between the secreted protein and a molecule that normally interacts with the secreted protein, e.g. a substrate or a component of the signal pathway that the secreted protein normally interacts (for example, another secreted protein). Such assays typically include the steps of combining the secreted protein with a candidate compound under conditions that allow the secreted protein, or fragment, to interact with the target molecule, and to detect the formation of a complex between the protein and the target or to detect the biochemical consequence of the interaction with the secreted protein and the target.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant secreted proteins or appropriate fragments containing mutations that affect secreted protein function and thus compete for substrate. Accordingly, a fragment that competes for substrate, for example with a higher affinity, or a fragment that binds substrate but does not allow release, is encompassed by the invention.

Any of the biological or biochemical functions mediated by the secreted protein can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the secreted protein can be assayed. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus.

Binding and/or activating compounds can also be screened by using chimeric secreted proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native secreted protein. Accordingly, a different set of signal transduction components is available as an end-point assay for activation. This allows for assays to be performed in other than the specific host cell from which the secreted protein is derived.

The proteins of the present invention are also useful in competition binding assays in methods designed to discover compounds that interact with the secreted protein (e.g. binding partners and/or ligands). Thus, a compound is exposed to a secreted protein polypeptide under conditions that allow the compound to bind or to otherwise interact with the polypeptide. Soluble secreted protein polypeptide is also added to the mixture. If the test compound interacts with the soluble secreted protein polypeptide, it decreases the amount of complex formed or activity from the secreted protein target. This type of assay is particularly useful in cases in which compounds are sought that interact with specific regions of the secreted protein. Thus, the soluble polypeptide that competes with the target secreted protein region is designed to contain peptide sequences corresponding to the region of interest.

To perform cell free drug screening assays, it is sometimes desirable to immobilize either the secreted protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of secreted protein-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a secreted protein-binding protein and a candidate compound are incubated in the secreted protein-presenting wells and the amount of complex trapped in the well can be quantitated. Methods for detecting such complexes, in addition to those described above for the GST-immobilized complexes, include immunodetection of complexes using antibodies reactive with the secreted protein target molecule, or which are reactive with secreted protein and compete with the target molecule, as well as enzyme-linked assays which rely on detecting an enzymatic activity associated with the target molecule.

Agents that modulate one of the secreted proteins of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of secreted protein activity identified according to these drug screening assays can be used to treat a subject with a disorder mediated by the secreted protein pathway, by treating cells or tissues that express the secreted protein. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. These methods of treatment include the steps of administering a modulator of secreted protein activity in a pharmaceutical composition to a subject in need of such treatment, the modulator being identified as described herein.

In yet another aspect of the invention, the secreted proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the secreted protein and are involved in secreted protein activity.

The two-hybrid system is based on the modular nature of most transcription factors, which consist of separable DNA-binding and activation domains. Briefly, the assay utilizes two different DNA constructs. In one construct, the gene that codes for a secreted protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a secreted protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the secreted protein.

This invention further pertains to novel agents identified by the above-described screening assays. Accordingly, it is within the scope of this invention to further use an agent identified as described herein in an appropriate animal model. For example, an agent identified as described herein (e.g., a secreted protein-modulating agent, an antisense secreted protein nucleic acid molecule, a secreted protein-specific antibody, or a secreted protein-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The secreted proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. The method involves contacting a biological sample with a compound capable of interacting with the secreted protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered secreted protein activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the secreted protein in which one or more of the secreted protein functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and secreted protein activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. Accordingly, methods for treatment include the use of the secreted protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the secreted proteins. Antibodies can be prepared from any region of the peptide as described herein. However, preferred regions will include those involved in function/activity and/or secreted protein/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. Thus, where a specific protein has been correlated with expression in a specific tissue, antibodies that are specific for this protein can be used to identify a tissue type.

The antibodies are also useful for inhibiting protein function, for example, blocking the binding of the secreted peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a secreted peptide or protein of the present invention (cDNA, transcript and genomic sequence). Such nucleic acid molecules will consist of, consist essentially of, or comprise a nucleotide sequence that encodes one of the secreted peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NOS:1–2, transcript sequence and SEQ ID NO:5, genomic sequence), or any nucleic acid molecule that encodes the protein provided in FIG. 2, SEQ ID NOS:3–4. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NOS:1–2, transcript sequence and SEQ ID NO:5, genomic sequence), or any nucleic acid molecule that encodes the protein provided in FIG. 2, SEQ ID NOS:3–4. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NOS:1–2, transcript sequence and SEQ ID NO:5, genomic sequence), or any nucleic acid molecule that encodes the protein provided in FIG. 2, SEQ ID NOS:3–4. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the secreted peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the secreted proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

FIG. 3 provides information on SNPs that have been found in the gene encoding the enzyme of the present invention. SNPs were identified for isoform 1 at 36 different nucleotide positions, and for isoform 2 at 34 different nucleotide positions. Changes in the amino acid sequence caused by these SNPs is indicated in FIG. 3 and can readily be determined using the universal genetic code and the protein sequence provided in FIG. 2 as a reference. Some of these SNPs that are located outside the ORF and in introns may affect gene expression. Positioning of each SNP in an exon, intron, or outside the ORF can readily be determined using the DNA position given for each SNP and the start/stop, exon, and intron genomic coordinates given in FIG. 3.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified for isoform 1 at 36 different nucleotide positions and for isoform 2 at 34 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in secreted protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a secreted protein, such as by measuring a level of a secreted protein-encoding nucleic acid in a sample of cells from a subject e.g., mRNA or genomic DNA, or determining if a secreted protein gene has been mutated. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus.

Nucleic acid expression assays are useful for drug screening to identify compounds that modulate secreted protein nucleic acid expression.

The invention thus provides a method for identifying a compound that can be used to treat a disorder associated with nucleic acid expression of the secreted protein gene, particularly biological and pathological processes that are mediated by the secreted protein in cells and tissues that express it. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus. The method typically includes assaying the ability of the compound to modulate the expression of the secreted protein nucleic acid and thus identifying a compound that can be used to treat a disorder characterized by undesired secreted protein nucleic acid expression. The assays can be performed in cell-based and cell-free systems. Cell-based assays include cells naturally expressing the secreted protein nucleic acid or recombinant cells genetically engineered to express specific nucleic acid sequences.

Thus, modulators of secreted protein gene expression can be identified in a method wherein a cell is contacted with a candidate compound and the expression of mRNA determined. The level of expression of secreted protein mRNA in the presence of the candidate compound is compared to the level of expression of secreted protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate secreted protein nucleic acid expression in cells and tissues that express the secreted protein. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus. Modulation includes both up-regulation (i.e. activation or agonization) or down-regulation (suppression or antagonization) or nucleic acid expression.

Alternatively, a modulator for secreted protein nucleic acid expression can be a small molecule or drug identified using the screening assays described herein as long as the drug or small molecule inhibits the secreted protein nucleic acid expression in the cells and tissues that express the protein. Experimental data as provided in FIG. 1 indicates expression of isoform 1 in adult adrenal gland, mammary gland, retinoblastoma, adenocarcinoma cell line, embryonal carcinoma cell line, adult uterus, adult head-neck, and leukocytes. Experimental data as provided in FIG. 1 indicates expression of isoform 2 in adult adrenal gland, adult uterus, adult head-neck, adult lung tumor, mammary gland, retinoblastoma, adenocarcinoma, and the hippocampus.

The nucleic acid molecules are also useful for monitoring the effectiveness of modulating compounds on the expression or activity of the secreted protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in secreted protein nucleic acid expression, and particularly in qualitative changes that lead to pathology. The nucleic acid molecules can be used to detect mutations in secreted protein genes and gene expression products such as mRNA. The nucleic acid molecules can be used as hybridization probes to detect naturally occurring genetic mutations in the secreted protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the secreted protein gene associated with a dysfunction provides a diagnostic tool for an active disease or susceptibility to disease when the disease results from overexpression, underexpression, or altered expression of a secreted protein.

Individuals carrying mutations in the secreted protein gene can be detected at the nucleic acid level by a variety of techniques. FIG. 3 provides information on SNPs that have been found in the gene encoding the enzyme of the present invention. SNPs were identified for isoform 1 at 36 different nucleotide positions, and for isoform 2 at 34 different nucleotide positions. Changes in the amino acid sequence caused by these SNPs is indicated in FIG. 3 and can readily be determined using the universal genetic code and the protein sequence provided in FIG. 2 as a reference. Some of these SNPs that are located outside the ORF and in introns may affect gene expression. Positioning of each SNP in an exon, intron, or outside the ORF can readily be determined using the DNA position given for each SNP and the start/stop, exon, and intron genomic coordinates given in FIG. 3. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a secreted protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant secreted protein gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS*

86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the secreted protein gene in an individual in order to select an appropriate compound or dosage regimen for treatment. FIG. 3 provides information on SNPs that have been found in the gene encoding the enzyme of the present invention. SNPs were identified for isoform 1 at 36 different nucleotide positions, and for isoform 2 at 34 different nucleotide positions. Changes in the amino acid sequence caused by these SNPs is indicated in FIG. 3 and can readily be determined using the universal genetic code and the protein sequence provided in FIG. 2 as a reference. Some of these SNPs that are located outside the ORF and in introns may affect gene expression. Positioning of each SNP in an exon, intron, or outside the ORF can readily be determined using the DNA position given for each SNP and the start/stop, exon, and intron genomic coordinates given in FIG. 3.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control secreted protein gene expression in cells, tissues, and organisms. A DNA antisense nucleic acid molecule is designed to be complementary to a region of the gene involved in transcription, preventing transcription and hence production of secreted protein. An antisense RNA or DNA nucleic acid molecule would hybridize to the mRNA and thus block translation of mRNA into secreted protein.

Alternatively, a class of antisense molecules can be used to inactivate mRNA in order to decrease expression of secreted protein nucleic acid. Accordingly, these molecules can treat a disorder characterized by abnormal or undesired secreted protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the secreted protein, such as substrate binding.

The nucleic acid molecules also provide vectors for gene therapy in patients containing cells that are aberrant in secreted protein gene expression. Thus, recombinant cells, which include the patient's cells that have been engineered ex vivo and returned to the patient, are introduced into an individual where the cells produce the desired secreted protein to treat the individual.

The invention also encompasses kits for detecting the presence of a secreted protein nucleic acid in a biological sample. Experimental data as provided in FIG. 1 indicates that isoform 1 of secreted proteins of the present invention are expressed in adult adrenal gland, mammary gland, retinoblastoma, adenocarcinoma cell line, embryonal carcinoma cell line, adult uterus, adult head-neck, and leukocytes. Specifically, a virtual northern blot shows expression in adult adrenal gland, mammary gland, retinoblastoma, adenocarcinoma cell line, embryonal carcinoma cell line, adult uterus, and adult head-neck. In addition, PCR-based tissue screening panel indicates expression in leukocytes. Experimental data as provided in FIG. 1 indicates that isoform 2 of secreted proteins of the present invention are expressed in adult adrenal gland, adult uterus, adult head-neck, adult lung tumor, mammary gland, retinoblastoma, adenocarcinoma, and the hippocampus. Specifically, a virtual northern blot shows expression in adult adrenal gland, adult uterus, adult head-neck, adult lung tumor, mammary gland, retinoblastoma, and adenocarcinoma. In addition, PCR-based tissue screening panel indicates expression in the hippocampus. For example, the kit can comprise reagents such as a labeled or labelable nucleic acid or agent capable of detecting secreted protein nucleic acid in a biological sample; means for determining the amount of secreted protein nucleic acid in the sample; and means for comparing the amount of secreted protein nucleic acid in the sample with a standard. The compound or agent can be packaged in a suitable container. The kit can further comprise instructions for using the kit to detect secreted protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7-20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the secreted proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the secreted protein gene of the present invention. FIG. 3 provides information on SNPs that have been found in the gene encoding the enzyme of the present invention. SNPs were identified for isoform 1 at 36 different nucleotide positions, and for isoform 2 at 34 different nucleotide positions. Changes in the amino acid sequence caused by these SNPs is indicated in FIG. 3 and can readily be determined using the universal genetic code and the protein sequence provided in FIG. 2 as a reference. Some of these SNPs that are located outside the ORF and in introns may affect gene expression. Positioning of each SNP in an exon, intron, or outside the ORF can readily be determined using the DNA position given for each SNP and the start/stop, exon, and intron genomic coordinates given in FIG. 3.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified secreted protein gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a secreted protein or peptide that can be further purified to produce desired amounts of secreted protein or fragments. Thus, host cells containing expression vectors are useful for peptide production.

Host cells are also useful for conducting cell-based assays involving the secreted protein or secreted protein fragments, such as those described above as well as other formats known in the art. Thus, a recombinant host cell expressing a native secreted protein is useful for assaying compounds that stimulate or inhibit secreted protein function.

Host cells are also useful for identifying secreted protein mutants in which these functions are affected. If the mutants naturally occur and give rise to a pathology, host cells containing the mutations are useful to assay compounds that have a desired effect on the mutant secreted protein (for example, stimulating or inhibiting function) which may not be indicated by their effect on the native secreted protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a secreted protein and identifying and evaluating modulators of secreted protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the secreted protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the secreted protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, secreted protein activation, and signal transduction, may not be evident from in vitro cell-free or cell-based assays. Accordingly, it is useful to provide non-human transgenic animals to assay in vivo secreted protein function, including substrate interaction, the effect of specific mutant secreted proteins on secreted protein function and substrate interaction, and the effect of chimeric secreted proteins. It is also possible to assess the effect of null mutations, that is, mutations that substantially or completely eliminate one or more secreted protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:3;
   (b) a nucleotide sequence consisting of SEQ ID NO:1;
   (c) a nucleotide sequence consisting of SEQ ID NO:5; and
   (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. A vector according to claim 2, wherein said vector is selected from the group consisting of a plasmid, a virus, and a bacteriophage.

7. A vector according to claim 2, wherein said isolated nucleic acid molecule is inserted into said vector in proper orientation and correct reading frame such that a polypeptide comprising SEQ ID NO:3 is expressed by a cell transformed with said Vector.

8. A vector according to claim 7, wherein said isolated nucleic acid molecule is operatively linked to a promoter sequence.

* * * * *

SEQUENCE LISTING

<160> NUMBER OF SEQ ID NOS: 7

<210> SEQ ID NO 1
<211> LENGTH: 1722
<212> TYPE: DNA

-continued

<213> ORGANISM: Human

<400> SEQUENCE: 1

```
ttgctcactg ctcacccacc tgctgctgcc atgaggcacc ttggggcctt cctcttcctt      60
ctggggtcc  tgggggccct cactgagatg tgtgaaatac agagatgga cagccatctg      120
gtagagaagt tgggccagca cctcttacct tggatggacc ggctttccct ggagcacttg     180
aaccccagca tctatgtggg cctacgcctc tccagtctgc aggctgggac caaggaagac     240
ctctacctgc acagcctcaa gcttggttac cagcagtgcc tcctagggtc tgccttcagc     300
gaggatgacg gtgactgcca ggcaagcct  tccatgggcc agctggccct ctacctgctc     360
gctctcagag ccaactgtga gtttgtcagg ggccacaagg gggacaggct ggtctcacag     420
ctcaaatggt tcctggagga tgagaagaga gccattgaca cagcagccat ggcaggcttg     480
gcattcacct gtctgaagcg ctcaaacttc aaccctggtc ggagacaacg gatcaccatg     540
gccatcagaa cagtgcgaga ggagatcttg aaggcccaga ccccccgaggg ccactttggg     600
aatgtctaca gcacccatt ggcattacag ttcctcatga cttcccccat gcgtgggca      660
gaactgggaa cagcatgtct caaggcgagg gttgctttgc tggccagtct gcaggatgga     720
gccttccaga atgctctcat gatttcccag ctgctgcccg ttctgaacca caagacctac     780
attgatctga tcttcccaga ctgtctggca ccacgagtca tgttggaacc agctgctgag     840
accattcctc agacccaaga gatcatcagt gtcacgctgc aggtgcttag tctcttgccg     900
ccgtacagac agtccatctc tgttctggcc gggtccaccg tggaagatgt cctgaagaag     960
gcccatgagt taggaggatt cacatatgaa acacaggcct ccttgtcagg cccctactta    1020
acctccgtga tggggaaagc ggccggagaa agggagttct ggcagcttct ccgagacccc    1080
aacaccccac tgttgcaagg tattgctgac tacagaccca aggatggaga aaccattgag    1140
ctgaggctgg ttagctggta gcccctgagc tccctcatcc cagcagcctc gcacactccc    1200
taggcttcta ccctccctcc tgatgtccct ggaacaggaa ctcgcctgac cctgctgcca    1260
cctcctgtgc actttgagca atgccccctg ggatcacccc agccacaagc ccttcgaggg    1320
ccctatacca tggcccacct tggagcagag agccaagcat cttccctggg aagtctttct    1380
ggccaagtct ggccagcctg gccctgcagg tctcccatga aggccacccc atggtctgat    1440
gggcatgaag catctcagac tccttggcaa aaaacggagt ccgcaggccg caggtgttgt    1500
gaagaccact cgttctgtgg ttggggtcct gcaagaaggc ctcctcagcc cggggggctat   1560
ggccctgacc ccagctctcc actctgctgt tagagtggca gctccgagct ggttgtggca    1620
cagtagctgg ggagacctca gcagggctgc tcagtgcctg cctctgacaa aattaaagca    1680
ttgatggcct gtgaaaaaaa aaaaaaaaaa aaaaaaaaa aa                         1722
```

<210> SEQ ID NO 2
<211> LENGTH: 1896
<212> TYPE: DNA
<213> ORGANISM: Human

<400> SEQUENCE: 2

```
ggaggattaa tcagtgacag gaagctgcgt ctctcggagc ggtgaccagc tgtggtcagg      60
agagcctcag cagggccagc cccaggagtc tttcccgatt cttgctcact gctcacccac     120
ctgctgctgc catgaggcac cttggggcct tcctcttcct tctggggtc  tgggggccc     180
tcactgagat gtgtgaaata ccagagatgg acagccatct ggtagagaag ttgggccagc     240
acctcttacc ttggatggac cggctttccc tggagcactt gaaccccagc atctatgtgg     300
```

-continued

```
gcctacgcct ctccagtctg caggctggga ccaaggaaga cctctacctg cacagcctca      360
tgcttggtta ccagcagtgc ctcctagggt ctgccttcag cgaggatgac ggtgactgcc      420
agggcaagcc ttccatgggc cagctggccc tctacctgct cgctctcaga gccaactggc      480
atgatcacaa gggccacccc cacactagct actaccagta tggcctgggc attctggccc      540
tgtgtctcca ccagaagcgg gtccatgaca gcgtggtgga caaacttctg tatgctgtgg      600
aacctttcca ccagggccac cattctgtgg acacagcagc catggcaggc ttggcattca      660
cctgtctgaa gcgctcaaac ttcaaccctg tcggagaca acggatcacc atggccatca      720
gaacagtgcg agaggagatc ttgaaggccc agacccccga gggccacttt gggaatgtct      780
acagcacccc attggcatta cagttcctca tgacttcccc catgcgtggg gcagaactgg      840
aacagcatg tctcaaggcg agggttgctt tgctggccag tctgcaggat ggagccttcc      900
agaatgctct catgatttcc cagctgctgc cgttctgaa ccacaagacc tacattgatc      960
tgatcttccc agactgtctg gcaccacgag tcatgttgga accagctgct gagaccattc     1020
ctcagaccca agagatcatc agtgtcacgc tgcaggtgct tagtctcttg ccgccgtaca     1080
gacagtccat ctctgttctg gccgggtcca ccgtggaaga tgtcctgaag aaggcccatg     1140
agttaggagg attcacatat gaaacacagg cctccttgtc aggcccctac ttaacctccg     1200
tgatggggaa agcggccgga gaagggagt tctggcagct tctccgagac cccaacaccc     1260
cactgttgca aggtattgct gactacagac ccaaggatgg agaaaccatt gagctgaggc     1320
tggttagctg gtagcccctg agctccctca tcccagcagc ctcgcacact ccctaggctt     1380
ctaccctccc tcctgatgtc cctggaacag gaactcgcct gacccctgctg ccacctcctg     1440
tgcactttga gcaatgcccc ctgggatcac cccagccaca agcccttcga gggccctata     1500
ccatggccca ccttggagca gagagccaag catcttccct gggaagtctt tctggccaag     1560
tctggccagc ctggccctgc aggtctccca tgaaggccac cccatggtct gatgggcatg     1620
aagcatctca gactccttgg caaaaaacg agtccgcagg ccgcaggtgt tgtgaagacc     1680
actcgttctg tggttggggt cctgcaagaa ggcctcctca gcccggggggc tatggccctg     1740
accccagctc tccactctgc tgttagagtg gcagctccga gctggttgtg gcacagtagc     1800
tggggagacc tcagcagggc tgctcagtgc ctgcctctga caaaattaaa gcattgatgg     1860
cctgtgaaaa aaaaaaaaaa aaaaaaaaaa aaaaaa                                1896
```

<210> SEQ ID NO 3
<211> LENGTH: 376
<212> TYPE: PRT
<213> ORGANISM: Human

<400> SEQUENCE: 3

```
Met Arg His Leu Gly Ala Phe Leu Phe Leu Leu Gly Val Leu Gly Ala
  1               5                  10                  15

Leu Thr Glu Met Cys Glu Ile Pro Glu Met Asp Ser His Leu Val Glu
             20                  25                  30

Lys Leu Gly Gln His Leu Leu Pro Trp Met Asp Arg Leu Ser Leu Glu
         35                  40                  45

His Leu Asn Pro Ser Ile Tyr Val Gly Leu Arg Leu Ser Ser Leu Gln
     50                  55                  60

Ala Gly Thr Lys Glu Asp Leu Tyr Leu His Ser Leu Lys Leu Gly Tyr
 65                  70                  75                  80

Gln Gln Cys Leu Leu Gly Ser Ala Phe Ser Glu Asp Asp Gly Asp Cys
```

-continued

```
                85                  90                  95
Gln Gly Lys Pro Ser Met Gly Gln Leu Ala Leu Tyr Leu Leu Ala Leu
            100                 105                 110

Arg Ala Asn Cys Glu Phe Val Arg Gly His Lys Gly Asp Arg Leu Val
            115                 120                 125

Ser Gln Leu Lys Trp Phe Leu Glu Asp Glu Lys Arg Ala Ile Asp Thr
            130                 135                 140

Ala Ala Met Ala Gly Leu Ala Phe Thr Cys Leu Lys Arg Ser Asn Phe
145                 150                 155                 160

Asn Pro Gly Arg Arg Gln Arg Ile Thr Met Ala Ile Arg Thr Val Arg
                165                 170                 175

Glu Glu Ile Leu Lys Ala Gln Thr Pro Glu Gly His Phe Gly Asn Val
            180                 185                 190

Tyr Ser Thr Pro Leu Ala Leu Gln Phe Leu Met Thr Ser Pro Met Arg
            195                 200                 205

Gly Ala Glu Leu Gly Thr Ala Cys Leu Lys Ala Arg Val Ala Leu Leu
        210                 215                 220

Ala Ser Leu Gln Asp Gly Ala Phe Gln Asn Ala Leu Met Ile Ser Gln
225                 230                 235                 240

Leu Leu Pro Val Leu Asn His Lys Thr Tyr Ile Asp Leu Ile Phe Pro
                245                 250                 255

Asp Cys Leu Ala Pro Arg Val Met Leu Glu Pro Ala Ala Glu Thr Ile
            260                 265                 270

Pro Gln Thr Gln Glu Ile Ile Ser Val Thr Leu Gln Val Leu Ser Leu
            275                 280                 285

Leu Pro Pro Tyr Arg Gln Ser Ile Ser Val Leu Ala Gly Ser Thr Val
        290                 295                 300

Glu Asp Val Leu Lys Lys Ala His Glu Leu Gly Gly Phe Thr Tyr Glu
305                 310                 315                 320

Thr Gln Ala Ser Leu Ser Gly Pro Tyr Leu Thr Ser Val Met Gly Lys
                325                 330                 335

Ala Ala Gly Glu Arg Glu Phe Trp Gln Leu Leu Arg Asp Pro Asn Thr
            340                 345                 350

Pro Leu Leu Gln Gly Ile Ala Asp Tyr Arg Pro Lys Asp Gly Glu Thr
            355                 360                 365

Ile Glu Leu Arg Leu Val Ser Trp
        370                 375

<210> SEQ ID NO 4
<211> LENGTH: 400
<212> TYPE: PRT
<213> ORGANISM: Human

<400> SEQUENCE: 4

Met Arg His Leu Gly Ala Phe Leu Phe Leu Leu Gly Val Leu Gly Ala
1               5                   10                  15

Leu Thr Glu Met Cys Glu Ile Pro Glu Met Asp Ser His Leu Val Glu
            20                  25                  30

Lys Leu Gly Gln His Leu Leu Pro Trp Met Asp Arg Leu Ser Leu Glu
        35                  40                  45

His Leu Asn Pro Ser Ile Tyr Val Gly Leu Arg Leu Ser Ser Leu Gln
    50                  55                  60

Ala Gly Thr Lys Glu Asp Leu Tyr Leu His Ser Leu Met Leu Gly Tyr
65                  70                  75                  80
```

-continued

Gln Gln Cys Leu Leu Gly Ser Ala Phe Ser Glu Asp Asp Gly Asp Cys
                85                  90                  95

Gln Gly Lys Pro Ser Met Gly Gln Leu Ala Leu Tyr Leu Leu Ala Leu
            100                 105                 110

Arg Ala Asn Trp His Asp His Lys Gly His Pro His Thr Ser Tyr Tyr
            115                 120                 125

Gln Tyr Gly Leu Gly Ile Leu Ala Leu Cys Leu His Gln Lys Arg Val
        130                 135                 140

His Asp Ser Val Val Asp Lys Leu Leu Tyr Ala Val Glu Pro Phe His
145                 150                 155                 160

Gln Gly His His Ser Val Asp Thr Ala Ala Met Ala Gly Leu Ala Phe
                165                 170                 175

Thr Cys Leu Lys Arg Ser Asn Phe Asn Pro Gly Arg Arg Gln Arg Ile
            180                 185                 190

Thr Met Ala Ile Arg Thr Val Arg Glu Glu Ile Leu Lys Ala Gln Thr
        195                 200                 205

Pro Glu Gly His Phe Gly Asn Val Tyr Ser Thr Pro Leu Ala Leu Gln
    210                 215                 220

Phe Leu Met Thr Ser Pro Met Arg Gly Ala Glu Leu Gly Thr Ala Cys
225                 230                 235                 240

Leu Lys Ala Arg Val Ala Leu Leu Ala Ser Leu Gln Asp Gly Ala Phe
                245                 250                 255

Gln Asn Ala Leu Met Ile Ser Gln Leu Leu Pro Val Leu Asn His Lys
            260                 265                 270

Thr Tyr Ile Asp Leu Ile Phe Pro Asp Cys Leu Ala Pro Arg Val Met
        275                 280                 285

Leu Glu Pro Ala Ala Glu Thr Ile Pro Gln Thr Gln Glu Ile Ile Ser
    290                 295                 300

Val Thr Leu Gln Val Leu Ser Leu Pro Pro Tyr Arg Gln Ser Ile
305                 310                 315                 320

Ser Val Leu Ala Gly Ser Thr Val Glu Asp Val Leu Lys Lys Ala His
                325                 330                 335

Glu Leu Gly Gly Phe Thr Tyr Glu Thr Gln Ala Ser Leu Ser Gly Pro
            340                 345                 350

Tyr Leu Thr Ser Val Met Gly Lys Ala Ala Gly Glu Arg Glu Phe Trp
        355                 360                 365

Gln Leu Leu Arg Asp Pro Asn Thr Pro Leu Leu Gln Gly Ile Ala Asp
    370                 375                 380

Tyr Arg Pro Lys Asp Gly Glu Thr Ile Glu Leu Arg Leu Val Ser Trp
385                 390                 395                 400

<210> SEQ ID NO 5
<211> LENGTH: 27067
<212> TYPE: DNA
<213> ORGANISM: Human
<220> FEATURE:
<221> NAME/KEY: misc_feature
<222> LOCATION: (1)...(27067)
<223> OTHER INFORMATION: n = A,T,C or G

<400> SEQUENCE: 5
atatgtatgg gaaatatgct gtcttcctat tcctactccc ccaccctcta gcactgagtc      60
caggtaggta ggcagggggg tgtctccctc ctttacttcg acaccctaac taccttgggg    120
atcagaagtg actctctgga aggatgctgc tgcttctcac cagaggctga cgataacgaa    180
ggctatcctc catggccacc tcctccaggc tgccttcctg gaaataggaa tcataatagt    240

-continued

```
tgttactgga aacaggcaga gggttggggg agccaaggca gtcccaccca ggaccaaggt      300
ggctccattg cacacacttc accatgactc ccctgaaggt ccaaacgtgc ggttctgcgg      360
aagttgggct ccccactggc ctccctcctt cctcagaacc tccaggggtg ctcctcctag      420
tggccacatc cagcctttct gactggacaa cctatcattt aaaattttca gtagttccg       480 taaacagaca cacgttgctg tatttattta tgtcaagggc ttggtttgtg ataagtcagg      540
ctcaaaaaga ttgtcttaaa agagtgaacc ttggcaattt accataaaat aattgcaatg      600
cagattgtgc atggaaatga ttggagatat tttaaggtca tagtgtcttc acaaattgag      660
ctgaaaggga actgttagga tgatcttgcc taaccctctc atctcacaca ggaagaacta      720
ttttaaactc gagaggttaa gtgacctggc caaagtcaca cagccaccac tagttaactc      780
gtatacattg attctcctgt ggggctgggc agatgaggaa tcttttgttc tcttccctgt      840
ttgcagagat tttttttgag gttactttcc gagttctggc aagtacccct gcttctggta      900
gctttgtgtc tcgattcaat ctcattcttt ttattttatt ttattttga gacagggtct       960 cactttgtca cccaagctgg agtgcagtgg tgtaatcttg gctcactgta gcctccacct      1020
cttgggttca gcgatcctc ctgcctcagc ccccaagta gctgggatta cagacgtctg        1080
ccaccacgcc aggctaattt atggtttttt gtatgtgttt tttgtgtttt tgtagagaca      1140
gtgtttcccc atgttgccca ggctggtctc caactcctga gctcaagtga tctgcccgcc      1200
tcagcctttc aaagtgctag gattacaggt gtgagccacc gtgcccggac ttaatcccat      1260
tctttaactt gttttgtttt gtcctctcca ggaggctccc agcccttcg gattggttga       1320 gaaaagtggc ctggctggtc tggggccagc agcacccacc ctcccctcaa ttgcccaact      1380
ccccccccca ccgaactgcc caactccccc tcccaactg cccaactccc ccaccccac        1440 aatccctcc cgccacaact gagggaggcg gtgctgaaaa acagctgact ccagcaatgc       1500
tgctcacgtg accactgcag ctgcagctcc cgttccactc cttgtcctgg gctaggtggg      1560
cactaccagg ggctccttg gtaaggagta ccgggtaggc acccggtcct gccaatccac       1620
cactggaaca gctgggggga cagcagacag gcacggtcgg acagacttga cagatcaggc     1680
atcaggccct ctgcgctggt cccgggctct ttaagcagga acgtgaatgg cctcaagatg     1740
tctcacatgg tcccactagc cctcctcctc cctttgttcc ctacctccag gagggctgct    1800
ctgcccttcc ttcctctgtt ctttggcctt atgttccccg ccaccacagg ccttcccccg    1860
ccccacccct ctgcagactt agccgtgcat tgcaggcatg gaggattaat cagtgacagg    1920
aagctgcgtc tctcggagcg gtgaccagct gtggtcagga gagcctcagc agggccagcc    1980
ccaggagtct ttcccgattc ttgctcactg ctcacccacc tgctgctgcc atgaggcacc    2040
ttggggcctt cctcttcctt ctgggggtcc tgggggccct cactgagatg tgtggtgagt    2100
aactcgcctc tatcctgtgc ctctttcctc ctgggtcctt agtggggtgg ctagggcata    2160
ggatgaggga acttacctgc ccttctaagc tcccatagca gtttgggctt agctggacct    2220
cagcatttaa cacatcctat tgtgattgat tatatgtttg actcctcacc agacaagatc    2280
tccgttaatt cagtcattcg ttcacacatt cattcagcgc atactgagcc ttttctgtgt    2340
caggcccagt gttagccttt ggggaacgtg caaagcatga acaagtcta atccctgcca     2400 tcctagagct tatgttctag ggaagggga cagacaaaag aaatggttag gtgctcccac     2460
ctgaaatctc agcattttgg aaggctgagg cgggagggga ggatcgcttg agctcaacag    2520
ttcaaggtca gcctgggcaa cataggggaga ccccatctct acaaaaaata aaaaaaatta   2580
```

```
aaaaatagct gggcatgggg aagactttct gaagaccaag aggacacatg ggagctgaaa    2640
ctcgaaggaa gaaaaggagc tggcaggaaa ggagtggggg acacacattc taggcagcag    2700
gaagtgagcc ttcggaggtc ctgcctgctc cagctctgtg ccccaagggg tctcttggag    2760
cacagtctcc tgggacctgt ctatgagtct gagcttagag gctcagggct gctccttcag    2820
acaggaggca gaaggcagac tttgggaact ttgggccgcc cacgcgcctt ttctcctcct    2880
ctgcacctag gattacgttg agcaatacac tttcacccccc atggtctctt gagaccctgg   2940
ggaaaccctg agaggtgggt gcagtcatgt ccaggtgtca agtgaagaag tcgagggttg    3000
gaggggctga gtgacccact caggtgctc  cacctttcc agagctttgc tgaacttagt    3060
ttttagaact tgaagcctcg tttgttttcg ttttgttttt tgttgagaga ggttctccct    3120
ctgttgccca ggctggagtg cagtggcacg atcttggctc actgcagcct ctgccttgtg    3180
ggttcaagtg attcccccac ctcagcctcc caagtagctg gagactgcat gtgcatacta    3240
ccatgcttgg ctaattttttg tatttttttg tagagacagg gtttcgccat gttgcccagg   3300
ctggtctcga actcctgggc tcaagtgaaa ctcttgcctc ggcctcccaa attgctgaga    3360
ttacaggcgt gagccaccgt gcccggccag aactccaagc ctctcatctg tgttccataa    3420
atgcaatcag acacctcagg tctgggccca ggaaccccag ctcttggttc atgtccggac    3480
agtccccagg ggagttctgg gttcaaccag caagagctct tcctcctggc tgatctggtc    3540
ctcagccttg acagttagt ccattaacct gaccccacag gagccccaat cccttggggt     3600
ctggggaatc ttgaactggg gtttgggggtg caaatatctg cactgagtca cttaattgca   3660
cccagcctca ttcctttatc tgtaaagtgg gctaagaatg ctcccctgcc ttcctcctcg    3720
gtgtagtacg aggaaggatc ccatgacacc tgctctccca gtttaaagct ctatatgtat    3780
gttgtgaaat tgacagggat cgctgcacaa acgctaatgc aaagtgggct cctgtgcttc    3840
cttttctctt tcttcttctt tttttttttt ttaattttct tctagagatg aggtctcact    3900
atattgccca gggttggttt caaactccta gggtcaagcg atcctcccac cttggcctcc    3960
caaactgctg gtattacagg cgtgagccac tctgtctggc tcctatgctt gtgaatgtca    4020
acagcaatca gcccttagct ggcagggctg ggttggtagg gcgagagctc acccaaggct    4080
gcttttatta ccctgcgtga atctgcctgg cccccttcctt ctaaggaggt tgctctgtgg   4140
ttgtcagtct ctcccttttac agctggatcc tgatctttca gtttctaacc ctgtgctgac   4200
tcatcgtgct ggaagtgaga gcccggggtg aggtcaggga actcccttgc gcgtttcaag   4260
aaaagggaaa aggaaagaga ggtgaggagg ggggcagatg accagagaga cacaggctga    4320
gagagactga gacagaccca gagagcctca cacattgagt gacagagacg gagaaatgga    4380
gataggcacc aaaaaatggt tctcagtgac agaaagggaa aaaagcaacc ccccagtctc    4440
tcttaacatc tggtgagaaa ccagccatgt gctttggtct gggcccacac agcaaaggat    4500
tatgtagggt ttcatgctgg tggatggtca ccttatagca acaggtatct ggggctgtcg    4560
ggaaaacaga cacgaggttg tgggaccccag acccacagag atggagctgt tctaggagct   4620
ctggtcctcg ttctggtccc ctgggatatg gcacagtgaa ggccaccatc aggcagctgg    4680
agcccagcag caactgggag gcagtaaaca gggaccgaaa gtgcaaggtt acctccgagg    4740
caaactactc taagctaccc tgtgctgagc tcaagtccct tggaactatc cctaaggctt    4800
ccgcttccag agtgtttgag tattttcgtt gcacagcttc gaataaatcc cacagcaaca    4860
ggtaaacggc tgcaagctgt gactgttttc taagagctca tctcacaatc tcaggtcctc    4920
ttcatttaaa cagagatggc aggaaaggcg ttattttgag atctgcatgg aggaagttca    4980
```

-continued

```
ccaggcagcc tcaattcacc agctggaagt ttgcgttgtt tggaaatttg atgtgtaaca    5040
cgttctgcat gtgggctgat gttttttgtaa acgggtagca cacacattca gcagggcacc   5100
aaagagcggg ggctttgcag ttaggtccat ccttggctct gcagccttgt gtaagacatg    5160
acacgacttt gaacttctgt ttcctcttct gtgcaaagca atgatgacag tatctacatc    5220
acaggactgg catgaggacc aagtgagatt gggcaaggtg cccgggcaca ccagtctcac    5280
tgtcactgct gatgggcaga gtggttgcct ggcagtagca tcctctatct tcagcccacc    5340
acctctcttg ctggctcact ccaactgctc tttagagata cacgcttccc ctctttttctc   5400 ctcccactgc ctttcagtat ggctgcattt cccctgcaa gttggtgtgt gctgggtgga     5460
ggtgggggtg aggacatgta ttctctggag aaggccctgg taacgtcaaa gcacttcttt    5520
gctggtggcc tggccctgtg acctcatttg taccatttc ttttctaaga ataccagag      5580 atggacagca atctggtaga gaagttgggc cagcacctct taccttggat ggaccggctt    5640
tccctggagc acttgaaccc cagcatctat gtgggcctac gcctctccag tctgcaggct    5700
gggaccaagg aagacctcta cctgcacagc ctcaagcttg gttaccagca gtgcctccta    5760
gggtattgcc acactctctt tttccatgtc ttgctccaca tactaagaga tgggaaactt    5820
gggtactagt ttgggcctgt caccacttg tgggcagacc ttaggcaaat tttctccatc     5880
tatagaatgg aggacctttg tccatctata gaatgaaggg gttggttgga ttagatcaga    5940
gatgctaatg caaggctcct tttgctacta ctgtccatca tgtgtctgag gcagacataa    6000
ctaatccgtg actatactct tgatgatga gcccaggagc agcatctgac tctatgctcc     6060
cttagtgtgc ctgaggcaga tatcactaat cgatgactgc agtcttctac attgagctta    6120
gaagcagcat ctgactctgt atgctcccct cccatgcatg aggcagacat cagtaatcca    6180
tgaccgcatt ctttcatact gagcccagaa gcagcatctt ttcttttctt tcctctcact    6240
ctgttgccca ggctagagtg cagtggcaca atcttggctt gccccaacct ccaattcccg    6300
ggttcaagtg attctcgtgc ctcagccacc tgaatagctg ggattacagg cgtgtgccac    6360
catgcccagc tgattttgt attttggta gagatagggt ttcaccatgt tggccaggct      6420
ggtcttgaac tcctgacctc aggtgatccg cctgtcttgg cttcccaaag tgttgggatt    6480
ataggcatga gccactgcac caatccaaaa gcagcatctt tgtgctccct tttcaagagg    6540
catcacagag aggcctgttt tggggtttga atgagaggcg aagaatcagc catggagtgc    6600
ctctttctca gactccctct tgagaagtgg gtgcaggggt ggagagaaaa gaagactagg    6660
catagtggct catacctgta atcccaacat tttgggaggc tgaggcagga agattgcttg    6720
agctcaggag tttgagacca gcctaggcaa catagtgaga ccacatctct taaaaaaag    6780 aaaaagaaaa aaaatgagcc aggtgtagtg actcatgcct gtggtcccca cttctccgga   6840
ggcaaaggtg ggaggatctt ttgaggctga gaaatcgagg ctacagtgag ccatggtggc    6900
accactgcac tccagcctgg gagacagaga gaccctatct cagtaaaaaa aaaaaataaa   6960
aatatgcgct ggtgtggtgg ctcacgcctg taatcccagc actttgggag gccaaggtag    7020
gtagatcaca tgaggttagg agttcgaaac cagtctggcc aacatagtga aaccctgtct    7080
ctactgaaaa tacaaaaaat tagccaaggg tggtggtggg caactgtaat cccagctact    7140
tgggaggccg aggcagaaga atcgcttgaa ctcgggaggc ggaggttgca gtgagctgag    7200
aacatgccac tgcactccag cctgggcaac aagagcgaaa ctctgtctca aagaaaataa    7260
ataaataaaa taaaaaaata aaaaggagg gggcatatgg gtgaagtatg gacaaaatag     7320
```

-continued

```
tggggcaggc acagatgatc tggacacagg agcccttgga gtttattctt gaatctaact    7380
gttcatcttt attaaatatt tgtggcatac acctcacaac aacatagcca acacacctcc    7440
ttttggagct tttatcgaag tttcccactg ttaagatttt ttcccgcttt gtgatgcggg    7500
tggggtgggt gctgtaagca ggcttacggg gtggcagttt ctcacaaagg cattaactgg    7560
ccttgtccta ggtctgcctt cagcgaggat gacggtgact gccagggcaa gccttccatg    7620
ggccagctgg ccctctacct gctcgctctc agagccaact gtgagtttgt caggggccac    7680
aaggggggaca ggctggtctc acagctcaaa tggttcctgg aggatgagaa gagagccatt    7740
ggtgagcaga caccatccgc tgggggtggg gagcagctgg gagggctcat cagatgatat    7800
tctccaatga gaatcagaac tttgggtttt ctccccaggc gtctttccca ccatccattc    7860
tgcccatctc actgcctacg tagaggctcg aacctgtccc catagccatc cttgacccag    7920
cttttcccgc gctgcacaca tactattgac aggtgtgttt cgtggttttt tgttttttgt    7980
ttgtttgttt gttttgagtt ggaggtttgc tcttgctgcc caggctggag tacaatggcg    8040
caatctcagc tcaccgcaat ctctgcctcc tgggttcaag caattctctt gcctcagcct    8100
cctgagtagc tgggattaca ggcatgcgcc accacaccca gctaattttg tattttttagt   8160
agacgtgggg tttctccatg ttggtcaggc tggtctcgaa ctcctgacct caggtgatcc    8220
gcttgcctta gcctccgaaa gtgctgggat tacaggcatg agccactgcg ttaggcccac    8280
tgacaagcct tgtattggct agccaccaag attgacttga ttatccacct tcgggacaac    8340
tggacagcct gcttatgact tacgccatag tctgtctcta ctagctctcc tgccctgact    8400
tgacccagca tacaacagcc agagccagcc ttttcaatat aaacctgatc ttgctggcac    8460
tgcttaaacc ctgcagggggc ctcgcactgc tccatggccc agcctgtcta cccttacctt    8520
ctgcccaggc tctgctcatc cattctctgc ctcccacaca cctgccctct gtgggctcca    8580
gccataccat ctctcaactc ataagccagt tttttcatac aggctccctc catctggact    8640
ggcttccctg cgtgcagttc actcctgctc tacctttggc tctgcctcca cccatcctca    8700
gccgtctcca gcattacctc cttggagaat cctgccttga cttcccagcc acccaaatat    8760
cactacttgg tctgcattct cgttgcaatt gcagtcgcat gagcaattgc tgtggttgag    8820
gcccgaactg cgcaagtgcc tgtctgccat gggtctcctg cttcctctaa gcacagtgcc    8880
tgacacacag tgagacctca gcacgtatgg gctgaggcaa tgaaggaatg aaggatccca    8940
tgacccaaaa gagcctgttg gaaagtgcag gccagggtcc caggtgctgg cggggctggc    9000
tgctgggtgg gggcagagag gcaacccctc tgtttttttc cctctcaggg catgatcaca    9060
agggccaccc ccacactagc tactaccagt atggcctggg cattctggcc ctgtgtctcc    9120
accagaagcg ggtccatgac agcgtggtgg acaaacttct gtatgctgtg gaacctttcc    9180
accagggcca ccattctgtg ggtgagtagg tcagaccgtg ccaaggccag gctggcactc    9240
cctcagtccc caggtctgca ctgatgacgt ccatacctg gcccccacac tcacctttcc    9300
ttggggctcc tccgaatcaa gtcctttagg gacgaattgg cgagggctca tgggtgatgc    9360
tccagctgtg agccagcttt ggagctggta ggtggatctc ttgaggccag gagttcaaga    9420
caacgtggtg aaaccccatc tctactaaaa ataaaaaagt tagccgggca tggtggcaca    9480
tgcctgtagt cccagctact cgggaggctg aggcaggaga atcacttgaa cctggggaggc    9540
ggaggctgca gtgagtggag atcgcaccac tgccctccag cctgggcaac agagtgagtg    9600
agactctgtc tcaaaaaata aaaataaaa taaaactccc ctagtgattc caatgtgcag    9660
ctaagtttgg aaataggtgg tatggggtca agtcctcttg ggcctccctc ctccagtcct    9720
```

-continued

```
tctccctaac ctctagccct caagttgcag agtgatcagc caaaccagtt tgcccagaaa    9780
tgagcagttt cctgggacac aggattttca gagtccagac aaggaaagtc ttgggcagac    9840
caggttgagt tggtgccctt agctgatctg accatgttgc ccttcttctc caagccctcc    9900
tgtggttgtc catagctaca agggcctgac cctcaagccc ctgcctgtcc tggccccttt    9960
ggctctccag ctcattgcat gttctgtccc ccacttcaag acacagcagc catggcaggc   10020
ttggcattca cctgtctgaa gcgctcaaac ttcaaccctg tcggagaca acggatcacc    10080
atggccatca gaacagtgcg agaggagatc ttgaaggccc agaccccga gggccacttt    10140
gggaatgtct acagcacccc attggcatta caggtgggaa agagaccctg gagccatggc   10200
caccctgggg aacagtcggg tggagtggtc aggtgctgga cacctagcc cctccctgcc    10260
ggctgacctc ctctctctct tcctcactct atcaccagtt cctcatgact tcccccatgc   10320
ctggggcaga actgggaaca gcatgtctca aggcgagggt tgctttgctg ccagtctgc    10380
aggatggagc cttccagaat gctctcatga tttcccagct gctgccgtt ctgaaccaca    10440
agacctacat tgatctgatc ttcccagact gtctggcacc acgaggtagc ccaacttttt   10500
gtggaagcac agccctttac aatctgctgc gcacccattg acgtcccagt gaggggaggt   10560
tgcttcatcc tgatttgctg agtcagcaca agtttgtggg tgtgcatggg acacagtagc   10620
caaaatgtgg tcatagcttc tagaagctca cagtgtgggg aggaagacag taaatggaga   10680
tccctgggca tatcgcttgt gtgatacca gtacagaaat gttggatgg atggatggat    10740
ggatggatgg atggatggat ggatggatgg atgaggagag acacattttg gttaactcta   10800
atacaacatg ataagcccca gtagcagcat gatccaggct ttctctgaga gagggtctga   10860
ggacgtgact gggatttgcc aattaagaat ggagaaagag gccaggtgca gtgactcatg   10920
cctgtaatcc caacactttg ggaggccgag gcgggtggct cacctgaggt caggagttcg   10980
agaccagcct ggctaacatg gcgaaactcc atctattaaa aatacaaaaa agtagctggg   11040
tgtggtggcg agtgcctgta acccagcta agctactcag gaggctgagg caagagaatc    11100
acttgaacct cagaggtgga ggttgcagtg agccaagatc atgccactgc actccagtct   11160
gggtgacaga gtaagactat gtctcaaaaa aaaaaaaaa aaatggagaa gaaggaagct   11220
ggacatggtg gctcgtgctt ataatcctag cactctggga agctgaggca gatggattgc   11280
ctgagcccag gagtttgaga ccagcctggg caacatggtg aaaccctgtc tttactaaaa   11340
tacgaaagat tagccaggca tggtggtaga cacctataat cccagctact agggaggctg   11400
agccacaaga atcacttgaa cctgggagac agaggttgca gtgagccgag atcgcgccat   11460
tgcactccag cctgggcgac agtgtgagac tctgtctcca gaaaaacaa gaatggatag    11520
agtggagcca agaagaggca ggaagaacaa agacacagag gtgcacagag tttgggggaa   11580
ttttgaggaa tggtcttgca aaagagtggg atctgggaga atgagtggga gtggaaagca   11640
gatgaatgaa gagaaggtga gcgcatcagg gtaacagaga tgcgttgtga acaaatgcat   11700
gttctaggaa gagccctctg gagtgctagg tgccagagag tgggaggaa ggatactgga    11760
agcagagaaa ccagtgaggg gcctgatctt gggtggtggg gaatgaggga caggggaggc   11820
cgggatggaa gccaggtggt ggggaatgag ggacagggga ggccgggatg gaagccaggt   11880
ttcagctgag caggtggcgg tggcattgat ggagatgagg acatggggaa ggacaaagtc   11940
caggtgtcct tgagggaaga caagaagaca ataatccag gctctctgtc ctcacaccag    12000
ctgcccgccc cttctcttcct ggcacagtca tgttggaacc agctgctgag accattcctc   12060
```

```
agacccaaga gatcatcagt gtcacgctgc aggtgcttag tctcttgccg ccgtacagac   12120
agtccatctc tgttctggcc gggtccaccg tggaagatgt cctgaagaag gcccatgagt   12180
taggaggatt cacgtgagac tcccacctcc cagtcctcac cccacccaac ctcacatgcc   12240
tgataacagg gtcacagaaa agacggggaa cagaggagag ggttccctcg ggagagacac   12300
tggccctgct tctgcttcta cctgctcagc tcctttcttg cccacggtgt tatggaaaca   12360
gggagccata ggccagcatt gtcactgaga gagcaggctt tggaggcaga gccccccagt   12420
tggaatccca actctaacca gctaggttcc agtaggcac ccacaattca ccgaggagaa    12480
cagttgtgcc ccttccctgc agggccagtg tgaagagtcc aggagttagt acacatagag   12540
atagtggcat gtgctttta tatgtgcaag gtccagcaca tagcaagcgc tcaacacagc    12600
gttgctttca tcagagtaag aactgttttt tgtttgtttg tttgtttgtt tttaagagac   12660
agggtctcaa tcttatcacc caggctggag tgtaattgtg caatcacgtc tcactgcagt   12720
ctcgaactct ggggatgaag caaccctact gtcctgcctc agcctcccaa atagctgaga   12780
ctataggcac gtgccacaca accctgggta attttttttt ttttttttttt gagatagggt  12840 ctctgtctgt tgcccaggct ggtctcaaat tcctggcctc aaaccatcct cacacctgag   12900
gcgctcaaaa tattgggatt ataggtgcga gccatcatgc tcagccagaa taataactgg   12960 tttttttgt tttttttg agacagagtc tcactctatt acccaggctc tggaggccca      13020
actcgtgttt gtgtatttgt ttatttttat ttatttattt atttcgagac agagcctctc   13080
tctttcacct aggctggagt gcagtggcgc aatctcggct cactgcaacc tccgtctcct   13140
gggttcaagt gattgtcctg cctcagcctc ctgagtagct ggtgctacag gcgcgtgcca   13200
ccatgcccag ctaattttg tatttttagt agagacaggg ttttactatg ttggccagct    13260
ggtttctaac tcctgaactc gggtgatctg cctgcctcgg cctcccaaag tgctgggatt   13320
acaggcatgg gcctccgtgc ccggccatgt atttatttag gcaaggtctc tctctgttat   13380
ccaggctgaa gtgcagtggc acattcatag ctcactgcag cctcaaatta tccaagtaac   13440
agggactaca ggcatgcacc accacaccca tctactttt tttgagatgg agtctccctc    13500
tgtcgcccag actgggttgc agtggcacaa tttcagctca tggcagcatc tacctcccag   13560
gttcaagcga ttctccttcc tcagtctccc gagtagctgg gactatgggc atgcaccacc   13620
atacctggct aatgtttata ttttgagtag agatggaatt ttgccatttt ggccaggctg   13680
gtcttgagct cttgacctca agtgatatgt ctgcctcagn nnnnnnnnn nnnnnnnnnn    13740 nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnnnn nnnnnnnnnn nnnnnnnnnn    14160
nnnnnnnnnn nnnnnnnnnn nnnnnnnnnn nnnnnnnnnn nnnnnnnnnn nnnnnnnnnn    14220
nnnnnnnnnn nnnnnnnnnn nnnnnnnnnn nnnnnnnnnn nnnnnnnnnn nnnnnnnnnn    14280
nnnnnnnnnn nnnnnnnnnn nnnnnnnnnn nnnnnnnnnn nnnnnnnnnn nnnnnnnnnn    14340
nnnnnnnnnn nnnnnnnnnn nnnnnnnnnn nnnnnnnnnn nnnnnnnnnn nnnnnnnnnn    14400
nnnnnnnnnn nnnnnnnnnn nnnnnnnnnn nnnnnnnnnn nnnnnnnnnn nnnnnnnnnn    14460
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 14520 |
| nnnnnnnnnn | nnnnnnnnnn | nnnnnnnnnn | nnnnnnnnnn | nnnnnnnnnn | nnnnnnnnnn | 14580 |
| nnnnnnnnnn | nnnnnnnnnn | nnnnnnnnnn | nnnnnnnnnn | nnnnnnnnnn | nnnnnnnnnn | 14640 |
| nnnnnnnnnn | nnnnnnnnnn | nnnnnnnnnn | nnnnnnnnnn | nnnnnnnnnn | nnnnnnnnnn | 14700 |
| nnnnnnnnnn | nnnnnnnnnn | nnnnnnnnnn | nnnnnnnnnn | nnnnnnnnnn | nnnnnnnnnn | 14760 |
| nnnnnnnnnn | nnnnnnnnnn | nnnnnnnnnn | nnnnnnnnnn | nnnnnnnnnn | nnnnnnnnnn | 14820 |
| nnnnnnnnnn | nnnnnnnnnn | nnnnnnnnnn | nnnnnnnnnn | nnnnnnnnnn | nnnnnnnnnn | 14880 |
| nnnnnnnnnn | nnnnnnnnnn | nnnnnnnnnn | nnnnnnnnnn | nnnnnnnnnn | nnnnnnnnnn | 14940 |
| nnnnnnnnnn | nnnnnnnnnn | nnnnnnnnnn | nnnnnnnnnn | nnnnnnnnnn | nnnnnnnnnn | 15000 |
| nnnnnnnnnn | nnnnnnnnnn | nnnnnnnnnn | nnnnnnnnnn | nnnnnnnnnn | nnnnnnnnnn | 15060 |
| nnnnnnnnnn | nnnnnnnnnn | nnnnnnnnnn | nnnnnnnnnn | nnnnnnnnnn | nnnnnnnnnn | 15120 |
| nnnnnnnnnn | nnnnnnnnnn | nnnnnnnnnn | nnnnnnnnnn | nnnnnnnnnn | nnnnnnnnnn | 15180 |
| nnnnnnnnnn | nnnnnnnnnn | nnnnnnnnnn | nnnnnnnnnn | nnnnnnnnnn | nnnnnnnnnn | 15240 |
| nnnnnnnnnn | nnnnnnnnnn | nnnnnnnnnn | nnnnnnnnnn | nnnnnnnnnn | nnnnnnnnnn | 15300 |
| nnnnnnnnnn | nnnnnnnnnn | nnnnnnnnnn | nnnnnnnnnn | nnnnnnnnnn | nnnnnnnnnn | 15360 |
| nnnnnnnnnn | nnnnnnnnnn | nnnnnnnnnn | nnnnnnnnnn | nnnnnnnnnn | nnnnnnnnnn | 15420 |
| nnnnnnnnnn | nnnnnnnnnn | nnnnnnnnnn | nnnnnnnnnn | nnnnnnnnnn | nnnnnnnnnn | 15480 |
| nnnnnnnnnn | nnnnnnnnnn | nnnnnnnnnn | nnnnnnnnnn | nnnnnnnnnn | nnnnnnnnnn | 15540 |
| nnnnnnnnnn | nnnnnnnnnn | nnnnnnnnnn | nnnnnnnnnn | nnnnnnnnnn | nnnnnnnnnn | 15600 |
| nnnnnnnnnn | nnnnnnnnnn | nnnnnnnnnn | nnnnnnnnnn | nnnnnnnnnn | nnnnnnnnnn | 15660 |
| nnnnnnnnnn | nnnnnnnnnn | nnnnnnnnnn | nnnnnnnnnn | nnnnnnnnnn | nnnnnnnnnn | 15720 |
| nnnnnnnnnn | nnnnnnnnnn | nnnnnnnnnn | nnnnnnnnnn | nnnnnnnnnn | nnnnnnnnnn | 15780 |
| nnnnnnnnnn | nnnnnnnnnn | nnnnnnnnnn | nnnnnnnnnn | nnnnnnnnnn | nnnnnnnnnn | 15840 |
| nnnnnnnnnn | nnnnnnnnnn | nnnnnnnnnn | nnnnnnnnnn | nnnnnnnnnn | nnnnnnnnnn | 15900 |
| nnnnnnnnnn | nnnnnnnnnn | nnnnnnnnnn | nnnnnnnnnn | nnnnnnnnnn | nnnnnnnnnn | 15960 |
| nnnnnnnnnn | nnnnnnnnnn | nnnnnnnnnn | nnnnnnnnnn | nnnnnnnnnn | nnnnnnnnnn | 16020 |
| nnnnnnnnnn | nnnnnnnnnn | nnnnnnnnnn | nnnnnnnnnn | nnnnnnnnnn | nnnnnnnnnn | 16080 |
| nnnnnnnnnn | nnnnnnnnnn | nnnnnnnnnn | nnnnnnnnnn | nnnnnnnnnn | nnnnnnnnnn | 16140 |
| nnnnnnnnnn | nnnnnnnnnn | nnnnnnnnnn | nnnnnnnnnn | nnnnnnnnnn | nnnnnnnnnn | 16200 |
| nnnnnnnnnn | nnnnnnnnnn | nnnnnnnnnn | nnnnnnnnnn | nnnnnnnnnn | nnnnnnnnnn | 16260 |
| nnnnnnnnnn | nnnnnnnnnn | nnnnnnnnnn | nnnnnnnnnn | nnnnnnnnnn | nnnnnnnnnn | 16320 |
| nnnnnnnnnn | nnnnnnnnnn | nnnnnnnnnn | nnnnnnnnnn | nnnnnnnnnn | nnnnnnnnnn | 16380 |
| nnnnnnnnnn | nnnnnnnnnn | nnnnnnnnnn | nnnnnnnnnn | nnnnnnnnnn | nnnnnnnnnn | 16440 |
| nnnnnnnnnn | nnnnnnnnnn | nnnnnnnnnn | nnnnnnnnnn | nnnnnnnnnn | nnnnnnnnnn | 16500 |
| nnnnnnnnnn | nnnnnnnnnn | nnnnnnnnnn | nnnnnnnnnn | nnnnnnnnnn | nnnnnnnnnn | 16560 |
| nnnnnnnnnn | nnnnnnnnnn | nnnnnnnnnn | nnnnnnnnnn | nnnnnnnnnn | nnnnnnnnnn | 16620 |
| nnnnnnnnnn | nnnnnnnnnn | nnnnnnnnnn | nnnnnnnnnn | nnnnnnnnnn | nnnnnnnnnn | 16680 |
| nnnnnnnnnn | nnnnnnnnnn | nnnnnnnnnn | nnnnnnnnnn | nnnnnnnnnn | nnnnnnnnnn | 16740 |
| nnnnnnnnnn | nnnnnnnnnn | nnnnnnnnnn | nnnnnnnnnn | nnnnnnnnnn | nnnnnnnnnn | 16800 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 16860 |
| nnnnnnnnnn | nnnnnnnnnn | nnnnnnnnnn | nnnnnnnnnn | nnnnnnnnnn | nnnnnnnnnn | 16920 |
| nnnnnnnnnn | nnnnnnnnnn | nnnnnnnnnn | nnnnnnnnnn | nnnnnnnnnn | nnnnnnnnnn | 16980 |
| nnnnnnnnnn | nnnnnnnnnn | nnnnnnnnnn | nnnnnnnnnn | nnnnnnnnnn | nnnnnnnnnn | 17040 |
| nnnnnnnnnn | nnnnnnnnnn | nnnnnnnnnn | nnnnnnnnnn | nnnnnnnnnn | nnnnnnnnnn | 17100 |
| nnnnnnnnnn | nnnnnnnnnn | nnnnnnnnnn | nnnnnnnnnn | nnnnnnnnnn | nnnnnnnnnn | 17160 |
| nnnnnnnnnn | nnnnnnnnnn | nnnnnnnnnn | nnnnnnnnnn | nnnnnnnnnn | nnnnnnnnnn | 17220 |
| nnnnnnnnnn | nnnnnnnnnn | nnnnnnnnnn | nnnnnnnnnn | nnnnnnnnnn | nnnnnnnnnn | 17280 |
| nnnnnnnnnn | nnnnnnnnnn | nnnnnnnnnn | nnnnnnnnnn | nnnnnnnnnn | nnnnnnnnnn | 17340 |
| nnnnnnnnnn | nnnnnnnnnn | nnnnnnnnnn | nnnnnnnnnn | nnnnnnnnnn | nnnnnnnnnn | 17400 |
| nnnnnnnnnn | nnnnnnnnnn | nnnnnnnnnn | nnnnnnnnnn | nnnnnnnnnn | nnnnnnnnnn | 17460 |
| nnnnnnnnnn | nnnnnnnnnn | nnnnnnnnnn | nnnnnnnnnn | nnnnnnnnnn | nnnnnnnnnn | 17520 |
| nnnnnnnnnn | nnnnnnnnnn | nnnnnnnnnn | nnnnnnnnnn | nnnnnnnnnn | nnnnnnnnnn | 17580 |
| nnnnnnnnnn | nnnnnnnnnn | nnnnnnnnnn | nnnnnnnnnn | nnnnnnnnnn | nnnnnnnnnn | 17640 |
| nnnnnnnnnn | nnnnnnnnnn | nnnnnnnnnn | nnnnnnnnnn | nnnnnnnnnn | nnnnnnnnnn | 17700 |
| nnnnnnnnnn | nnnnnnnnnn | nnnnnnnnnn | nnnnnnnnnn | nnnnnnnnnn | nnnnnnnnnn | 17760 |
| nnnnnnnnnn | nnnnnnnnnn | nnnnnnnnnn | nnnnnnnnnn | nnnnnnnnnn | nnnnnnnnnn | 17820 |
| nnnnnnnnnn | nnnnnnnnnn | nnnnnnnnnn | nnnnnnnnnn | nnnnnnnnnn | nnnnnnnnnn | 17880 |
| nnnnnnnnnn | nnnnnnnnnn | nnnnnnnnnn | nnnnnnnnnn | nnnnnnnnnn | nnnnnnnnnn | 17940 |
| nnnnnnnnnn | nnnnnnnnnn | nnnnnnnnnn | nnnnnnnnnn | nnnnnnnnnn | nnnnnnnnnn | 18000 |
| nnnnnnnnnn | nnnnnnnnnn | nnnnnnnnnn | nnnnnnnnnn | nnnnnnnnnn | nnnnnnnnnn | 18060 |
| nnnnnnnnnn | nnnnnnnnnn | nnnnnnnnnn | nnnnnnnnnn | nnnnnnnnnn | nnnnnnnnnn | 18120 |
| nnnnnnnnnn | nnnnnnnnnn | nnnnnnnnnn | nnnnnnnnnn | nnnnnnnnnn | nnnnnnnnnn | 18180 |
| nnnnnnnnnn | nnnnnnnnnn | nnnnnnnnnn | nnnnnnnnnn | nnnnnnnnnn | nnnnnnnnnn | 18240 |
| nnnnnnnnnn | nnnnnnnnnn | nnnnnnnnnn | nnnnnnnnnn | nnnnnnnnnn | nnnnnnnnnn | 18300 |
| nnnnnnnnnn | nnnnnnnnnn | nnnnnnnnnn | nnnnnnnnnn | nnnnnnnnnn | nnnnnnnnnn | 18360 |
| nnnnnnnnnn | nnnnnnnnnn | nnnnnnnnnn | nnnnnnnnnn | nnnnnnnnnn | nnnnnnnnnn | 18420 |
| nnnnnnnnnn | nnnnnnnnnn | nnnnnnnnnn | nnnnnnnnnn | nnnnnnnnnn | nnnnnnnnnn | 18480 |
| nnnnnnnnnn | nnnnnnnnnn | nnnnnnnnnn | nnnnnnnnnn | nnnnnnnnnn | nnnnnnnnnn | 18540 |
| nnnnnnnnnn | nnnnnnnnnn | nnnnnnnnnn | nnnnnnnnnn | nnnnnnnnnn | nnnnnnnnnn | 18600 |
| nnnnnnnnnn | nnnnnnnnnn | nnnnnnnnnn | nnnnnnnnnn | nnnnnnnnnn | nnnnnnnnnn | 18660 |
| nnnnnnnnnn | nnnnnnnnnn | nnnnnnnnnn | nnnnnnnnnn | nnnnnnnnnn | nnnnnnnnnn | 18720 |
| nnnnnnnnnn | nnnnnnnnnn | nnnnnnnnnn | nnnnnnnnnn | nnnnnnnnnn | nnnnnnnnnn | 18780 |
| nnnnnnnnnn | nnnnnnnnnn | nnnnnnnnnn | nnnnnnnnnn | nnnnnnnnnn | nnnnnnnnnn | 18840 |
| nnnnnnnnnn | nnnnnnnnnn | nnnnnnnnnn | nnnnnnnnnn | nnnnnnnnnn | nnnnnnnnnn | 18900 |
| nnnnnnnnnn | nnnnnnnnnn | nnnnnnnnnn | nnnnnnnnnn | nnnnnnnnnn | nnnnnnnnnn | 18960 |
| nnnnnnnnnn | nnnnnnnnnn | nnnnnnnnnn | nnnnnnnnnn | nnnnnnnnnn | nnnnnnnnnn | 19020 |
| nnnnnnnnnn | nnnnnnnnnn | nnnnnnnnnn | nnnnnnnnnn | nnnnnnnnnn | nnnnnnnnnn | 19080 |
| nnnnnnnnnn | nnnnnnnnnn | nnnnnnnnnn | nnnnnnnnnn | nnnnnnnnnn | nnnnnnnnnn | 19140 |
| nnnnnnnnnn | nnnnnnnnnn | nnnnnnnnnn | nnnnnnnnnn | nnnnnnnnnn | nnnnnnnnnn | 19200 |

-continued

```
nnnnnnnnnn nnnnnnnnnn nnnnnnnnnn nnnnnnnnnn nnnnnnnnnn nnnnnnnnnn    19260
nnnnnnnnnn nnnnnnnnnn nnnnnnnnnn nnnnnnnnnn nnnnnnnnnn nnnnnnnnnn    19320
nnnnnnnnnn nnnnnnnnnn nnnnnnnnnn nnnnnnnnnn nnnnnnnnnn nnnnnnnnnn    19380
nnnnnnnnnn nnnnnnnnnn nnnnnnnnnn nnnnnnnnnn nnnnnnnnnn nnnnnnnnnn    19440
nnnnnnnnnn nnnnnnnnnn nnnnnnnnnn nnnnnnnnnn nnnnnnnnnn nnnnnnnnnn    19500
nnnnnnnnnn nnnnnnnnnn nnnnnnnnnn nnnnnnnnnn nnnnnnnnnn nnnnnnnnnn    19560
nnnnnnnnnn nnnnnnnnnn nnnnnnnnnn nnnnnnnnnn nnnnnnnnnn nnnnnnnnnn    19620
nnnnnnnnnn nnnnnnnnnn nnnnnnnnnn nnnnnnnnnn nnnnnnnnnn nnnnnnnnnn    19680
nnnnnnnnnn nnnnnnnnnn nnnnnnnnnn nnnnnnnnnn nnnnnnnnnn nnnnnnnnnn    19740
nnnnnnnnnn nnnnnnnnnn nnnnnnnnnn nnnnnnnnnn nnnnnnnnnn nnnnnnnnnn    19800
nnnnnnnnnn nnnnnnnnnn nnnnnnnnnn nnnnnnnnnn nnnnnnnnnn nnnnnnnnnn    19860
nnnnnnnnnn nnnnnnnnnn nnnnnnnnnn nnnnnnnnnn nnnnnnnnnn nnnnnnnnnn    19920
nnnnnnnnnn nnnnnnnnnn nnnnnnnnnn nnnnnnnnnn nnnnnnnnnn nnnnnnnnnn    19980
nnnnnnnnnn nnnnnnnnnn nnnnnnnnnn nnnnnnnnnn nnnnnnnnnn nnnnnnnnnn    20040
nnnnnnnnnn nnnnnnnnnn nnnnnnnnnn nnnnnnnnnn nnnnnnnnnn nnnnnnnnnn    20100
nnnnnnnnnn nnnnnnnnnn nnnnnnnnnn nnnnnnnnnn nnnnnnnnnn nnnnnnnnnn    20160
nnnnnnnnnn nnnnnnnnnn nnnnnnnnnn nnnccaaatc aaccagttgc ataaatcact    20220
cctctatctt ccttggggtg gaaagtggat gggagttata atttgagttc tcttttgtct    20280
tagtccattg aagctgctat tacaaaatac cataaactgg gtggcttata aacagcagaa    20340
atgaggccgg gtgcggtggc tcatgcctat aattccagca ctttgggagg ccaaggcagg    20400
tggatcacct gagatcagta gttcaagact agcctgacca acatggtgaa accctgtctc    20460
tactaaaaat acaaaaaatt agctgggggt ggtggcgggc acctgtaatc ccagctactc    20520
aggaggctga ggcaggagaa tcgcttgaac ccaggaggcg gaggttgccg tgagctgaga    20580
tcacgccatt gcatttcagc ctgggcacaa agagtgaaac tccatctcaa aatgaaataa    20640
aataacagaa atgtatttct taacagttct ggaggttggg tgggcagtcc cagatcagga    20700
cactgacaga ttcagtgtct gatgggggcc cactttctgg tgttacctgc tggctgtgtt    20760
ctcacatggt ggaaggaaca tggcaacttt ctggggcctt gttttttaat ttaaaaaaaa    20820
aaaatatttt cctggcccct tgcctgctgaa ggaacctctt ttataatggt acttaaaaat    20880
tttttttttt gagatggggg tctcactctg tcacccacgc tgagtgcagt atcacaatct    20940
cagctcactg caacctctgc ctccctggct taagcgatcc tcccacctca gcctcctgag    21000
tacgtgtgac cataggccca tggcacaaag cccagctaat tttttgtatt tttagtagaa    21060
atgtggtttc accatgttgc ataggctggt ctcgaacttc tgaactcaag tgatctgcct    21120
gccttggcct cccaaagtgc tgggattcta ggtatgagcc accctgctcg gcctataatg    21180
gcactttcct atcccattga tgaggctcta ctctcatgac ctaatcatct cccaaaggcc    21240
ctaaggcctc ctgataccat cacctttggg gttaggtttt aacatataca ttttgggggg    21300
acacagacat tttagaccat agcacctcca ttgaaaggaa acatttctga cacctggcta    21360
tctcaagggg ccctttcagt tccctgcag gctgcattcc cacatcacca acaagagcag    21420
cgacactcac tcagaggtta aataacttgt ccagagtcac agcagtaatg aatgacagag    21480
ctggggcttg aatccaggcg tcctcctaga gcctggattc tgtgtagtga gtgaaagctg    21540
```

```
actcctggga gacttctgcg tggtcctggt tctctctcca gactgcactg cgcaagtttc   21600
tcttcctgat ggtccctagg gtattacaaa gacagtggcc ctgcctgtca ggtgttttta   21660
ttaccagatg aggtcatggc ctcaggaacc ctgtaggaag ctgagttcag agtctttgag   21720
caggctttag ggaggttcca gcttccacc accaagcccc aggtggattc ttacagactc    21780
tagcctcagg gtgggggtc tggaagatga ggttgcgggg tgcgatattc tgcccaattc     21840
gcccctcctt gctcaatctg tttctgcagg tattgctgac tacagaccca aggatggaga   21900
aaccattgag ctgaggctgg ttagctggta gccctgagc tccctcatcc cagcagcctc     21960
gcacactccc taggcttcta ccctccctcc tgatgtccct ggaacaggaa ctcgcctgac   22020
cctgctgcca cctcctgtgc actttgagca atgcccctg ggatcacccc agccacaagc    22080
ccttcgaggg ccctatacca tggcccacct tggagcagag agccaagcat cttccctggg   22140
aagtctttct ggccaagtct ggccagcctg gccctgcagg tctcccatga aggccacccc   22200
atggtctgat gggcatgaag catctcagac tccttggcaa aaaacggagt ccgcaggccg   22260
caggtgttgt gaagaccact cgttctgtgg ttggggtcct gcaagaaggc ctcctcagcc   22320
cgggggctat ggccctgacc ccagctctcc actctgctgt tagagtggca gctccgagct   22380
ggttgtggca cagtagctgg ggagacctca gcagggctgc tcagtgcctg cctctgacaa   22440
aattaaagca ttgatggcct gtggacctgc tacagtggcc tggtgcctca tactcctcag   22500
gtgcaggggc agggacaaga gaaggggggaa gtaaccccat cagggaggag tggagggtgc   22560
ctgagccgcc atgtgggcat tggggagtg atgggaatgc cagcagtgat gacgttgact    22620
actgactgag cacccactac tatgactgag cactcactcg ctagatacta tcttgaactg   22680
ctctgtgagg ttgttgatat tttcattttt atctgtgctt tacaaatcag gaactgggaa   22740
ggccgggcgt ggtggctcac gcctgtaatc ccagcacttt aggaggccaa ggcaggtgga   22800
tcacaaggtc aggagtttga gatcagcctg gccaacatgg tgaaactcca tctttactaa   22860
aaatacaaaa aattagccag gcatggtgtt gcatgcctgc atgcctgtaa tcccagttac   22920
ttgggaagct gaggcaggag aattgcttga acctgagg cggaggttgt agtgagccga    22980
gatcacgcca ttgcactcca gcttgggcaa gaagagaaac actctcaaaa aaaaaaaaa    23040 atcaggaaac tggtgctcaa aaaggaaaag tgactcacca aggtcacaga ctaggcagtg   23100
atgctggggg aacctggctc aggggacaca gacctggcct ggggcagcct tgcagctcct   23160
ccactaaaat actgaaaatg aggggcttcg atgatggtta taatcgtatg gcagagcccc   23220
aactcaactg gagccctggg acccagaagc tagggtctca ctccctgctt ttccacaagg   23280
caccattagg gcatcacccc aggcctcggc agccacgacg cagggatcct gcctctcatt    23340 ggttggggc ttagggctc tgggctgccc tcttgaagag ggggttcagc ccagcgaggc     23400
accccctatg ctgcacccca ccaaggttag aagaggtcc tgtcctcagt ggggccctct    23460
gatgaacagc ccatcaggtc tgcgtccaca tgccttggaa gagatggtga catactcaaa   23520
gtccttgaag ccgcatatta aaccacctag agcaccatct tcaaacattt agggtctgag   23580
aagatagggg aagtaagcaa tttaaaacat ttctttatat tgggccaggt gcaatggctc    23640
acgtctgtaa tcccagcgct ttgggaggac gaggatcacc tgaggtcagg agttcaagat   23700
cagcctggcc aacatggaga aacccatct ctactaaaaa tacaaaaatt agctcaggcg    23760
tggtgatgtg cacctgtaat cctagctatt caggaggctg aggcacaaga attgcttgag   23820
tcaatattgc accactgcac tccagcctgg gcaacagcga gactcttgtc tcaaaaaaaa    23880
aaaaagatat ttgctgaaaa gacccagcct gccaaactca ggggcagcca agggaggtag    23940
```

-continued

```
tgaaatggaa gttggagctc agcgctccca cacctccact gccctcaggc cttctctgcc    24000
tctttcccat cagtcagctg cttctgggca tggtcctggc agagacttgg cctccttcca    24060
gttcaagctc cctcttagat tgtgtcccac gccactgagt ctttgggaca ctgggtcaga    24120
tgtctagtct ggcacaattg gcaggaatcc aagaaacag tgtgagtgag gggacagtcg     24180
tgttgagtgc cctccatctg ggactgggag gcaggtctat gtcaggcctg catttagatc    24240
tctaatggct ccagacaagc cccttcagct cactaagcct gtttcctaac acagctgtgg    24300
gatggtgctt tggtttacat agcacgcgat accatcatag atcacatggg gaaactgagg    24360
ccccaggagt gatctgctgg cacatgcagt gacaagagga gaggcccatc tcagccttgc    24420
agcaaggttg ccagaaatcg attctcgccc ccatcccgta agatagctg ggattacagg     24480 tgtgcaccac catgcccagc ctaattttg tattattagt agagatgggg tttcaccatg      24540
ttgtccaggc tggtcatgaa ctcctgacct caagtgatcc acccgctttg gcctcccaaa    24600
gtgctgggat tacaagcatg agccacagtg cctggcctga ccctgctctt tgaaagacc     24660 attcccccaa attctgtgca cctgtgtgcc tttcttctct ctgcctcctc tcagctctgc    24720
cccgctctcc tcccttctcc tctggcaaat cccactcatc tcttgaagcc cttcttccag    24780
gggaagccct gatcatgctg ctttctcctg tgggagggat gaaggacgtg gcccacggag    24840 tttgtttgt tttgtttga gatggagttt tgctcatgtt gcccaggctg ggtacaatg        24900 gtacgatctc agctcactgc aacctctacg tcccgggttc aagcggttct cctgccttag    24960
cctccccagt agctgggatt actggcatga accaccacac ctggctaatt ttgtgttttt    25020
agtagagatg gggtttcttc atgttggtca ggctggtctc gaactcccaa cctcaggtga    25080
tctgcctgcc tcggcctccc aaagtactgg gattacaggg ttgagccact gtgcctggcc    25140
caggcccacg gagttttaag aggcttcctg tggcagtggc atccagacgg agtgcagaaa    25200
ctcaaagttg aaggccagaa gctcagggaa gggggagtgt gagttgagga gtctcttggc    25260
tgccagggcc agaaaccgaa ctccaagcct ctccacaaca gcgggtgtag agcatgtaga    25320
atcagagagg aggctgagcc atgcagcccc gagaagaggg gaatgccact gagccacaga    25380
gacccagtgc cactgccagg tgtctctgcc tccacttccc atgacccggc ctgtctctgt    25440
atgcaggctt caccctctct cgttgtacat tgtacacatt ctaggtgaca ccagcagctt    25500
ctgattctca tctcccataa catcagcccc ccagagaggg gacaactgct gagctgataa    25560
cataatagat gcccctttcc tggaggccat ggtcatggtc agcgtggaga ggatgaagcc    25620
tgagcaggca ggatcggggg tctagagggg aaggaggtgg aagttgagat cacagacctg    25680
tggtcaggtg gcctgggaag ggtttgacga gtgtcggccc aaagagcttg gaagggatt    25740 tgctgctgtg ggtgagcact gcctctcccc ttagggacaa cagccacctc ttctctcccc    25800
atttgccttt cccttctgta gatatgaaac acaggcctcc ttgtcaggcc cctacttaac    25860
ctccgtgatg gggaaagcgg ccggagaaag ggagttctgg cagcttctcc gagaccccaa    25920 cacccactg ttgcaaggtg agtcatggcc tgacactctg gatgtgtccc ctaccccaag     25980
cttactcagc caagaggctt catcaactca ccccagcttt ccctagcacc tcctgggcc     26040 acaccttcac aaaatcactg atgctcaaag ttggatataa tatattgaac tgaagcctta    26100
gcatttttat gcaagttact gtggaaattc taggaaacca gacagattac aaaaaaaaaa    26160
aaaaactaga agaaaattaa catccactag gatatactac ctaggaataa cgtcttttat    26220
tttgagatgg agtttcgctc ttgttgccca ggctggagtg cagcggtatg atctcggctc    26280
```

-continued

```
gctgcaacct ccgcctcctg ggttcatgtg attcttccac ctcggccttc ctagagccca    26340
agtggtctgc ctgcctctgc ctcccaaagt tctgggatta caggcatgag ccaccgcacc    26400
cagccaaaat tacttaactt ttcttctaga tactttttaa aaatatggca gtaagttttt    26460
cataaaaaat ggagccatgc tatccagtgg aaatttaatg ttgcccacat gtataactta    26520
aaaatttcat atatgtgtat acatatatat gaaatatata tatacagaca cacatatata    26580
tgtatacata tatatacaca tatatatgta tacatatata cacacatata tgtatacata    26640
tatatacaca catatacaca tatatacaca cacatacata tatacacaca catatataca    26700
cacatatata cacacatgca cacatatata tgtatacata tatacacaca tgtatacgta    26760
tatatacaca catatataca cacatatata tacacacata tacacacata cacacacata    26820
tatacacaca tatatacaca catatataca cacatatata tgtatacata tatatacaca    26880
catatataca catacacaca tacatatata cacatataca catatacaca cacatataca    26940
cacatgtata catatatata cacacatgta tacatatgta tacacacaca tatatgtata    27000
catatataca cacatacata tgtgtacata tatacacaca tacatatgta tacatatata    27060
cacacat                                                              27067
```

<210> SEQ ID NO 6
<211> LENGTH: 427
<212> TYPE: PRT
<213> ORGANISM: Human

<400> SEQUENCE: 6

```
Met Arg His Leu Gly Ala Phe Leu Phe Leu Leu Gly Val Leu Gly Ala
  1               5                  10                  15

Leu Thr Glu Met Cys Glu Ile Pro Glu Met Asp Ser His Leu Val Glu
                 20                  25                  30

Lys Leu Gly Gln His Leu Leu Pro Trp Met Asp Arg Leu Ser Leu Glu
             35                  40                  45

His Leu Asn Pro Ser Ile Tyr Val Gly Leu Arg Leu Ser Ser Leu Gln
         50                  55                  60

Ala Gly Thr Lys Glu Asp Leu Tyr Leu His Ser Leu Lys Leu Gly Tyr
 65                  70                  75                  80

Gln Gln Cys Leu Leu Gly Ser Ala Phe Ser Glu Asp Gly Asp Cys
                 85                  90                  95

Gln Gly Lys Pro Ser Met Gly Gln Leu Ala Leu Tyr Leu Leu Ala Leu
                100                 105                 110

Arg Ala Asn Cys Glu Phe Val Arg Gly His Lys Gly Asp Arg Leu Val
            115                 120                 125

Ser Gln Leu Lys Trp Phe Leu Glu Asp Glu Lys Arg Ala Ile Gly His
        130                 135                 140

Asp His Lys Gly His Pro His Thr Ser Tyr Tyr Gln Tyr Gly Leu Gly
145                 150                 155                 160

Ile Leu Ala Leu Cys Leu His Gln Lys Arg Val His Asp Ser Val Val
                165                 170                 175

Asp Lys Leu Leu Tyr Ala Val Glu Pro Phe His Gln Gly His His Ser
                180                 185                 190

Val Asp Thr Ala Ala Met Ala Gly Leu Ala Phe Thr Cys Leu Lys Arg
            195                 200                 205

Ser Asn Phe Asn Pro Gly Arg Arg Gln Arg Ile Thr Met Ala Ile Arg
        210                 215                 220

Thr Val Arg Glu Glu Ile Leu Lys Ala Gln Thr Pro Glu Gly His Phe
```

```
                225                 230                 235                 240
Gly Asn Val Tyr Ser Thr Pro Leu Ala Leu Gln Phe Leu Met Thr Ser
                    245                 250                 255

Pro Met Arg Gly Ala Glu Leu Gly Thr Ala Cys Leu Lys Ala Arg Val
                260                 265                 270

Ala Leu Leu Ala Ser Leu Gln Asp Gly Ala Phe Gln Asn Ala Leu Met
            275                 280                 285

Ile Ser Gln Leu Leu Pro Val Leu Asn His Lys Thr Tyr Ile Asp Leu
        290                 295                 300

Ile Phe Pro Asp Cys Leu Ala Pro Arg Val Met Leu Glu Pro Ala Ala
305                 310                 315                 320

Glu Thr Ile Pro Gln Thr Gln Glu Ile Ile Ser Val Thr Leu Gln Val
                    325                 330                 335

Leu Ser Leu Leu Pro Pro Tyr Arg Gln Ser Ile Ser Val Leu Ala Gly
                340                 345                 350

Ser Thr Val Glu Asp Val Leu Lys Lys Ala His Glu Leu Gly Gly Phe
            355                 360                 365

Thr Tyr Glu Thr Gln Ala Ser Leu Ser Gly Pro Tyr Leu Thr Ser Val
        370                 375                 380

Met Gly Lys Ala Ala Gly Glu Arg Glu Phe Trp Gln Leu Leu Arg Asp
385                 390                 395                 400

Pro Asn Thr Pro Leu Leu Gln Gly Ile Ala Asp Tyr Arg Pro Lys Asp
                    405                 410                 415

Gly Glu Thr Ile Glu Leu Arg Leu Val Ser Trp
                420                 425

<210> SEQ ID NO 7
<211> LENGTH: 427
<212> TYPE: PRT
<213> ORGANISM: Human

<400> SEQUENCE: 7

Met Arg His Leu Gly Ala Phe Leu Phe Leu Leu Gly Val Leu Gly Ala
1               5                   10                  15

Leu Thr Glu Met Cys Glu Ile Pro Glu Met Asp Ser His Leu Val Glu
                20                  25                  30

Lys Leu Gly Gln His Leu Leu Pro Trp Met Asp Arg Leu Ser Leu Glu
            35                  40                  45

His Leu Asn Pro Ser Ile Tyr Val Gly Leu Arg Leu Ser Ser Leu Gln
        50                  55                  60

Ala Gly Thr Lys Glu Asp Leu Tyr Leu His Ser Leu Lys Leu Gly Tyr
65                  70                  75                  80

Gln Gln Cys Leu Leu Gly Ser Ala Phe Ser Glu Asp Asp Gly Asp Cys
                85                  90                  95

Gln Gly Lys Pro Ser Met Gly Gln Leu Ala Leu Tyr Leu Leu Ala Leu
                100                 105                 110

Arg Ala Asn Cys Glu Phe Val Arg Gly His Lys Gly Asp Arg Leu Val
            115                 120                 125

Ser Gln Leu Lys Trp Phe Leu Glu Asp Glu Lys Arg Ala Ile Gly His
        130                 135                 140

Asp His Lys Gly His Pro His Thr Ser Tyr Tyr Gln Tyr Gly Leu Gly
145                 150                 155                 160

Ile Leu Ala Leu Cys Leu His Gln Lys Arg Val His Asp Ser Val Val
                165                 170                 175
```

-continued

```
Asp Lys Leu Leu Tyr Ala Val Glu Pro Phe His Gln Gly His His Ser
            180                 185                 190
Val Asp Thr Ala Ala Met Ala Gly Leu Ala Phe Thr Cys Leu Lys Arg
        195                 200                 205
Ser Asn Phe Asn Pro Gly Arg Arg Gln Arg Ile Thr Met Ala Ile Arg
    210                 215                 220
Thr Val Arg Glu Glu Ile Leu Lys Ala Gln Thr Pro Glu Gly His Phe
225                 230                 235                 240
Gly Asn Val Tyr Ser Thr Pro Leu Ala Leu Gln Phe Leu Met Thr Ser
            245                 250                 255
Pro Met Arg Gly Ala Glu Leu Gly Thr Ala Cys Leu Lys Ala Arg Val
            260                 265                 270
Ala Leu Leu Ala Ser Leu Gln Asp Gly Ala Phe Gln Asn Ala Leu Met
        275                 280                 285
Ile Ser Gln Leu Leu Pro Val Leu Asn His Lys Thr Tyr Ile Asp Leu
    290                 295                 300
Ile Phe Pro Asp Cys Leu Ala Pro Arg Val Met Leu Glu Pro Ala Ala
305                 310                 315                 320
Glu Thr Ile Pro Gln Thr Gln Glu Ile Ile Ser Val Thr Leu Gln Val
            325                 330                 335
Leu Ser Leu Leu Pro Pro Tyr Arg Gln Ser Ile Ser Val Leu Ala Gly
            340                 345                 350
Ser Thr Val Glu Asp Val Leu Lys Lys Ala His Glu Leu Gly Gly Phe
        355                 360                 365
Thr Tyr Glu Thr Gln Ala Ser Leu Ser Gly Pro Tyr Leu Thr Ser Val
    370                 375                 380
Met Gly Lys Ala Ala Gly Glu Arg Glu Phe Trp Gln Leu Leu Arg Asp
385                 390                 395                 400
Pro Asn Thr Pro Leu Leu Gln Gly Ile Ala Asp Tyr Arg Pro Lys Asp
            405                 410                 415
Gly Glu Thr Ile Glu Leu Arg Leu Val Ser Trp
            420                 425
```